US011220689B2

(12) United States Patent
Agarwal et al.

(10) Patent No.: US 11,220,689 B2
(45) Date of Patent: Jan. 11, 2022

(54) MODULATORS OF TELOMERE DISEASE

(71) Applicant: Children's Medical Center Corporation, Boston, MA (US)

(72) Inventors: Suneet Agarwal, Lexington, MA (US); Diane Moon, Boxford, MA (US); Baris Boyraz, Cambridge, MA (US); Matthew Segal, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/768,424

(22) PCT Filed: Oct. 17, 2016

(86) PCT No.: PCT/US2016/057409
§ 371 (c)(1),
(2) Date: Apr. 13, 2018

(87) PCT Pub. No.: WO2017/066796
PCT Pub. Date: Apr. 20, 2017

(65) Prior Publication Data
US 2019/0211339 A1 Jul. 11, 2019

Related U.S. Application Data

(63) Continuation-in-part of application No. PCT/US2016/057229, filed on Oct. 14, 2016.

(60) Provisional application No. 62/308,427, filed on Mar. 15, 2016, provisional application No. 62/242,970, filed on Oct. 16, 2015.

(51) Int. Cl.
| C12N 15/11 | (2006.01) |
| C12N 15/113 | (2010.01) |
| A61K 45/06 | (2006.01) |
| A61K 31/7036 | (2006.01) |
| A61K 31/7052 | (2006.01) |
| A61K 31/713 | (2006.01) |
| C12N 9/16 | (2006.01) |
| C12N 9/12 | (2006.01) |
| A61K 31/7048 | (2006.01) |
| G01N 33/573 | (2006.01) |
| C12Q 1/6883 | (2018.01) |
| C12Q 1/6886 | (2018.01) |
| G01N 33/68 | (2006.01) |
| A61K 38/00 | (2006.01) |
| C07K 16/40 | (2006.01) |

(52) U.S. Cl.
CPC ...... *C12N 15/1137* (2013.01); *A61K 31/7036* (2013.01); *A61K 31/7048* (2013.01); *A61K 31/7052* (2013.01); *A61K 31/713* (2013.01); *A61K 38/005* (2013.01); *A61K 45/06* (2013.01); *C07K 16/40* (2013.01); *C12N 9/1241* (2013.01); *C12N 9/16* (2013.01); *C12Q 1/6883* (2013.01); *C12Q 1/6886* (2013.01); *C12Y 207/07019* (2013.01); *C12Y 301/13004* (2013.01); *G01N 33/573* (2013.01); *G01N 33/6893* (2013.01); *C07K 2319/00* (2013.01); *C07K 2319/80* (2013.01); *C12N 2310/11* (2013.01); *C12N 2310/122* (2013.01); *C12N 2310/14* (2013.01); *C12N 2310/20* (2017.05); *C12Q 2600/106* (2013.01); *C12Q 2600/136* (2013.01); *C12Q 2600/156* (2013.01); *C12Q 2600/158* (2013.01); *G01N 2333/91245* (2013.01); *G01N 2500/10* (2013.01)

(58) Field of Classification Search
CPC .................. C12N 15/113; C12N 2310/14
See application file for complete search history.

(56) References Cited

U.S. PATENT DOCUMENTS

| 4,458,066 A | 7/1984 | Caruthers et al. |
| 4,522,811 A | 6/1985 | Eppstein et al. |
| 4,980,286 A | 12/1990 | Morgan et al. |
| 5,071,743 A | 12/1991 | Slilaty et al. |
| 5,328,470 A | 7/1994 | Nabel et al. |
| 5,702,931 A | 12/1997 | Andrews et al. |
| 5,780,270 A | 7/1998 | Lesley |
| 5,789,166 A | 8/1998 | Bauer et al. |
| 5,932,419 A | 8/1999 | Bauer et al. |
| 6,242,222 B1 | 6/2001 | Gifford |
| 6,468,798 B1 | 10/2002 | Debs et al. |
| 6,503,713 B1 | 1/2003 | Rana |
| 8,901,284 B2 | 12/2014 | Vlassov et al. |
| 2005/0048542 A1 | 3/2005 | Baker et al. |
| 2006/0052324 A1 | 3/2006 | Artandi et al. |
| 2007/0191294 A1 | 8/2007 | Elmen et al. |
| 2008/0249039 A1 | 10/2008 | Elmen et al. |

(Continued)

FOREIGN PATENT DOCUMENTS

| EP | 0043075 | 6/1981 |
| JP | H1047381 | 2/1998 |

(Continued)

OTHER PUBLICATIONS

Boele et al., PAPD5-mediated 3' adenylation and subsequent degradation of miR-21 is disrupted in proliferative disease, PNAS, vol. 111, pp. 11467-11472. (Year: 2014).*

(Continued)

*Primary Examiner* — Dana H Shin
(74) *Attorney, Agent, or Firm* — Fish & Richardson P.C.

(57) ABSTRACT

The disclosure relates to treating and diagnosing telomere diseases, and methods of screening agents for treating and diagnosing telomere diseases.

1 Claim, 37 Drawing Sheets
Specification includes a Sequence Listing.

(56) References Cited

U.S. PATENT DOCUMENTS

| | | | |
|---|---|---|---|
| 2009/0143326 | A1 | 6/2009 | Obad et al. |
| 2009/0181914 | A1 | 7/2009 | Rosenbohm et al. |
| 2009/0298916 | A1 | 12/2009 | Kauppinen et al. |
| 2010/0004320 | A1 | 1/2010 | Elmen et al. |
| 2010/0008917 | A1 | 1/2010 | Hosken et al. |
| 2010/0204217 | A1 | 8/2010 | Kallick |
| 2010/0234451 | A1 | 9/2010 | Worm |
| 2010/0249052 | A1 | 9/2010 | Benson et al. |
| 2010/0317718 | A1 | 12/2010 | Marcusson et al. |
| 2012/0071349 | A1 | 3/2012 | Qi |
| 2013/0323220 | A1 | 12/2013 | Joung et al. |
| 2014/0304845 | A1 | 10/2014 | Loboda et al. |

FOREIGN PATENT DOCUMENTS

| | | |
|---|---|---|
| WO | WO 89/02468 | 3/1989 |
| WO | WO 89/05345 | 6/1989 |
| WO | WO 89/07136 | 8/1989 |
| WO | WO 91/06309 | 5/1991 |
| WO | WO 92/07573 | 5/1992 |
| WO | WO 2004/081179 | 9/2004 |
| WO | WO 2004/092395 | 10/2004 |
| WO | WO 2008/119027 | 10/2008 |
| WO | WO 2010/040112 | 4/2010 |
| WO | WO 2010/118419 | 10/2010 |
| WO | WO 2010/129746 | 11/2010 |
| WO | WO 2011/108699 | 9/2011 |
| WO | WO 2013/003384 | 1/2013 |
| WO | WO 2014/127290 | 8/2014 |

OTHER PUBLICATIONS

Fok et al., Posttranscriptional modulation of TERC by PAPD5 inhibition rescues hematopietic development in dyskeratosis congenita, Blood, vol. 133, pp. 1308-1312. (Year: 2019).*

Shukla et al., Inhibition of telomerase RNA decay rescues telomerase deficiency caused by dyskerin or PARN defects, Nature Structural & Molecular Biology, vol. 23, pp. 286-292. (Year: 2016).*

Adams et al., "Hindered dialkylamino nucleoside phosphite reagents in the synthesis of two DNA 51-mers," J. Am. Chem. Soc. 105(3):661-3, Feb. 1983.

Ahmadian et al., "Single-nucleotide polymorphism analysis by pyrosequencing," Anal. Biochem., 280(1):103-110, Apr. 2000.

Alter et al., "Cancer in dyskeratosis congenita," Blood, 113(26):6549-57, Jun. 2009.

Altschul et al., "Basic local alignment search tool," J. Mol. Biol., 215(3):403-410, Oct. 1990.

Angag and Schutz, "General method for site-directed mutagenesis," Biotech., 30(3):486-488, Mar. 2001.

Armanios et al., "Telomerase mutations in families with idiopathic pulmonary fibrosis," N. Engl. J. Med., 356(13):1317-26, Mar. 2007.

Armentano et al., "Expression of human factor IX in rabbit hepatocytes by retrovirus-mediated gene transfer: potential for gene therapy of hemophilia B," Proc. Natl. Acad. Sci. U.S.A., 87(16):6141-6145, Aug. 1990.

Aubert et al., "Collapse of telomere homeostasis in hematopoietic cells caused by heterozygous mutations in telomerase genes," PLoS Genet., 8(5):e1002696, May 2012.

Bagella et al., "Cloning of murine CDK9/PITALRE and its tissue-specific expression in development," J. Cell. Physiol., 177(2):206-213, Nov. 1998.

Balatsos et al., "Competitive inhibition of human poly (A)-specific ribonuclease (PARN) by synthetic fluoro-pyranosyl nucleosides," Biochemistiy, 48(26):6044-51, Jun. 2009.

Beaucage and Caruthers, "Deoxynucleoside phosphoramidites—a new class of key intermediates for deoxypolynucleotide synthesis," Tetra. Lett., 22(20):1859-62, Jan. 1981.

Belousov et al., "Sequence-specific targeting and covalent modification of human genomic DNA," Nucleic. Acids. Res., 25(7):3440-3444, Sep. 1997.

Benton and Davis, "Screening lambdagt recombinant clones by hybridization to single plaques in situ," Science, 196(4286):180-2, Apr. 1977.

Berkner et al., "Development of adenovirus vectors for the expression of heterologous genes," BioTechniques, 6(7):616-29, Jul. 1988.

Bernard and Wirrwer, "Real-time PCR technology for cancer diagnostics," Clin. Chem., 48(8):1178-1185, Aug. 2002.

Berndt et al., "Maturation of mammalian H/ACA box sno RNAs: PAPD5-dependenet adenylation and PARN-dependent trimming," RNA, 18(5):958-972, May 2012.

Bianchi et al., "A serum circulating miRNA diagnostic test to identify asymptomatic high-risk individuals with early stage lung cancer," EMBO Mol. Med., 3(8):495-503, Aug. 2011.

Blommers et al., "Effects of the introduction of L-nucleotides into DNA. Solution structure of the heterochiral duplex d(G-C-G-(L)T-G-C-G).d(C-G-C-A-C-G-C) studied by NMR spectroscopy," Biochemistiy, 33(25):7886-7896, Jun. 1994.

Boles and Miogsa, "A rapid and highly efficient method for PCR-based site-directed mutagenesis using only one new primer," Curr. Genet., 28(2):197-198, Jul. 1995.

Bolger et al., "Trimmomatic: a flexible trimmer for Illumina sequence data," Bioinformatics., 30(15):2114-20, Aug. 2014.

Boyraz et al., "Posttranscriptional Manipulation of TERC Reverses Molecular Hallmarks of Telomere Disease," The Journal of Clinical Investigation, Sep. 2016, 136: 3377-3382.

Brody et al., "High-content affinity-based proteomics: unlocking protein biomarker discovery," Expert. Rev. Mol. Diagn., 10(8):1013-1022, Nov. 2010.

Brown et al., "Chemical synthesis and cloning of a tyrosine tRNA gene," Meth. Enzymol., 68:109-51, 1979.

Calado et al., "Constitutional telomerase mutations are genetic risk factors for cirrhosis," Hepatology, 53(5):1600-7, May 2011.

Cao et al., "Increased copy number of the TERT and TERC telomerase subunit genes in cancer cells," Cancer science, 99(6):1092-9, Jun. 2008.

Chen et al., "Gene therapy for brain tumors: regression of experimental gliomas by adenovirus-mediated gene transfer in vivo," PNAS. USA., 91(8):3054-3057, Apr. 1994.

Chowdhury et al., "Long-term improvement of hypercholesterolemia after ex vivo gene therapy in LDLR-deficient rabbits," Science, 254(5039):1802-1805, Dec. 1991.

Codd et al., "Common variants near TERC are associated with mean telomere length," Nature genetics, 42(3):197-9, Mar. 2010.

Cohen et al., "Sustained delivery and expression of DNA encapsulated in polymeric nanoparticles," Gene. Ther., 7(22):1896-905, Nov. 2000.

Cristofari and Lingner, "Telomere length homeostasis requires that telomerase levels are limiting," The EMBO journal, 25(3):565-74, Feb. 2006.

Czarnik, "Encoding methods for combinatorial chemistry," Curr. Opin. Chem. Biol., 1(1):60-6, Jun. 1997.

Dai et al., "Gene therapy via primary myoblasts: long-term expression of factor IX protein following transplantation in vivo," Proc. Natl. Acad. Sci. USA., 89(22):10892-10895, Nov. 1992.

Danos and Mulligan, "Safe and efficient generation of recombinant retroviruses with amphotropic and ecotropic host ranges," Proc. Natl. Acad. Sci. USA., 85(17):6460-6464, Sep. 1988.

Dehlin et al., "Cap-dependent deadenylation of mRNA," The EMBO journal, 19(5):1079-86, Mar. 2000.

Diehl et al., "BEAMing: single-molecule PCR on microparticles in water-in-oil emulsions," Nat. Methods, 3(7):551-559, Jul. 2006.

Egan and Collins, "An enhanced H/ACA RNP assembly mechanism for human telomerase RNA," Mol. Cell Biol., 32(13):2428-39, Jul. 2012.

Egecioglu et al., "Contributions of Trf4p-and Trf5p-dependent polyadenylation to the processing and degradative functions of the yeast nuclear exosome," RNA, 12(1):26-32, Jan. 2006.

Eglitis et al., "Gene expression in mice after high efficiency retroviral-mediated gene transfer," Science, 230(4732):1395-1398, Dec. 1985.

Ekins and Chu, "Microarrays: their origins and applications," Trends in Biotechnology., 17(6):217-218, Jun. 1999.

Extended European Search Report in European Application No. 16856437.5 dated Jun. 4, 2019, 11 pages.

(56) References Cited

OTHER PUBLICATIONS

Feng et al., "The RNA component of human telomerase," Science 269(5228):1236-41, Sep. 1995.
Ferry et al., "Retroviral-mediated gene transfer into hepatocytes in vivo," Proc. Natl. Acad. Sci. USA., 88(19):8377-8381, Oct. 1991.
Flotte et al., "Expression of the cystic fibrosis transmembrane conductance regulator from a novel adeno-associated virus promoter," J. Biol. Chem., 268(5):3781-3790, Feb. 1993.
Flotte et al., "Gene expression from adeno-associated virus vectors in airway epithelial cells," Am. J. Respir. Cell. Mol. Biol., 7(3):349-356, Sep. 1992.
Fok et al., "Posttranscriptional modulation of TERC by PAPD5 inhibition rescues hematopoietic development in dyskeratosis congenita," Blood, 133(12):1308-12, Mar. 2019.
Frenkel et al., "7,12-dimethylbenz[a]anthracene induces oxidative DNA modification in vivo," Free Radic. Biol. Med., 19(3):373-380, Sep. 1995.
Fu and Collins, "Distinct biogenesis pathways for human telomerase RNA and H/ACA small nucleolar RNAs," Mol. Cell, 11(5):1361-72, May 2003.
Fukuoka et al., "Ligand binding sites on guinea pig C3aR: point and deletion mutations in the large extracellular loop and vicinity," Biochem. Biophys. Res. Commun., 263(2):357-360, Sep. 1999.
Gaultier et al., "Alpha-DNA. IV: Alpha-anomeric and beta-anomeric tetrathymidylates covalently linked to intercalating oxazolopyridocarbazole. Synthesis, physicochemical properties and poly (rA) binding," Nucleic. Acids. Res., 15(16):6625-6641, Aug. 1987.
Goldfarb and Cech, "3' terminal diversity of MRP RNA and other human noncoding RNAs revealed by deep sequencing," BMC molecular biology, 14:23, Sep. 2013.
Greider, "Telomerase RNA levels limit the telomere length equilibrium," Cold Spring Harbor symposia on quantitative biology, 71:225-9, 2006.
Grunstein and Hogness, "Colony hybridization: a method for the isolation of cloned DNAs that contain a specific gene," Proc. Natl. Acad. Sci. U.S.A., 72(10):3961-5, Oct. 1975.
Haj-Ahmand and Graham, "Development of a helper-independent human adenovirus vector and its use in the transfer of the herpes simplex vims thymidine kinase gene," J. Virol., 57(1):267-74, Jan. 1986.
Hao et al., "Short telomeres, even in the presence of telomerase, limit tissue renewal capacity," Cell, 123(6):1121-31, Dec. 2005.
Heasman, "Morpholino oligos: making sense of antisense?," Dev. Biol., 243(2):209-14, Mar. 2002.
Heiss et al., "X-linked dyskeratosis congenita is caused by mutations in a highly conserved gene with putative nucleolar functions," Nat. Genet. 19(1):32-8, May 1998.
Helene et al., "Control of gene expression by triple helix-forming oligonucleotides. The antigene strategy," Ann. N.Y. Acad. Sci., 660:27-36, Oct. 1992.
Helene, "The anti-gene strategy: control of gene expression by triplex-forming-oligonucleotides," Anticancer Drug Des., 6(6):569-84, Dec. 1991.
Hermonat and Muzyczka, "Use of adeno-associated virus as a mammalian DNA cloning vector: transduction of neomycin resistance into mammalian tissue culture cells," Proc. Natl. Acad. Sci. USA, 81(20):6466-6470, Oct. 1984.
Houseley and Tollervey, "The many pathways of RNA degradation," Cell, 136(4):763-76, Feb. 2009.
Huber et al., "Retroviral-mediated gene therapy for the treatment of hepatocellular carcinoma: an innovative approach for cancer therapy," Proc. Natl. Acad. Sci. USA, 88(18):8039-8043, Sep. 1991.
Hwu et al., "Functional and molecular characterization of tumor-infiltrating lymphocytes transduced with tumor necrosis factor-alpha cDNA for the gene therapy of cancer in humans," J. Immunol., 150(9):4104-4115, May 1993.
Inoue et al., "Sequence-dependent hydrolysis of RNA using modified oligonucleotide splints and RNase H," FEBS Lett., 215(2):327-330, May 1987.

Inoue et al., "Synthesis and hybridization studies on two complementary nona(2'-O-methyl)ribonucleotides," Nucleic Acids. Res., 15(15):6131-6148, Aug. 1987.
International Preliminary Report on Patentability in International Application No. PCT/US2016/057229, dated Apr. 17, 2018, 8 pages.
International Preliminary Report on Patentability in International Application No. PCT/US2016/057409, dated May 8, 2017, 12 pages.
International Search Report and Written Opinion in International Application No. PCT/US16/57229, dated Apr. 25, 2017, 16 pages.
International Search Report and Written Opinion in International Application No. PCT/US16/57409, dated May 8, 2017, 22 pages.
Iversen, "Phosphorodiamidate morpholino oligomers: favorable properties for sequence-specific gene inactivation.," Curr. Opin. Mol. Ther., 3(3):235-8, Jun. 2001.
Jongmans et al., "Revertant somatic mosaicism by mitotic recombination in dyskeratosis congenita," Am. J. Hum. Genet, 90(3):426-33, Mar. 2012.
Kang et al., "Transient Gene Transfer into Myotubes Following Differentiation in Culture," Biotech. 20(1):40-46, Jan. 1996.
Kay et al., "Hepatic gene therapy: persistent expression of human alpha 1-antitrypsin in mice after direct gene delivery in vivo," Human Gene Therapy, 3(6):641-647, Dec. 1992.
Kim and Maas, "Multiple site mutagenesis with high targeting efficiency in one cloning step," BioTech., 28(2):196-198, Feb. 2000.
Kim et al., "Automated heart-type fatty acid-binding protein assay for the early diagnosis of acute myocardial infarction," Am. J. Clin. Pathol., 134(1):157-162, Jul. 2010.
Kim et al., "HISAT: a fast spliced aligner with low memory requirements," Nat. Methods, 12(4):357-60, Apr. 2015.
Kirsch and Joly, "An improved PCR-mutagenesis strategy for two-site mutagenesis or sequence swapping between related genes," Nuc. Acids. Res., 26(7):1848-1850, Apr. 1998.
Kirwan et al., "Defining the pathogenic role of telomerase mutations in myelodysplastic syndrome and acute myeloid leukemia," Human mutation, 30(11):1567-73, Nov. 2009.
Kirwan et al., "Exogenous TERC alone can enhance proliferative potential, telomerase activity and telomere length in lymphocytes from dyskeratosis congenita patients," British journal of haematology, 144(5):771-81, Mar. 2009.
Kiss et al., "Box H/ACA small ribonucleoproteins," Molecular cell, 37(5):597-606, Mar. 2010.
Korner and Wahle, "Poly (A) tail shortening by a mammalian poly(A)-specific 3'-exoribonuclease," The Journal of biological chemistiy, 272(16):10448-56, Apr. 1997.
Korner et al., "The deadenylating nuclease (DAN) is involved in poly(A) tail removal during the meiotic maturation of Xenopus oocytes," EMBO J., 17(18):5427-37, Sep. 1998.
Kunkel, "Rapid and efficient site-specific mutagenesis without phenotypic selection," Proc. Natl. Acad. Sci. USA 82(2): 488-492, Jan. 1985.
LaCava et al., "RNA degradation by the exosome is promoted by a nuclear polyadenylation complex," Cell, 121(5):713-24, Jun. 2005.
Langmead and Salzberg, "Fast gapped-read alignment with Bowtie 2," Nat. Methods, 9(4):357-9, Mar. 2012.
Lee et al., "The PARN deadenylase targets a discrete set of mRNAs for decay and regulates cell motility in mouse myoblasts," PLoS Genet, 8(8):e1002901, 2012.
MacBeath and Schreiber, "Printing proteins as microarrays for high-throughput function determination," Science, 289(5485):1760-1763, Sep. 2000.
Magoc and Salzberg, "FLASH: fast length adjustment of short reads to improve genome assemblies," Bioinformatics, 27(21):2957-63, Nov. 2011.
Maher, "DNA triple-helix formation: an approach to artificial gene repressors?," Bioassays. 14(12):807-15, Dec. 1992.
Mason and Bessler, "mRNA deadenylation and telomere disease," J. Clin. Invest, 125(5):1796-8. May 2015.
McLaughlin et al., "Adeno-associated virus general transduction vectors: analysis of proviral structures," J. Virol., 62(6):1963-1973, Jun. 1989.

(56) References Cited

OTHER PUBLICATIONS

Meuli et al., "Efficient gene expression in skin wound sites following local plasmid injection," J. Invest. Dermatol., 116(1):131-135, Jan. 2001.
Miller, "Progress toward human gene therapy," Blood, 76(2):271-8, Jul. 1990.
Miranda et al., "Nucleic acids within urinary exosomes/microvesicles are potential biomarkers for renal disease," Kidney International, 78(2):191-199, Jul. 2010.
Mitchell et al., "A box H/ACA small nucleolar RNA-like domain at the human telomerase RNA 3' end," Molecular and cellular biology, 19(1):567-76, Jan. 1999.
Mitchell et al., "A telomerase component is defective in the human disease dyskeratosis congenita," Nature, 402:551-5, Dec. 1999.
Moon et al., "Poly (A)-Specific Ribonuclease (PARN) Mediates 3 [Prime]-End Maturation of the Telomerase RNA Component," Nature Genetics, Dec. 2015, 47: 1482-1488.
Muzyczka, "Use of adeno-associated virus as a general transduction vector for mammalian cells," Curr. Top. Microl. Immunol., 158:97-129, 1992.
Narang et al., "Improved phosphotriester method for the synthesis of gene fragments," Meth. Enzymol., 68:90-8, 1997.
Nordstrom et al., "Direct analysis of single-nucleotide polymorphism on double-stranded DNA by pyrosequencing," Biotechnol. Appl. Biochem., 31(2):107-112, Apr. 2000.
Ogel and McPherson, "Efficient deletion mutagenesis by PCR," Protein Engineer, 5(5):467-468, Jul. 1992.
Parikh and Guengerich, "Random mutagenesis by whole-plasmid PCR amplification," BioTech., 24(3):428-431, Mar. 1998.
Park et al., "Generation of human-induced pluripotent stem cells," Nat. Protoc., 3(7):1180-6, 2008.
Park et al., "Reprogramming of human somatic cells to pluripotency with defined factors," Nature, 451(7175):141-6, Jan. 2008.
Patro et al., "Salmon: accurate, versatile and ultrafast quantification from RNA-seq data using lightweight-alignment," bioRxiv, 1:021592, Jan. 2015.
Pfaffe et al., "Diagnostic potential of saliva: current state and future applications," Clin. Chem., 57(5):675-687, May 2011.
Phillips et al., "Rapid point-of-care breath test for biomarkers of breast cancer and abnormal mammograms," PLOS One., 9(3):e90226, Mar. 2014.
Pons et al., "PCR site-directed mutagenesis using Pyrococcus sp GB-D polymerase coupled to a rapid screening procedure. Application to a beta-glucanase gene," Meth. Molec. Biol., 67:209-218, 1997.
Rammelt et al., "PAPD5, a noncanonical poly(A) polymerase with an unusual RNA-binding motif," RNA, 17(9):1737-46, Sep. 2011.
Ranjan et al., "Aminoglycoside binding to Oxytricha nova telomeric DNA," Biochemistry, 49(45):9891-903, Oct. 2010.
Ray and Nickoloff, "Site-specific mutagenesis of almost any plasmid using a PCR-based version of unique site elimination," BioTech., 13(3):342-346, Sep. 1992.
Rhem and Hancock, "Membrane topology of the outer membrane protein OprH from Pseudomonas aeruginosa: PCR-mediated site-directed insertion and deletion mutagenesis," J. Bacteriol. 178(11):3346-3349, Jun. 1996.
Rosenfeld et al., "Adenovirus-mediated transfer of a recombinant alpha 1-antitrypsin gene to the lung epithelium in vivo," Science, 252(5004):431-434, Apr. 1991.
Rosenfeld et al., "In vivo transfer of the human cystic fibrosis transmembrane conductance regulator gene to the airway epithelium," Cell, 68(1):143-155, Jan. 1992.
Samulski et al., "Helper-free stocks of recombinant adeno-associated viruses: normal integration does not require viral gene expression," J. Virol. 63(9):3822-3828, Sep. 1989.
Schmidt and Butler, "Nuclear RNA surveillance: role of TRAMP in controlling exosome specificity," Wiley Interdiscip Rev RNA 4(2):217-31, Mar. 2013.
Shukla and Parker, "PARN modulates Y RNA stability and its 3'-end formation," Molecular and cellular biology, 37(20):e00264-17, Oct. 2017.
Soder et al., "Amplification, increased dosage and in situ expression of the telomerase RNA gene in human cancer," Oncogene 14(9):1013-21, Mar. 1997.
Soerensen et al., "Genetic variation in TERT and TERC and human leukocyte telomere length and longevity: a cross-sectional and longitudinal analysis," Aging Cell, 11(2):223-7, Apr. 2012.
Stuart et al., "Exome sequencing links mutations in PARN and RTEL1 with familial pulmonary fibrosis and telomere shortening," Nat. Genet., 47(5):512-7, May 2015.
Summerton, "Morpholino antisense oligomers: the case for an RNase H-independent structural type," Biochim. Biophys. Acta., 1489(1):141-58, Dec. 1999.
Tam et al., "Stabilized plasmid-lipid particles for systemic gene therapy," Gene Ther., 7(21):1867-74, Nov. 2000.
Taylor and Gercel, "The origin, function, and diagnostic potential of RNA within extracellular vesicles present in human biological fluids," Front. Genet., 4:142, Jul. 2013.
Tessier and Thomas, "PCR-assisted mutagenesis for site-directed insertion/deletion of large DNA segments," Meths. Molec. Biol., 57:229-237, 1996.
Trapp et al., "A virus-encoded telomerase RNA promotes malignant T cell lymphomagenesis," The Journal of experimental medicine, 203(5):1307-17, May 2006.
Tratschin et al., "A human parvovirus, adeno-associated virus, as a eucaryotic vector: transient expression and encapsidation of the procaryotic gene for chloramphenicol acetyltransferase," Mol. Cell. Biol., 4(10):2072-2081, Oct. 1984.
Tratschin et al., "Adeno-associated virus vector for high-frequency integration, expression, and rescue of genes in mammalian cells," Mol. Cell. Biol., 5(11):3251-3260, Nov. 1985.
Tratschin et al., "Genetic analysis of adeno-associated virus: properties of deletion mutants constructed in vitro and evidence for an adeno-associated virus replication function," J. Virol., 51(3):611-619, Sep. 1984.
Tsakiri et al., "Adult-onset pulmonary fibrosis caused by mutations in telomerase," Proc. Natl. Acad. Sci. U.S.A., 104(18):7552-7, May 2007.
Tummala et al., "Poly(A)-specific ribonuclease deficiency impacts telomere biology and causes dyskeratosis congenita," J. Clin. Invest, 125(5):2151-60, May 2015.
van Beusechem et al., "Long-term expression of human adenosine deaminase in rhesus monkeys transplanted with retrovirus-infected bone-marrow cells," Proc. Natl. Acad. Sci. U.S.A., 89(16):7640-7644, Aug. 1992.
Venteicher et al., "A human telomerase holoenzyme protein required for Cajal body localization and telomere synthesis," Science, 323(5914):644-8, Jan. 2009.
Virtanen et al., "Poly(A)-specific ribonuclease (PARN): an allosterically regulated, processive and mRNA cap-interacting deadenylase," Crit. Rev. Biochem. Mol. Biol., 48(2):192-209, Mar. 2013.
Vulliamy et al., "Mutations in the telomerase component NHP2 cause the premature ageing syndrome dyskeratosis congenita," Proc. Natl. Acad. Sci. U.S.A., 105(23):8073-8, Jun. 2008.
Vulliamy et al., "The RNA component of telomerase is mutated in autosomal dominant dyskeratosis congenita," Nature, 413(6854):432-5, Sep. 2001.
Walne et al., "Genetic heterogeneity in autosomal recessive dyskeratosis congenita with one subtype due to mutations in the telomerase-associated protein NOP10," Human molecular genetics, 16(13):1619-29, Jul. 2007.
Wang and Malcolm, "Two-stage PCR protocol allowing introduction of multiple mutations, deletions and insertions using QuikChange Site-Directed Mutagenesis," BioTech., 26(4):680-682, Apr. 1999.
Wang and Wilkinson, "Site-directed mutagenesis of large (13-kb) plasmids in a single-PCR procedure," Biotech., 29(5):976-978, Nov. 2000.
Wang et al., "Multiple mutant cDNAs from one reaction mixture using asymmetric primers in PCR," BioTech., 19(4): 556-559, Oct. 1995.

(56) References Cited

OTHER PUBLICATIONS

Warlich et al., "Lentiviral vector design and imaging approaches to visualize the early stages of cellular reprogramming," Mol. Ther., 19(4):782-9, Apr. 2011.

Westin et al., "Telomere restoration and extension of proliferative lifespan in dyskeratosis congenita fibroblasts," Aging Cell, 6(3):383-94, Jun. 2007.

Wilson et al., "Retrovirus-mediated transduction of adult hepatocytes," Proc. Natl. Acad. Sci. U.S.A., 85(9):3014-3018, May 1988.

Wondisford et al., "Cloning of the human thyrotropin beta-subunit gene and transient expression of biologically active human thyrotropin after gene transfection," Mol. Endocrinol., 2(1):32-39, Jan. 1988.

Wong and Collins, "Telomerase RNA level limits telomere maintenance in X-linked dyskeratosis congenita," Genes Dev., 20(20):2848-58, Oct. 2006.

Xu and Gong, "Adaptation of inverse PCR to generate an internal deletion," BioTech., 26(4):639-641, Apr. 1999.

Yamaguchi et al., "Mutations of the human telomerase RNA gene (TERC) in aplastic anemia and myelodysplastic syndrome," Blood, 102(3):916-8, 2003.

Yang et al., "Detection of tumor cell-specific mRNA and protein in exosome-like microvesicles frombloodand saliva," PLOS One, 9(11):e110641, Nov. 2014.

Yasun et al., "Enrichment and detection of rare proteins with aptamer-conjugated gold nanorods," Anal. Chem., 84(14):6008-6015, Jun. 2012.

Yoda et al., "Poly(A)-specific ribonuclease mediates 3'-end trimming of Argonaute2-cleaved precursor microRNAs," Cell Rep., 5(3):715-26, Nov. 2013.

Zaug et al., "Method for determining RNA 3' ends and application to human telomerase RNA," Nucleic acids research, 24:532-3, Feb. 1996.

Zhang and Madden, "PowerBLAST: a new network BLAST application for interactive or automated sequence analysis and annotation," Genome Res., 7(6):649-656, Jun. 1997.

EP European Search Report in European Appln. No. 16856437.5, dated May 11, 2020, 8 pages.

EP Office Action by European Appln. No. 16856437.5. dated Feb. 26, 2021, 6 pages.

Stuart et al., "Exome sequencing links mutations in PARN and RTEL1 with familial pulmonary fibrosis and telomere shortening," Nature Genetics, May 4, 2015, 47(5):512-7.

* cited by examiner

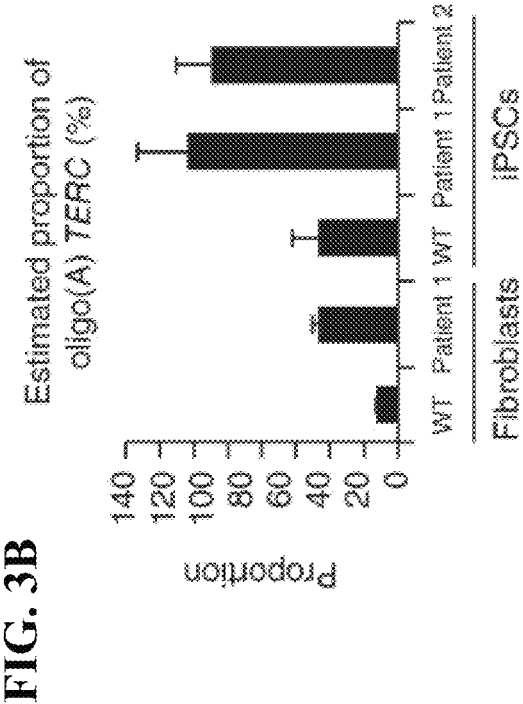
FIG. 3A
FIG. 3B
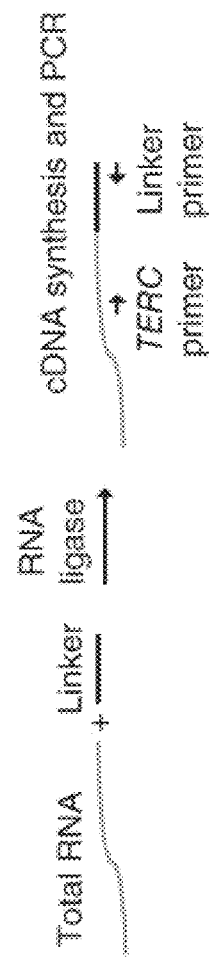
FIG. 3C
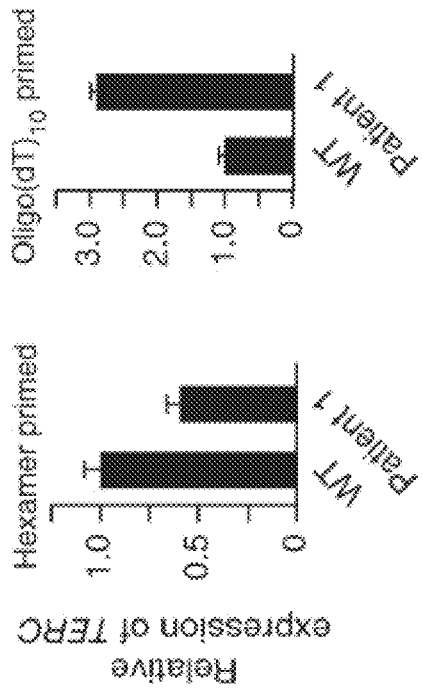
FIG. 3D
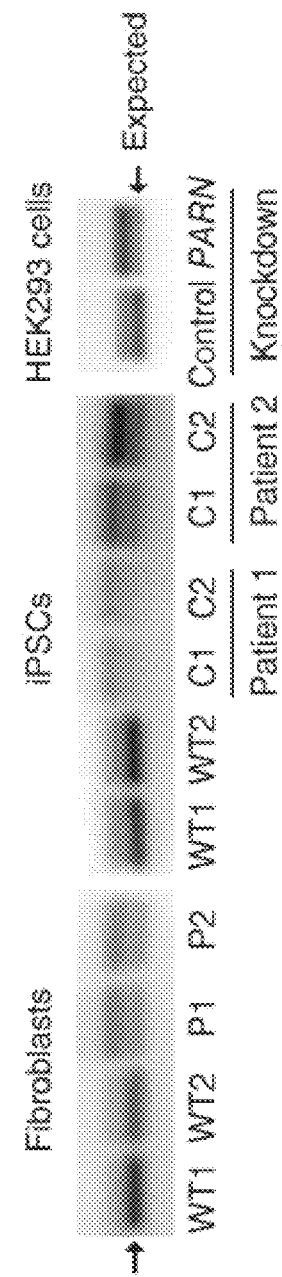

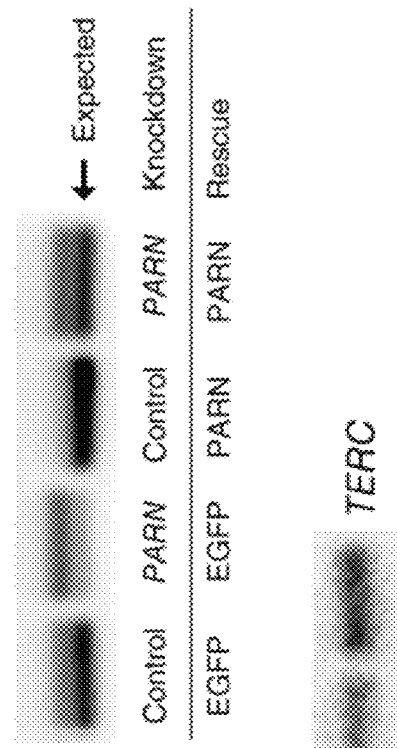
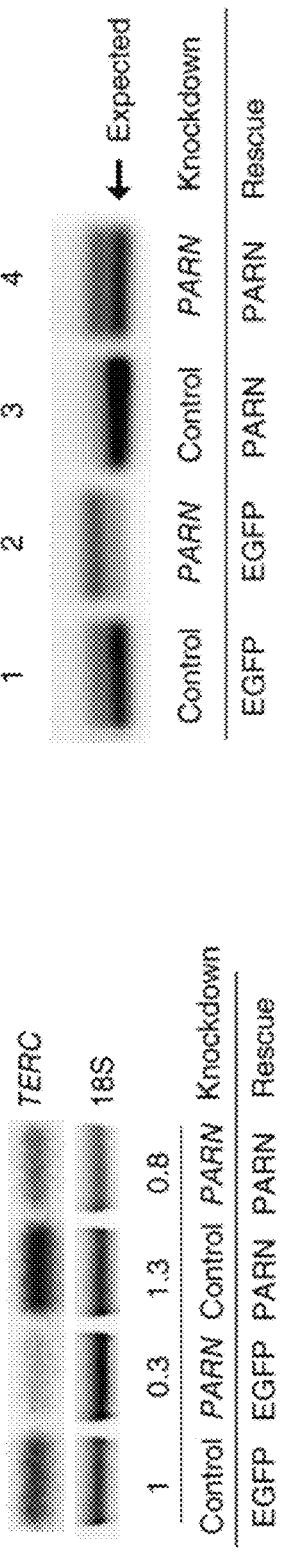
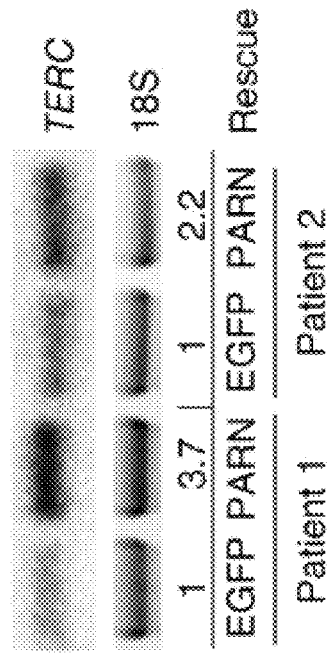
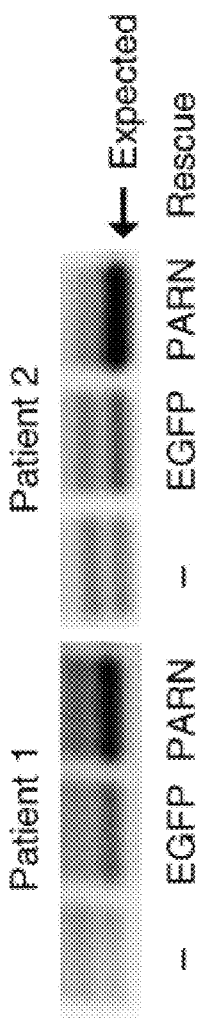
FIG. 6A
FIG. 6B
FIG. 6C
FIG. 6D

3' RACE strategy

FIG. 11B

3' RACE TERC PCR amplicons

FIG. 11C

Deep sequencing of TERC RNA ends

FIG. 11D

TERC oligoadenylation

PARN (NM_002582) SEQ ID NO: 1

```
aggcgcgcgc tgtttccgga agtcgcggcc ggcgtcaccg ctgcggctgc ctcagctact gccgcagtcg
ccgcggaatt cggcgagtag aaccgctgag gcgggcgcgg gccgggtgg ggccaaggtt ccggccactc
tgcagaatgg agataatcag gagcaatttt aagagtaatc ttcacaaagt gtaccaggcc atagaggagg
ccgacttctt cgccatcgat ggggagtttt caggaaacag tgatggacct tcagtctctg cattaacaaa
tggttttgac actccagaag agaggtatca gaagcttaaa aagcattcca tggactttt gctatttcag
tttggccttt gcactttaa gtatgactac acagattcaa agtatataac gaagtcattt aacttctatg
ttttcccgaa acccttcaat agatcctcac cagatgtcaa atttgttttgt cagagctcca gcattgactt
tctagcaagc cagggatttg attttaataa agttttttcga aatgaaattc catatttaaa tcaggaagaa
gaaagacagt taagagagca gtatgatgaa aaacgttcac aggcgaatgg tgcaggagct ctgtcctatg
tatctcctaa cacttcaaaa tgtcctgtca cgattcctga ggatcaaaag aagtttattg accaagtggt
agagaaaata gaggatttat tacaaagtga agaaaacaag aacttggatt tagagcatg taccgggtc
caaagaaaac taatttatca gactttgagc tggaagtatc cgaaaggcat tcatgttgag actttagaaa
ctgaaaagaa ggagcgatat atagttatca gcaaagtaga tgaagaagaa cgcaaaagaa gagagcagca
gaaacatgcc aaagaacagg aggagctgaa tgatgctgtg ggattttcta gagtcattca cgccattgct
aattcggaa aacttgttat tggacacaat atgtcttgg acgtcatgca cacagttcat cagttctact
gccctctgcc tgcggactta agtgagttta aagagatgac aacatgtgtt ttcccagac tcttggatac
taaattgatg gccagcacac aaccttttaa ggatatcatt aacaacacat cccttgcgga attggaaaag
cggttaaaag agacacecttt caaccctcct aaagttgaaa gtgccgaagg ttttccaagt tatgacacag
cctctgaaca actccacgag gcaggctacg atgcctacat cacagggctg tgcttcatct ccatgccaa
ttacctaggt tctttctca gcctccaaa aattcatgtg tctgccagat caaaactcat tgaaccttt
tttaacaagt tatttcttat gagggtcatg gatatccct atctaaactt ggaaggacca gacttgcagc
ctaaacgtga tcatgttctc catgtgacat tcccaaaga atggaaaacc agcgaccttt accagcttt
cagtgccttt ggtaacattc agatatcctg gattgatgac acatcagcat ttgttttccct tagccagcc
gagcaagtaa agattgctgt caataccagc aaatatgcag aaagctatcg gatccaaacc tatgctgaat
atatggggaa aaaacaggaa gagaagcaga tcaaagaaga gtggactgaa gatacctgga aggaggctga
cagcaaacgg ttaaacccccc agtgcatacc ctacaccctg cagaatcact attaccgcaa caatagtttt
acagctccca gcacagtagg aaagagaaat ttgagtccta gtcaagagga agctggcctg gaggacgag
tgtcagggga gatttccgac actgagcttg agcagaccga ttcctgtgca gagccctct cagagggaag
gaaaaaggcc aagaaattaa aaagaatgaa gaaggagctt tctccagcag gaagcatctc gaagaacagc
cctgccacac tctttgaagt tcctgacaca tggtaaccaa gacctgaggg cagcaaacg ctggtgctgt
cgctgtgagc aagagccggc tggcacattt ggaagccgca ctgtatttaa cttaatcaaa tgtggtatgg
gaggggttgg aaacaagtt gtctcctggg ggagaaaa caggtttat ttttgtggct gtggttttt
cccctttta atctaactgc ctgttgacat tgacactcat cacggttgta ggctgtcatg aatgtgtacg
tgcttaacca gtgaattccg tgttgctctt gtgaggcctt tcctgtcatg acccagtgtg cttaagaacc
tgcctgatgg ggagtgtcgg ctgtgaaatc tgcaaaaga gctgacattc cagtgctgt gatcatgaat
ttggggggt actgtcctgc ctgtgcatct tctcgcactg agattttgag gcagttgcag ccctcggtta
gtctcccagt ggaaaaatcg gttgtgcctc cctgcttccc accatagctg cctgaaaaca tgacgctctc
aagcttgtcc ttccttcagg aagatgtcca ctcatgccca cccatgagag ggcttgccgt atgccctggc
ctttgggcat atttatgtag agttcctttc tcctaagacg tgagtttctc atggggatg tacgagtaaa
aaggttaact tctgttctta tgcctggcgc tgtgttcact ttccagagtc tctgttcgtt tgtttggatg
gcgtctcgg ggtacggcag cgtgtgtgcg tacgtgtctg tgtgtgtgtg tgtgtgtg tgtgtgtgt
tgtgtgtgtg tgtgtgaaat cgtgcaaatc tacaacatgt cccagcccat tctccgttga aacagatcac
agcaacgaca aacgctcatg gcgctgcttt gctccacccg cttcagatag atcattgtta gatatttcac
atttttgtat ggtggaaata aaaatgaaaa atgtatttcc aaaagatgaa aattaaaaac attttcatag
gac
```

FIG. 27

PARN (O95453-1) SEQ ID NO: 96

```
          10         20         30         40         50
    MEIIRSNFKS NLHKVYQAIE EADFFAIDGE FSGISDGPSV SALTNGFDTP
          60         70         80         90        100
    EERYQKLKKH SMDFLLFQFG LCTFKYDYTD SKYITKSFNF YVFPKPFNRS
         110        120        130        140        150
    SPDVKFVCQS SSIDFLASQG FDFNKVFRNG IPYLNQEEER QLREQYDEKR
         160        170        180        190        200
    SQANGAGALS YVSPNTSKCP VTIPEDQKKF IDQVVEKIED LLQSEENKNL
         210        220        230        240        250
    DLEPCTGFQR KLIYQTLSWK YPKGIHVETL ETEKKERYIV ISKVDEEERK
         260        270        280        290        300
    RREQQKHAKE QEELNDAVGF SRVIHAIANS GKLVIGHNML LDVMHTVHQF
         310        320        330        340        350
    YCPLPADLSE FKEMTTCVFP RLLDTKLMAS TQPFKDIINN TSLAELEKRL
         360        370        380        390        400
    KETPFNPPKV ESAEGFPSYD TASEQLHEAG YDAYITGLCF ISMANYLGSF
         410        420        430        440        450
    LSPPKIHVSA RSKLIEPFFN KLFLMRVMDI PYLNLEGPDL QPKRDHVLHV
         460        470        480        490        500
    TFPKEWKTSD LYQLFSAFGN IQISWIDDTS AFVSLSQPEQ VKIAVNTSKY
         510        520        530        540        550
    AESYRIQTYA EYMGRKQEEK QIKRKWTEDS WKEADSKRLN PQCIPYTLQN
         560        570        580        590        600
    HYYRNNSFTA PSTVGKRNLS PSQEEAGLED GVSGEISDTE LEQTDSCAEP
         610        620        630
    LSEGRKKAKK LKRMKKELSP AGSISKNSPA TLFEVPDTW
```

FIG. 28

PAPD5 (TRF4-2) (NM_001040284) SEQ ID NO: 2

```
   1 acaacgcgct ccctgcgggg cgggcggcaa cctccatgcg gcctcgtcca cgctcagcac
  61 cggggaagcc gaggcggaga agccgcgcgc gcctcagaag ctcccggacg cccagcggcg
 121 gcgcgagcgg cggcggcggc agcagcagca gcagcagcac ggccaccggc gggagcggca
 181 gcagcaccgg cagccccggc ggcgcggcct cggccccggc cccggccccg gccggcatgt
 241 atcgctccgg ggagcgcctg ctgggcagcc acgcgctgcc cgcggagcag cgggacttcc
 301 tgcccctaga gacgaccaac aacaacaaca accaccacca gcccggggcc tgggcccgcc
 361 gggcgggctc ctcggcgtcc tcgcctccct cggcgtcctc gtcccgcac ccttcggccg
 421 ccgtccccgc cgccgatcca gccgattcgg cctcgggcag cagcaacaag aggaagcgcg
 481 acaacaaggc cagcacgtat ggactcaact acagcctgct gcagcccagc ggagggcggg
 541 ccgcgggggg cggccgagca gacggcggcg gggtcgtgta cagcgggacc ccgtggaaac
 601 ggaggaacta caaccaggga gtcgtgggtc tgcatgaaga aatcagtgat ttttatgaat
 661 acatgtctcc aagacctgag gaggagaaga tgcggatgga ggtggtgaac aggatcgaga
 721 gtgtaattaa ggagctctgg cccagcgctg acgtccagat atttggaagt tttaaaactg
 781 gactttattt acctactagt gacatcgacc tagtggtgtt tgggaagtgg agaacctac
 841 ccctctggac tctggaagaa gctcttcgga acacaaagt cgcagatgag gattcggtga
 901 aagttttaga caaagcaact gtacctatta ttaaattaac agattctttt actgaagtga
 961 aagttgatat cagctttaat gtacagaatg gcgtgagagc agctgacctc atcaaagatt
1021 ttaccaagaa atatcctgta ttgccatact tggttttagt attgaaacaa ttcctattgc
1081 agagggacct taatgaagta tttacaggtg gaattggttc ttatagtctc tttttaatgg
1141 cagtcagttt ccttcagtta catcccaggg aagatgcttg catcccaat acaaactatg
1201 gtgttctctt aatagaattt tttgaattat atggacgaca cttcaattat taaagactg
1261 gcatccggat aaaggatggt ggttcatatg tggccaaaga tgaagtacag aaaaatatgc
1321 tagatggcta caggccatca atgctttata tcgaagatcc tttacaacca ggtaacgatg
1381 ttggaaggag ttcatatggg gccatgcaag tgaagcaggc ctttgattat gcctacgttg
1441 ttttgagtca tgctgtatca ccaatagcaa agtactatcc caacaatgaa acagaaagca
1501 tactaggtag aataattgaa gtaacagatg aagttgccac atatagagat tggatatcaa
1561 agcagtgggg cttgaagaat agacctgagc cttcatgcaa tggaaatggt gttaccttga
1621 tagtagatac tcagcagtta gataaatgta ataataatct atctgaagaa atgaagccc
1681 ttggaaaatg tagaagtaaa acctcggaat ctcttagtaa acactcttca aactcttcat
1741 caggtccagt gtcgtcctct tctgccacac agtccagctc tagtgatgta gattccgatg
1801 caacaccatg caaaaccccg aaacagctgc tttgccgtcc gtccactggg aaccgagtag
1861 ggtcgcaaga tgtatccttg gagtcctctc aggcagttgg gaaaatgcaa agcacccaaa
1921 ccactaacac atccaacagc accaacaaat ctcagcatgg atcagcaagg ctcttcgtt
1981 cttccagcaa aggcttccaa ggtacaactc aaacaagcca tggttccttg atgacaaaca
2041 aacaacatca aggcaaatcc aataatcagt attaccatgg caaaaagagg aaacacaaga
2101 gggacgcgcc cctctcagac ctctgtagat agtcagcgct gcgcggtgga ctgtcttctc
2161 tgtgcaatga tctcatgctc aggacagttg cgcaggact cctgggagat attcaggagc
2221 ctcacactgt tcagacgttg acttagcaac tgcgtttttt cccagctcgc cacagaatgg
2281 atcatgaaga ctgacaactg caaaaaaac aaaacaaaac aaaaaaaaaa gcaagcaaaa
2341 aagagggaaa aaaaaggctg cttatttgat aagtcatatg ctacaacagg gtcattttaa
2401 gatttaaagc ttgaatgtaa aataaatata tttctcattg gctttatgca gagttatagg
2461 gaatagtatt cagtgttggt agggtgatag aaacaaaaaa cagtatcaga ggatgaggtg
2521 gggaaggaaa acaaaggtat ctgataggaa gtccagattc caaggggaa agtgatctgt
2581 gcatgttttt tttttaaata ttttgcata tatttaccat tttattgtgt gtatatatag
2641 aagaccatat aggagattga tatttgtaat agtggatttg ttaataatac ttttttacata
2701 acattactgt ttaaattgta aacagatttt ttctcaggat tagtttgaaa ataatctaa
2761 attgtcatct taacatccat atataggga gtgattagtt ctattactca atttgttttt
2821 ctcagcattg aaatgactta atagaaccct tgtgtcctgc tgcaaaaatt tttcctctct
2881 aaagaaaagg tttatggtgg caaatgatgt ttattttatt ttgtaaaaaa aaaaaatgt
2941 actatgtact tttgtgtaaa cactgaaaaa tctctggtca tctccgagaa ttaacttgca
```

FIG. 29

```
3001 actgttttct atagtgctgt cgtcttgggc aatgggcaat tacatgactt tgtgtttgct
3061 tcctttgcag tctttttttt ttcccccat ttcttcctaa taggaaaaaa aaaaaaaaaa
3121 aggtcaccca tgtctggtct cattcctgtt gcagtgaaac ttcgagttcc acagactttg
3181 catgctggct tctctaaccc tgtgtgctgc gtgtgcctgt ttctcatctc ttattctttt
3241 taaaattcat gcttaactac tgtgggagaa taactgtaaa cagctttaat taaatcatac
3301 ttataaaaaa ctatttttctt atattccact ctatgctttt ggtattgttg atctttacaa
3361 attaaatggt ctttgataat ggatctattt tgtattgcct tattaagacc aaatacttct
3421 tgtcatccca ttctttatcc tcttctttca tggaattgtt atcgttaatt aaaactttt
3481 taaacattgg cttgtttcaa tcatactgta aattttggtt gtagtcagct ttgagtgcaa
3541 tgagatgtat aattctgtta tcattacctg ttgagtttga aactcagttg ggaatattta
3601 atataataga atgtaagtga catttctgaa aatgctttct ttcagggtga aagctcttat
3661 gtttagcatc aatgtgtatg gctctgttaa atgcagccat ttctgagacg agattctttt
3721 atatatatat acatataaag tactattggc ttttaggagt ttctttata tacatttatg
3781 aaatactgaa gaccaatcag accattaatg gacacttagt gtaactttt ataagaaaa
3841 taatgctaaa gtaagaccaa aactgatgtc atcactgaaa ttaacaattt tcaatatgtt
3901 catatttttaa ttcacaatgg aaaaatgtgt tccaaaactg gaaactcata gtactcgtgt
3961 aaactgtgga agatttcaaa tgtgatgtta ttttgacaat gttttaaatt ttagagtcac
4021 attttattct gatcagaatt tttattgaga tgttgagctt ttgtttttga aactagtttg
4081 tcataacatt gtgcataatc acagtattta ttttctagga caattgtgaa tgtgtagact
4141 tatgtttact gctaagggaa caattattta taaaataata ttaaatccag tattagctgc
4201 ctatttcaga cacttaatac ttgcagagat ctatgttaca tttaccacac tgaagttttt
4261 tttgttgttt tttgtttgtt tttaaagaat caccctcatt gttgaaagta aatgtactct
4321 tagggtgcga atattagtgt tccaataagc atgtgattat attaaggtgg tggtagcggg
4381 aagataattc tgattccatt gggaatctta ggttttcgta aattattgg gaaaatagtt
4441 tttcctgtac tgctgaagtt tctttttggt aaacagtatc tttctaaaag aaaaaagcat
4501 gaaggagaaa ttgaggtgtg tatacatttc ctcaaatgac cagcattgta ttcgtgaata
4561 ctgtgtatct tgcagtgaac agtgtggaag ctgttcattt ttcaatctga agtaaaatac
4621 tttcaagaac ttttagtttg cctgctcatt tgttttatac atttcatcta tttgactcct
4681 atcttatttc tttttgagt tttaatactt cctatatttt gtgaatatat cagaaatgtg
4741 tcatttatat attagagtcc attcatatcc atgaatcata accttccttt gctaatactt
4801 gttgaatggg atttttacaaa ttctccctca ctctggtgac atttctcagg cagtcatgta
4861 tgtgtacctg gccattagaa atattaatat ttaaagactg ttttttagag gagctgatgg
4921 gttggtgagg tgtcagcaca aaatcttact ggttatgttt tgatgataaa agtatatcca
4981 ttttttccct ccagctttaa ggtgactgtg aaggtgcctg gttttgaatg tctttgtttg
5041 gtttggagat gtcgcactca gttttcaaat ctagcttgga tctgtaggac ctatgttttt
5101 tacaagtaat tgccctccag tcttcaacag ttgattctgt tttatttta tcctgttttg
5161 agtgtacttt accttttactt gcatttgag cctcattaat atttaggtta tttgatttgg
5221 ctccagatat tcctagatct gcacagggca aaacatgggc tataggtgta gcatttttaa
5281 ttgtctttt ctgctggaac cttatatctc tccatgtgtt ttctgctcct tccctccccc
5341 atgaaatggt aagtgtgact tgtgtttgcc tgaacctgtg gactagtgtt tggggttttct
5401 ggaaacacta gagggtcaga aaagagtaat gaccaccgtg acgtgcagga ttctcttgct
5461 gtgacatgtt cattgcaaag ccctctccag tgactaggag gtgtagttat taaggttgat
5521 ctgttagaaa tcaccattat taggtattag tggtagatgt tgctgatact tttattggtc
5581 atgactacat ctcagttttta ctttaatatt gatctatagt ttgatcagtt ccttgaattc
5641 taatatgttg atttctcagt gtttctgtca ctaaccaaga atgtttctag gcagttggtt
5701 gcttcacagt caaaactaaa tggtaaacta tcaaaaatac attcccaatt ttgctgtgat
5761 aaatattgaa atgttaaaat taatgaacag aagaatttat tcttacccat ctattcttgt
5821 tctcctagtt cattaaactt tcagttattg gaaaggcaca ttctcaaagt attttatgag
5881 caaaatattc tataaatgcg tctaacaaac ctaattgaat ataaagtta tatttagtag
5941 ttactgttga tagtaatttt catcagggtc atagttcatc tagtaaaata tttagagaat
```

FIG. 29 (Continued)

```
6001 gatgttaaca ttccagcatt aaagtgggaa caaagattta tatatgaaat tccttaaaag
6061 agttcatctt gccttggttt ctgaccctca agactctagc tacctgccat cttgtcaaaa
6121 catttgtggg tagaataagt gttaaagatc aaattttaat atgcttctcg atatttaaca
6181 tagctaagaa gccagatttt actgtagaag ttatttacat gatttgaaaa cttgacctaa
6241 ctggaagcct ttttctcagt catcttgttc taagccatct tgacttcaca cccttagcga
6301 cttttctttt tttttggtc aaagataatg agctaaatat atatagacgt tgaatgttga
6361 caaaattatt aaccagaaaa attgcttata aaggctgctg atctatttga tacctagaat
6421 taaatatttg aggacagttt ttagttaata aactgctaat gtttatttta ctgtctctca
6481 ggttttggt tttttaaaa aaaatgtgtt tggcctttac attttctact taagtgtgta
6541 ctttattgag tttaaccttg tctgtagcct agtagcctga aagaaaagga gacagaacca
6601 gagagatgga tgtagtgcat tccctttggt tattacacat ttgtggtagc tcctggattt
6661 actgagagat attttagcta tgtcaataag aacagctaat gatgtggaaa tcaggtgttc
6721 tcttgtgtat ttcagtgaac attttattta gtagttgcat atcatctcta gttccacatt
6781 ttaacttaac gtctttgtgg cttcaccact gagctacctt tcactacacc agcttctgtg
6841 tggcctggta acatggaagg tctctcctaa ggacagtctg gacgtatttt gggggaatgt
6901 tatttatctt aaagatgcct agaaacaaaa cgcatatagt accagtgaga aactatgaag
6961 taaacaagtt gctcaggccg ggcatggtgg ctcacgcctg taatcccagc actttgggag
7021 gccgaagcgg gaggatggct tgaggctggg agtttgagac cttcatctct taaaaaaaca
7081 aacaaaaacc tgaatggtga ggtgtggtgg aattgggtag gggagggaaa ggaggacttg
7141 gaaaagcatt ctccaaagcc agcaacttgg tgaagttcag tacttgcctc ttagaggtta
7201 ggccatgcct ttcaaagaga gtgaaatgat gggttatcag ccacattctt ggagttaata
7261 ttttcttca tctttcagtt tgggttctgt gctattcata gttcttccct aagaccattt
7321 cattattacc ttttatattt agttgcaatt tattataata tgttgttttg tccctgaact
7381 taatctccta attttaagat cctctctgat ttttgcatat tgaaacttac agaagtcact
7441 ttaaaaaagt cttttgaaag tcctacaatc ctaaaataaa tcacaagctt gtttgttaga
7501 cgtgtcaaga gtctccagtc tttactacta aaaagcagca ctgccttaac acacattgtt
7561 atgggtgaaa agtgagggac gaccagtgta gtttctggat ataaagtgtg aaggactgtt
7621 gagttaaaca ttttagtgg aatatacata gataacgtgt atttagaaac tttggtgaag
7681 ccagtatttg tttttagtaa cctttttatg tatttccttc tttgattagc attgtcttca
7741 gtgttaagaa atgtggactc ctgtgaggtg ctggaggttt gaatcatctt gaaactttc
7801 caatcttgtc tagttaccac tgcagagaca ctaaggaatt taccagaaaa agatatttga
7861 tacaagtgat ttaagaaatc tcaacatttc ctgaggccgt atcactgggc aaccagtgat
7921 gaaaactatg aatgaattgc acctggaa gatttttaa gctaatgaca gtttcttcaa
7981 agatgtcaat tatttgcctt ggaaatttta taaattgcat ttctatgcac atcggcctct
8041 agtgcttacc actcggttta ttattcataa tctgcaattc aataaaggct ttgtgttttc
8101 atttatcttc aaaa
```

PAPD5 (TRF4-2) (Q8NDF8-1) (SEQ ID NO: 97)

```
         10         20         30         40         50
MYRSGERLLG SHALPAEQRD FLPLETTNNN NNHHQPGAWA RRAGSSASSP
         60         70         80         90        100
PSAESSPHPS AAVPAADPAD SASGSSNKRK RDNKASGGPA AGGGRADGGG
        110        120        130        140        150
VVYSGTPWKR RNYNQGVVGL HEEISDFYEY MSPRPEEEKM RMEVVNRIES
        160        170        180        190        200
VIKELWPSAD VQIFGSFKTG LYLPTSDIDL VVFGKWENLP LWTLEEALRK
        210        220        230        240        250
HKVADEDSVK VLDKATVPII KLTDSFTEVK VDISFNVQNG VRAADLIKDF
        260        270        280        290        300
TKKYPVLPYL VLVLKQFLLQ RDLNEVFTGG IGSYSLFLMA VSFLQLHPRE
        310        320        330        340        350
DACIPNTNYG VLLIEFFELY GRHFNYLKTG IRIKDGGSYV AKDEVQKNML
        360        370        380        390        400
DGYRPSMLYI EDPLQPGNDV GRSSYGAMQV KQAFDYAYVV LSHAVSPIAK
        410        420        430        440        450
YYPNNETESI LGRIIRVTDE VATYRDWISK QWGLKNRPEP SCNGPVSSSS
        460        470        480        490        500
ATQSSSSDVD SDATPCKTPK QLLCRPSTGN RVGSQDVSLE SSQAVGKMQS
        510        520        530        540        550
TQTTNTSNST NKSQHGSARL FRSSSKGPQG TTQTSHGSLM TNKQHQGKSN
        560        570
NQYYHGKKRK HKRDAPLSDL CR
```

FIG. 30

MODULATORS OF TELOMERE DISEASE

CLAIM OF PRIORITY

This application is a 371 U.S. National Phase Application of PCT/US2016/057409, filed Oct. 17, 2016, which claims the benefit of U.S. Provisional Application Ser. No. 62/242,970, filed on Oct. 16, 2015, U.S. Provisional Application Ser. No. 62/308,427, filed on Mar. 15, 2016, and PCT Application PCT/US16/57229 filed on Oct. 14, 2016. The entire contents of the foregoing are incorporated herein by reference.

FEDERALLY SPONSORED RESEARCH OR DEVELOPMENT

This invention was made with Government support under Grant No. R01 DK107716-01 and T32 HL007574 awarded by the National Institutes of Health. The Government has certain rights in the invention.

TECHNICAL FIELD

The disclosure relates to treating and diagnosing telomere diseases.

BACKGROUND

A telomere is a region of repetitive nucleotide sequences at each end of a chromosome, which protects the end of the chromosome from deterioration or from fusion with neighboring chromosomes. The length of a telomere is a key determinant of cellular self-renewal capacity. The telomerase ribonucleoprotein maintains telomere length in tissue stem cells, and its function is critical for human health and longevity.

Short telomeres, due to genetic or acquired insults, cause a loss of cellular self-renewal and result in life-threatening diseases, for which there are few if any effective medical therapies. In these diseases involving short telomeres, e.g., aplastic anemia, pulmonary fibrosis, hepatic cirrhosis, bone marrow failure, etc., there is an unmet clinical need for new therapies.

SUMMARY

The disclosure is based, in part, on the discovery that poly(A) ribonuclease (PARN) mutations can result in the accumulation of 3' oligo-adenylated forms of nascent Telomerase RNA Component (TERC) RNA transcripts, which are targeted for destruction, thus causing telomerase deficiency and telomere diseases, and disruption of the non-canonical poly(A) polymerase PAP Associated Domain Containing 5 (PAPD5; also known as Topoisomerase-related function protein 4-2 (TRF4-2)) restores TERC levels, telomerase activity, and telomere elongation in PARN-mutant patient cells.

In one aspect, the disclosure relates to methods of treating a disorder associated with telomerase dysfunction in a subject. The methods include the steps of identifying the subject as having a disorder associated with telomerase dysfunction; and administering to the subject an effective amount of a pharmaceutical composition comprising an agent that decreases the level or activity of PAP Associated Domain Containing 5 (PAPD5), thereby treating the disorder associated with telomerase dysfunction in the subject.

In some embodiments, the disorder associated with telomerase dysfunction is dyskeratosis congenital, aplastic anemia, pulmonary fibrosis, idiopathic pulmonary fibrosis, hematological disorder, or hepatic disease.

In some embodiments, the agent increases the level or activity of telomerase RNA component (TERC).

In some embodiments, the agent can be a PAPD5 inhibitor.

In some embodiments, the agent is an anti-PAPD5 antibody or anti-PAPD5 antibody fragment. The agent can also be an antisense molecule or a small interfering nucleic acid which is specific for a nucleic acid encoding PAPD5.

In some embodiments, the agent is a shRNA. The shRNA can have a sequence that is selected from the group of SEQ ID NOs: 79-83.

In some embodiments, the agent is an aminoglycoside or a nucleoside analogue.

The agent can be a vector comprising guide RNAs (gRNAs) that target PAPD5 for CRISPR/Cas9, wherein CRISPR/Cas9 creates null mutations in PAPD5, thereby decreasing the level of PAPD5. The guide RNA can have a sequence that is selected from the group of SEQ ID NO: 84, 86, and 88.

In some embodiments, the agent includes a fusion protein or a nucleic acid encoding the fusion protein, wherein the fusion protein comprises an DNA-binding domain that binds to PAPD5, and a catalytic domain, wherein the catalytic domain decreases the expression level of PAPD5.

In some embodiments, the methods further include the steps of administering to the subject an agent that increases the level or activity of Poly(A) specific ribonuclease (PARN).

The present disclosure also provides methods of treating a disorder associated with telomerase dysfunction in a subject. The methods include the steps of identifying the subject as having a disorder associated with telomerase dysfunction; and administering to the subject an effective amount of a pharmaceutical composition comprising an agent that increases the level or activity of PARN, thereby treating the disorder associated with telomerase dysfunction in the subject. The disorder associated with telomerase dysfunction can be dyskeratosis congenital, aplastic anemia, pulmonary fibrosis, idiopathic pulmonary fibrosis, hematological disorder, or hepatic disease.

In some embodiments, the agent increases the level or activity of TERC. The agent can be a nucleic acid comprising a nucleotide sequence that encodes PARN.

In some embodiments, the agent includes a fusion protein or a nucleic acid encoding the fusion protein, wherein the fusion protein comprises an DNA-binding domain that targets PARN, and a catalytic domain, wherein the catalytic domain increases the expression level of PARN.

In some embodiments, the methods further include the step of administering to the subject an agent that decreases the level or activity of PAPD5.

In another aspect, the disclosure provides methods of treating cancer in a subject. The methods include the steps of identifying the subject as having a cancer; and administering to the subject an effective amount of a pharmaceutical composition comprising an agent that increases the level or activity of PAPD5, thereby treating the cancer in the subject.

In some embodiments, the agent decreases the level or activity of TERC.

In some embodiments, the agent is a nucleic acid comprising a nucleotide sequence that encodes PAPD5.

In some embodiments, the agent includes a fusion protein or a nucleic acid encoding the fusion protein, wherein the fusion protein comprises an DNA-binding domain that binds to PAPD5, and a catalytic domain, wherein the catalytic domain increases the expression level of PAPD5.

In some embodiments, the methods further include the step of administering to the subject an agent that decreases the level or activity of PARN.

In some embodiments, the agent that decreases the level or activity of PARN is an anti-PARN antibody or anti-PARN antibody fragment.

In some embodiments, the agent that decreases the level or activity of PARN is an antisense molecule or a small interfering nucleic acid which is specific for a nucleic acid encoding PARN.

In some embodiments, the agent that decreases the level or activity of PARN is a shRNA. The shRNA can have a sequence that is selected from the group of SEQ ID NO: 74 and SEQ ID NO: 75.

In some embodiments, the agent that decreases the level or activity of PARN is an aminoglycoside or a nucleoside analogue.

In some embodiments, the agent that decreases the level or activity of PARN is a vector comprising guide RNAs (gRNAs) that targets PARN, wherein CRISPR/Cas9 creates null mutations in PARN, thereby decreasing the level of PARN. The gRNA that targets PARN can have a sequence that is selected from the group of SEQ ID NOs: 90, 92, and 94.

The present disclosure also provides methods of treating a subject having a disorder associated with telomerase dysfunction. The methods include the steps of identifying the subject as having a mutation at PARN; and administering to the subject an effective amount of a pharmaceutical composition that alters the level or activity of Telomerase RNA Component (TERC), thereby treating the disorder associated with telomerase dysfunction in the subject.

The mutation can be a deletion in PARN. In some embodiments, the amino acid residue at position 87 of PARN in the subject is not serine. In some embodiments, the amino acid residue at position 7 of PARN in the subject is not asparagine.

In some embodiments, the pharmaceutical composition has a nucleotide acid that encodes PARN.

In some embodiments, the pharmaceutical composition includes clustered regularly interspaced short palindromic repeats (CRISPR) associated protein 9 (Cas9) protein, or DNA or RNA encoding Cas9; a guide RNA that target PARN locus, or a vector that encodes guide RNA; and a nucleic acid sequence that encodes PARN without the mutation.

The present disclosure also provides methods of identifying an agent for modulating the level or activity of TERC. The methods include the steps of contacting a cell with a test agent; determining the level or activity of TERC in the cell; comparing the level or activity of TERC in the cell to a reference level or activity; and identifying the test agent as an agent that modulates the level or activity of TERC if the level or activity of TERC in the cell is significantly different from the reference level or activity.

In some embodiments, the reference level or activity is the level or activity of TERC in a cell that has not been treated with the test agent.

In some embodiments, the test agent is a nucleic acid, a vector comprising a nucleic acid, a small molecule, an antibody, an antibody fragment, an aminoglycoside, or a nucleoside analogue.

In some embodiments, the agent is a modulator of PARN, or a modulator of PAPD5.

In some embodiments, the cell is an induced pluripotent stem (iPS) cell or a primary human cell. In some embodiments, the cell is derived from skin, bone marrow, or blood. In some embodiments, the cell is derived from a subject having or suspected of having a disorder associated with telomerase dysfunction. The disorder associated with telomerase dysfunction can be dyskeratosis congenital, aplastic anemia, pulmonary fibrosis, idiopathic pulmonary fibrosis, hematological disorder, or hepatic disease.

In another aspect, the disclosure provides methods of identifying a candidate agent for modulating the level or activity of TERC. The methods include the steps of contacting a cell with a test agent; determining that the test agent modulates the level or activity of PARN or PAPD5; and identifying the test agent as a candidate agent that modulates the level or activity of TERC.

In some embodiments, the test agent is a nucleic acid, a vector comprising a nucleic acid, a small molecule, an antibody, an antibody fragment, an aminoglycoside or a nucleoside analogue.

In some embodiments, the test agent binds to PARN or binds to PAPD5.

In some embodiments, the cell is an induced pluripotent stem (iPS) cell or a primary human cell. In some embodiments, the cell is derived from skin, bone marrow, or blood. The cell can also be derived from a subject having or suspected of having a disorder associated with telomerase dysfunction. The disorder associated with telomerase dysfunction can be dyskeratosis congenital, aplastic anemia, pulmonary fibrosis, idiopathic pulmonary fibrosis, hematological disorder, or hepatic disease.

In one aspect, the disclosure provides methods of identifying a subject as having a disorder associated with telomerase dysfunction. The methods include the steps of determining the level or activity of TERC, PARN, or PAPD5 in a cell from the subject;

comparing the level or activity of TERC, PARN, or PAPD5 to the reference level or reference activity of TERC, PARN, or PAPD5, respectively; and identifying the subject as having a disorder associated with telomerase dysfunction if the level or activity of TERC, PARN, or PAPD5 is significantly different from the reference level or activity of TERC, PARN, or PAPD5, respectively.

The disorder associated with telomerase dysfunction can be, e.g., dyskeratosis congenital, aplastic anemia, pulmonary fibrosis, idiopathic pulmonary fibrosis, hematological disorder, or hepatic disease.

The level or activity of TERC is determined by the level of TERC RNA in the cell, by the telomere size in the cell, and/or by the telomerase activity in the cell.

In another aspect, the disclosure provides methods of treating a subject having a disorder associated with telomerase dysfunction. The methods include the steps of identifying the subject as having a mutation at PARN; and treating the subject for the disorder associated with telomerase dysfunction.

The disorder associated with telomerase dysfunction can be dyskeratosis congenital, aplastic anemia, pulmonary fibrosis, idiopathic pulmonary fibrosis, hematological disorder, or hepatic disease.

In some embodiments, the mutation is a deletion in PARN. In some embodiments, the amino acid residue at position 87 of PARN in the subject is not serine. In some embodiments, the amino acid residue at position 7 of PARN in the subject is not asparagine.

The present disclosure also provides methods of killing or inhibiting the proliferation of a cancer cell. The methods include the steps of contacting the cancer cell with an effective amount of an agent that increases the level or activity of PAPD5, thereby killing or inhibiting the proliferation of the cancer cell.

In some embodiments, the agent decreases the level or activity of TERC.

In some embodiments, the agent is a nucleic acid comprising a nucleotide sequence that encodes PAPD5.

In some embodiments, the agent includes a fusion protein or a nucleic acid encoding the fusion protein, wherein the fusion protein comprises an DNA-binding domain that binds to PAPD5, and a catalytic domain, wherein the catalytic domain increases the expression level of PAPD5.

In some embodiments, the methods further include the step of contacting the cancer cell with an agent that decreases the level or activity of PARN. The agent that decreases the level or activity of PARN can be an anti-PARN antibody, anti-PARN antibody fragment, an antisense molecule or a small interfering nucleic acid which is specific for a nucleic acid encoding PARN.

In some embodiments, the agent that decreases the level or activity of PARN is a shRNA. The shRNA can have a sequence that is selected from the group of SEQ ID NO: 74 and SEQ ID NO: 75.

In some embodiments, the agent that decreases the level or activity of PARN is an aminoglycoside or a nucleoside analogue.

In some embodiments, the agent that decreases the level or activity of PARN is a vector comprising guide RNAs (gRNAs) that targets PARN, wherein CRISPR/Cas9 creates null mutations in PARN, thereby decreasing the level of PARN. The gRNA can have a sequence that is selected from the group of SEQ ID NOs: 90, 92, and 94.

In some embodiments, the aminoglycoside is kanamycin B sulfate, pramycin sulfate, spectinomycin dihydrochloride pentahydrate, ribostamycin sulfate, sisomicin sulfate, amikacin disulfide, dihydrostreptomycin sesquisulfate, hygromycin B, netilmicin sulfate, paromomycin sulfate, kasugamycin, neomycin, gentamicin, tobramycin sulfate, streptomycin sulfate, or neomycin B.

In one aspect, the disclosure relates to methods of treating a disorder associated with aging in a subject, or at least one symptom associated with such a disorder. The methods include the steps of identifying the subject as having a disorder associated with aging; and administering to the subject an effective amount of a pharmaceutical composition comprising an agent that decreases the level or activity of PAP Associated Domain Containing 5 (PAPD5), thereby treating the disorder associated with aging, or at least one symptom associated with such a disorder, in the subject.

In some embodiments, the disorder associated with aging is macular degeneration, diabetes mellitus, osteoarthritis, rheumatoid arthritis, sarcopenia, cardiovascular disease, hypertension, atherosclerosis, coronary artery disease, ischemia/reperfusion injury, cancer, premature death, or age-related decline in cognitive function, cardiopulmonary function, muscle strength, vision, or hearing.

In some embodiments, the disorder associated with aging is a neurodegenerative disorder.

In some embodiment, the agent increases the level or activity of telomerase RNA component (TERC). In some embodiments, the agent is a PAPD5 inhibitor.

In some embodiments, the agent is an anti-PAPD5 antibody or anti-PAPD5 antibody fragment.

In some embodiments, the agent is an antisense molecule or a small interfering nucleic acid which is specific for a nucleic acid encoding PAPD5.

In some embodiments, the agent is a shRNA. In some embodiments, the shRNA can have a sequence that is selected from the group of SEQ ID NOs: 79-83.

In some embodiments, the agent is an aminoglycoside or a nucleoside analogue.

In some embodiments, the agent is a vector including guide RNAs (gRNAs) that target PAPD5 for CRISPR/Cas9, wherein CRISPR/Cas9 creates null mutations in PAPD5, thereby decreasing the level of PAPD5.

In some embodiments, the guide RNA has a sequence that is selected from the group of SEQ ID NO: 84, 86, and 88.

In some embodiments, the agent includes a fusion protein or a nucleic acid encoding the fusion protein, wherein the fusion protein comprises an DNA-binding domain that binds to PAPD5, and a catalytic domain, wherein the catalytic domain decreases the expression level of PAPD5.

In some embodiments, the methods further include the step of administering to the subject an agent that increases the level or activity of Poly(A) specific ribonuclease (PARN).

In one aspect, the disclosure relates to methods of treating a disorder associated with aging, or at least one symptom associated with such a disorder, in a subject. The methods include the steps of identifying the subject as having a disorder associated with aging; and administering to the subject an effective amount of a pharmaceutical composition comprising an agent that increases the level or activity of PARN, thereby treating the disorder associated with aging, or at least one symptom associated with such a disorder, in the subject.

In some embodiments, the disorder associated with aging is macular degeneration, diabetes mellitus, osteoarthritis, rheumatoid arthritis, sarcopenia, cardiovascular disease, hypertension, atherosclerosis, coronary artery disease, ischemia/reperfusion injury, cancer, premature death, age-related decline in cognitive function, cardiopulmonary function, muscle strength, vision, or hearing.

In some embodiments, the disorder associated with aging is a neurodegenerative disorder.

In some embodiments, the agent increases the level or activity of TERC.

In some embodiments, the agent is a nucleic acid having a nucleotide sequence that encodes PARN.

In some embodiments, the agent includes a fusion protein or a nucleic acid encoding the fusion protein, wherein the fusion protein comprises an DNA-binding domain that targets PARN, and a catalytic domain, wherein the catalytic domain increases the expression level of PARN.

In some embodiments, the methods further include the step of administering to the subject an agent that decreases the level or activity of PAPD5.

In one aspect the present disclosure provides a method of identifying a candidate compound for the treatment of telomere disease. In some embodiments, the method comprises providing a first isolated cell; contacting it with a test compound to determine Telomerase RNA Component (TERC) levels in the cell; comparing the TERC level in the cell to a reference level; to then select a candidate compound that is associated with altered TERC level. In some embodiments, the test compound is a nucleic acid. In some embodiments, the test compound is a vector comprising a nucleic acid. In some embodiments, the test compound is a nucleic acid that encodes an RNA. In some embodiments, the test compound is a nucleic acid that encodes a fusion protein. In some embodiments, the test compound is a small molecule. In some embodiments, the cell is contacted with a test compound comprising a nucleic acid encoding a specific protein, e.g., PARN. In some embodiments, the cell is contacted with a test compound comprising a nucleic acid encoding a specific protein, e.g., TRF4-2 (also known as PAPD5). In yet other instances, the test compound is a vector comprising a nucleic acid and the cell is contacted with the vector construct comprising a nucleic acid.

In some embodiments, the test compound can be a test nucleic acid, e.g., short hairpin RNA. In some embodiments, the test compound is a small molecule, e.g., modulates TRF4-2.

In some embodiments, the test compound is an isolated cDNA fragment e.g., PARN cDNA. In some embodiments, the test compound modulates topoisomerase-related function protein 4-2 (TRF4-2). In some embodiments, the test compound can bind to TRF4-2. In some embodiments, the test compound modulates TERC activity. In yet other instances, the modulation by the test compound is at the level of gene expression, e.g., TERC. In yet other instances, the modulation is at the level of activity, e.g., telomerase activity. Modulation by the test compound can be at the level of protein expression, e.g., telomerase, TERC, TRF4-2 or PARN. Modulation by the test compound can be at the level of telomere size or maturity.

Modulation by the test compound can be at the level of altering telomere ends. In some embodiments, a test compound contacted with an isolated cell, can also be used to identify a candidate compound to treat a patient.

In some embodiments, the test compound modulates mature TERC species. In some embodiments, test compounds can alter specific RNA species, e.g., TERC, but not a housekeeping gene.

In some embodiments, a test compound can be administered in a high dose. The subject can be a patient or a cell isolated from a patient having a disease. In some embodiments, the test compound is administered to a iPS cell. In some embodiments, the test compound is administered to a iPS cell derived from patient's skin. In some embodiments, the test compound is administered to a iPS cell derived from patient's tumor.

In some embodiments, the test compound modulates TERC levels in the IPS cells. In some embodiments, the test compound modulates telomerase activity and also modulates telomere size. In some embodiments, the test compound promotes accumulation of mature RNA, e.g., TERC. In some embodiments, test compounds can alter specific RNA species, e.g., TERC, but not a housekeeping gene.

In some embodiments, the cell is an isolated human cell. In some embodiments, the cell is derived from a patient's skin. In some embodiments, the isolated human cell is derived from a patient's bone marrow. In some embodiments, the cell is an isolated human cell and is derived from a patient's blood.

In some embodiments, the cell used to contact a compound is an isolated human cell that is derived from a patient having telomere disease. In some embodiments, the patient is suspected of having telomere disease. In some embodiments, the patient has symptoms of aplastic anemia. In some embodiments, the patient is diagnosed as having telomere deficiency.

In some embodiments, the patient has a mutation of a locus, e.g., PARN locus. In some embodiments, the patient has a deletion in a locus, e.g., PARN. In some embodiments, the patient has symptoms of hepatic cirrhosis.

In some embodiments, the patient has symptoms of pulmonary fibrosis. In some embodiments, the patient has dyskeratosis congenita (DC). In some embodiments, the cell is isolated from a patient having or suspected of having a hematological disorder. In some embodiments, the isolated cell is from a patient having or suspected of having dyskeratosis congenita. In some embodiments, the isolated cell is screened in the presence of a test compound comprising at least one of the following agents: a nucleic acid, a small molecule or an antibody. In some embodiments, the test compound is a vector.

Vectors include viral vectors and can comprise nucleic acid. Exemplary vectors also include plasmid vectors that comprise nucleic acids that encode proteins, e.g., PARN.

In some embodiments, the method of screening can be performed in an isolated cell, e.g., human cell, obtained from a patient having or suspected of having a hematological disorder.

In some embodiments, the methods disclosed herein also involve identifying compounds that treat telomere deficiency. In some embodiments, the method comprises a primary human cell isolated from a patient who has an altered poly(A)-specific ribonuclease locus. An instant method also includes contacting the isolated cell, e.g., an iPS cell, with a compound that modulates telomere size.

In some embodiments, the method includes a comparison of an altered level or activity of Topoisomerase-Related Function Protein 4-2 (TRF4-2) in a human cell to determine the TRF4-2 protein expression. In some embodiments, the test compound that alters the level of TRF4-2 can be a small molecule. In some embodiments, the test compound can be a modulator of TRF4-2 binding. In some embodiments, the cell can be a fibroblast cell. In some embodiments, the cell can be any human cells, e.g., tumor cell. The cell can be isolated from a patient and converted to an iPS cell. In some embodiments, an iPS cell is used to contact a test compound to detect TERC levels in the cells. The test compound modulates by inhibition or by increasing expression, e.g., RNA or protein. The expression or activity of a RNA, e.g., TERC can be modulated by using a test compound that inhibits TRF4-2. In some embodiments, the compound used to contact a cell, also alters TERC processing. In some embodiments, the compound that alters TRF4-2 in a cell, also alters mature TERC levels in the cell. The compound can be an inhibitory nucleic acid, e.g., shRNA or an isolated cDNA e.g., PARN cDNA. In some embodiments, the compound can alter specifically TRF4-2 RNA, without altering any housekeeping RNA e.g., beta actin or GAPDH. In some embodiments, the compound can alter specifically PARN RNA/protein levels, without altering any housekeeping RNA, e.g., beta actin or GAPDH. Exemplary test compounds can be vector constructs, e.g., viral vector comprising a nucleic acid encoding a protein.

In one aspect, the present disclosure relates to methods for identifying a candidate compound for altering telomerase activity. In some embodiments, the method includes a cell with PARN deficiency, e.g., human cell with a PARN gene alteration. In some embodiments, the cell can be an iPS cell. In some embodiments, the cell can be obtained from a human tissue, e.g., a tumor. In some embodiments, the method includes a cell that is contacted with a nucleic acid comprising poly(A)-specific ribonuclease. In some embodiments, the levels of TERC and PARN in the cells are low at baseline. In some embodiments, the nucleic acid increases the level of PARN mRNA and protein. In some embodiments, the nucleic acid increases the level of TERC. In some embodiments, the nucleic acid comprising poly(A)-specific ribonuclease is an inhibitory nucleic acid that reduces the level of PARN protein. In some embodiments, the test compound alters the level or activity of poly(A)-specific ribonuclease in a human cell isolated from a patient who is suspected of having a telomere disease.

In one aspect, the invention discloses methods of identifying a subject as having telomere disease. The method comprises as a first step, a means to determine a level of Telomerase RNA Component (TERC) in the cell e.g., by gene expression. In some embodiments, the cell obtained from the patient is an iPS cell.

The methods further include comparing the level of Telomerase RNA Component (TERC) in an isolated cell to a reference level; to essentially identify a subject who has a level of TERC below the reference level, as having telomere disease.

In some embodiments, determining the level of TERC comprises determining the level of TERC RNA in the cell. In some embodiments, determining the level of TERC comprises determining the telomere size in the cell. In another instance, determining the level of TERC comprises determining the telomerase activity in the cell.

The disclosure also provides methods of treating a patient having telomere disease. The method can comprise administering to the patient an effective amount of a nucleic acid that alters the level or activity of Poly(A)-specific Ribonuclease (PARN) in an amount sufficient to alter Telomerase RNA Component (TERC) levels or telomerase activity in the patient. This method includes steps to treat the telomere disease. The steps include a treatment step. In some embodiments, the composition used in treatment is a small molecule. In some embodiments, the composition is a nucleic acid. In some embodiments, the composition comprises a nucleic acid that encodes a fusion-protein. In some embodiments, the composition is a nucleic acid that encodes an RNA. In some embodiments, the composition comprises a small molecule that binds TRF4-2. In some embodiments, the composition includes a small molecule that binds PARN.

In yet another aspect, the disclosure provides methods of treating a patient having telomere disease, the method comprising administering to a patient an effective amount of a composition that alters the level or activity of Topoisomerase-Related Function Protein 4-2 (TRF4-2) in an amount sufficient to alter Telomerase RNA Component (TERC) levels or telomerase activity in the patient; to thereby treat the telomere disease. In some embodiments, the composition can be a small molecule. In some embodiments, the composition comprises a small molecule that binds TRF4-2. In some embodiments, the composition includes a small molecule that binds PARN. In some embodiments, the composition is a nucleic acid. In some embodiments, the nucleic acid encodes a fusion-protein. In some embodiments, the composition is a nucleic acid. In some embodiments, the telomere disease is aplastic anemia. In some embodiments, the telomere disease is dyskeratosis congenita. In some embodiments, the telomere disease is pulmonary fibrosis or hepatic disease. In some embodiments, the composition includes a small molecule that binds TRF4-2. In some embodiments, the composition includes a small molecule that binds PARN. In some embodiments, the nucleic acid comprises an RNA.

In some embodiments, the method of treatment can comprise administering to the patient an RNA that alters TERC levels.

Also disclosed herein are methods of treating cancer in a patient. The method comprises administering to the patient a composition. In some embodiments, the composition can be a modulator of the level or activity of Poly(A)-specific Ribonuclease (PARN). In some embodiments, the composition can be a modulator of the level or activity of topoisomerase-related function protein 4-2 (TRF4-2). In some embodiments, the composition can be a modulator of the level or activity of TERC RNA. In some instance the compound alters telomere size. In some embodiments, the compound is administered in an amount sufficient to alter Telomerase RNA Component (TERC) levels in the patient, to thereby treat the cancer. In some embodiments, the compound alters telomere size. In some embodiments, the compound is administered in an amount sufficient to alter TRF4-2 levels in the patient, to thereby treat the cancer.

In one aspect, the present disclosure relates to methods of treating cancer in a patient. The method comprises administering to the patient a composition comprising a modulator of the level or activity of topoisomerase-related function protein 4-2 (TRF4-2) in an amount sufficient to alter Telomerase RNA Component (TERC) levels or telomerase activity in the patient, to thereby treat the cancer. In some embodiments, the composition includes a modulator that alters telomerase activity. In some embodiments, the cancer is a hematological cancer. In some embodiments, the composition includes a small molecule or a nucleic acid modulator that does not alter all RNA species. In some embodiments, the composition includes a small molecule or a nucleic acid modulator that specifically alters RNA species. In some embodiments, the RNA is a non-coding RNA, e.g., TERC.

The disclosure also provides methods of identifying a candidate compound for treating cancer. The methods include steps of providing a tumor cell from a patient having cancer and contacting the tumor cell with a test compound. The methods further include steps of determining telomere size in the tumor cell in the presence of the test compound and comparing telomere size in the tumor cell to a reference level. The methods also include selecting a test compound as a candidate compound that alters telomere size in the tumor cell.

The present disclosure also provides methods of identifying a candidate compound for treating cancer. In some embodiments, the method includes the following steps: providing an isolated cell from a tumor, providing the cell from a patient having cancer in a system whereby it is contacted with a test compound; determining telomerase activity in the tumor cell in the presence of the test compound; comparing the activity of telomerase in the tumor cell to a reference level; selecting a test compound as a candidate compound if the test compound alters telomerase activity in the tumor cell. In some embodiments, the test compound is a nucleic acid, and the cell is contacted with a vector comprising the nucleic acid. In some embodiments, the test compound is a modulator of the level or activity of topoisomerase-related function protein 4-2 (TRF4-2). In some embodiments, the test compound is a modulator of the level or activity of poly(A)-specific ribonuclease (PARN). In some embodiments, the test compound is small molecule. In some embodiments, the test compound is a nucleic acid encoding a fusion protein, and the tumor cell is contacted with a vector comprising the nucleic acid. In some embodiments, the test compound is an expression vector comprising a nucleic acid encoding a fusion protein, and the cell is contacted with the expression vector.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

The entire content of each of these files is hereby incorporated by reference.

DESCRIPTION OF DRAWINGS

FIG. 3A is a bar graph showing a quantitative PCR (qPCR) of TERC transcripts in cDNA from normal (WT) and patient fibroblasts, using hexamer-versus oligo(dT)10-priming.

FIG. 3B is a bar graph showing estimated proportion of oligo(A) TERC forms in fibroblasts and iPS cells (n=2).

FIG. 3C is a schematic diagram showing a 3' RACE strategy using PCR using linker- and TERC-specific primers.

FIG. 3D is a photograph showing agarose gel analysis of the 3' RACE products from normal and patient (Pt) fibroblasts (left) and iPS clones (cl; middle), and 293 cells subjected to shRNA-mediated knockdown of PARN versus luciferase (ctrl) (right).

FIG. 6A is a photograph showing a Northern blot of TERC RNA from 293 cells transduced with lentivirus encoding shRNA directed against PARN versus luciferase (ctrl), and then rescued with lentivirus expressing PARN versus EGFP as a control.

FIG. 6B is a photograph showing 3'RACE products from 293 cells subjected to shRNA-mediated knockdown of PARN versus luciferase, and rescued with PARN versus EGFP, separated by agarose gel electrophoresis.

FIG. 6C is a photograph showing a Northern blot of TERC RNA from patient fibroblasts transduced with lentivirus encoding PARN versus EGFP control.

FIG. 6D is a graph showing 3'RACE products from PARN mutant patient fibroblasts cells rescued with lentivirus expressing PARN versus EGFP.

FIG. 10B is a photograph of Southern blot showing TRF length analysis in PARN knockdown HEK293 cells stably transduced with lentivirus encoding TERC versus control (ctrl).

FIG. 10C is a graph showing TRF length analysis of immortalized, PARN-mutant patient fibroblasts stably transduced with lentivirus encoding TERC versus control.

FIG. 11A is a schematic diagram showing strategy for 3' rapid amplification of cDNA ends (RACE).

FIG. 11B is a photograph of agarose gel electrophoresis showing 3' RACE TERC products from HEK 293 cells transduced with lentivirus encoding shRNA against PAPD5, PARN or luciferase (ctrl).

FIG. 11C is a graph showing 3' RACE PCR products that were subjected to deep sequencing and aligned to the TERC gene. The sequenced products include AUGCAGUUCGCUA$_n$ (SEQ ID NO: 100), AUGCAGUUCGCA$_n$ (SEQ ID NO: 101), AUGCAGUUCGA$_n$ (SEQ ID NO: 102), AUGCAGUUCA$_n$ (SEQ ID NO: 103), AUGCAGUUA$_n$, AUGCAGUA$_n$, AUGCAGA$_n$, AUGCAA$_n$, and AUGCA$_n$. (A)$_n$ is oligo (A)$_n$.

FIG. 11D is a bar graph showing oligo(An) species as a proportion of total reads in control versus PAPD5 knockdown cells. The A-tail length in nucleotides (nt) averaged over the population of oligo(An) species is indicated.

FIG. 27 shows an exemplary nucleotide sequence of PARN (accession no. NM_002582).

FIG. 28 shows an exemplary amino acid sequence of PARN (accession no. 095453).

FIG. 29 shows an exemplary nucleotide sequence of PAPD5 (TRF4-2) (accession number NM_001040284).

FIG. 30 shows an exemplary amino acid sequence of PAPD5 (TRF4-2) (accession number Q8NDF8).

DETAILED DESCRIPTION

Figure 1A:
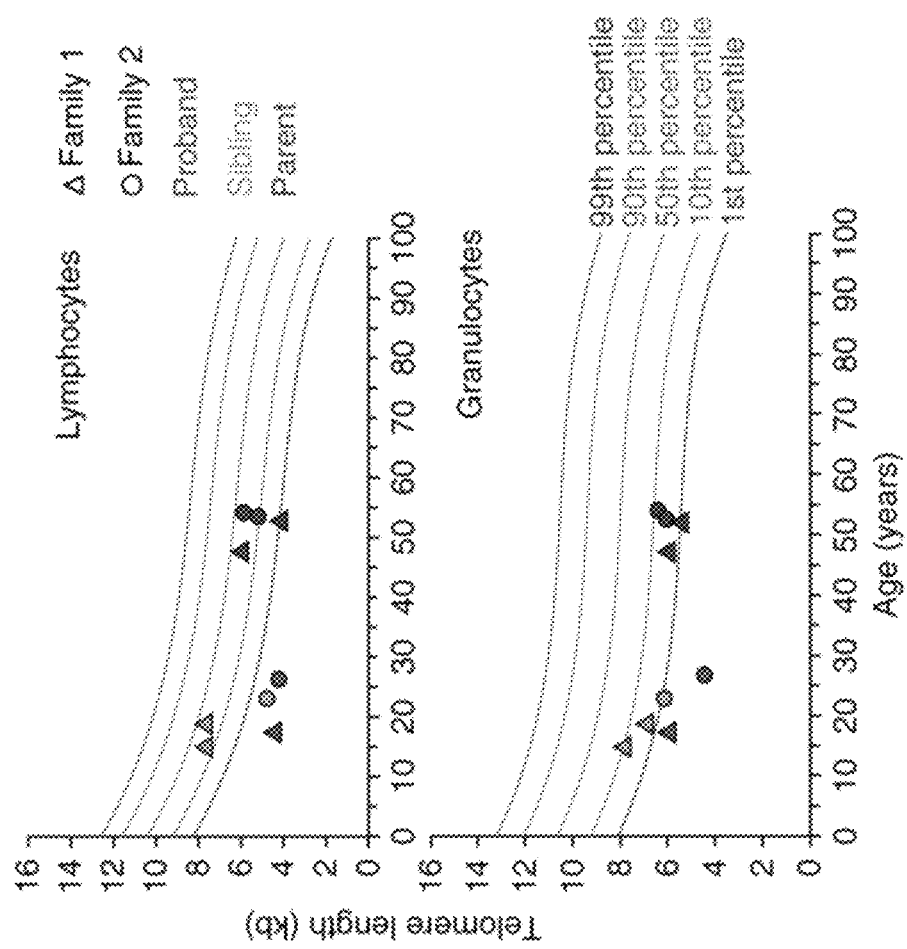
FIG. 1A is a schematic diagram showing segregation analysis of compound heterozygous PARN mutations in patient families 1 and 2.

A telomere is a region of repetitive nucleotide sequences at each end of a chromosome. For vertebrates, the sequence of nucleotides in telomeres is TTAGGG. In humans, this sequence of TTAGGG is repeated approximately 2,500 times. Telomerase is a ribonucleoprotein that adds the telomere repeat sequence to the 3' end of telomeres. Cells with impaired telomerase function often have limited capacity for self-renewal, i.e., an abnormal state or condition characterized by an inability of cells (e.g., stem cells) to divide sufficiently. This deficiency in cells can, for example, lead to various diseases and disorders. The present disclosure provides, among other things, methods of screening for agents that modulate TERC levels and activity. Also provided are methods of diagnosing patients and methods of treating patients having telomere disease.

Telomere Disease

The term "telomere disease," "telomere syndrome" or "disorder associated with telomerase dysfunction" refers to a disorder associated with abnormal telomeres. They include, but are not limited to, dyskeratosis congenital (DC), Revesz syndrome, Hoyeraal-Hreidarrson syndrome, Coats plus syndrome, and some forms of inherited aplastic anemia/myelodysplastic syndrome, aplastic anemia, pulmonary fibrosis, idiopathic pulmonary fibrosis, bone marrow failure, hematological disorder, hepatic disease (e.g., chronic liver disease, and hepatic cirrhosis) etc. Telomere diseases also include those affecting the blood and immune systems, lungs, liver, skin, mucosal surfaces, bones, cardiovascular system, endocrine system, and/or gastrointestinal system, as cells with the impaired self-renewal capacity can affect the normal function of organs or systems. Some of these disorders include aplastic anemia, pulmonary fibrosis, hepatic cirrhosis, osteoporosis and osteonecrosis, vascular malformations, diabetes, primary immunodeficiency, and inflammatory bowel disease. This group of diseases is often associated with a cellular state marked with decreased self-renewal capacity that can be attributed to an alteration in telomere length. Thus, the term "telomere deficiency" as used herein refers to a cellular state in the body, including stem cells, induced pluripotent cells and fibroblasts, and is often marked by a perturbation in expression or activity of an enzyme that is involved in regulating telomere size. As used herein, the term "telomerase dysfunction" refers to abnormal levels or function of telomerase in a cell or patient.

For example, telomerase dysfunction can include telomerase deficiency, such as where telomerase levels are lower than normal due to excess or unwanted telomerase degradation, and telomerase over-activity, such as where telomerase levels are higher than normal due to deficient telomerase degradation.

Telomere diseases or disorders associated with telomerase dysfunction are typically associated with changes in the size of telomere. Many proteins and RNA components are involved in the telomere regulatory pathway, including TERC, PARN and PAPD5 (also known as TRF4-2). This disclosure provides how these proteins or RNA components work in the regulatory pathway and how they are related to telomere diseases. Also provided are methods of screening agents that modulate these proteins or RNA components.

Among these telomere diseases, dyskeratosis congenita (DC) is a rare, progressive bone marrow failure syndrome characterized by the triad of reticulated skin hyperpigmentation, nail dystrophy, and oral leukoplakia. Early mortality is often associated with bone marrow failure, infections, fatal pulmonary complications, or malignancy. Short-term treatment options for bone marrow failure in patients include anabolic steroids (e.g., oxymetholone), granulocyte macrophage colony-stimulating factor, granulocyte colony-stimulating factor, and erythropoietin. Other treatments include hematopoietic stem cell transplantation (SCT).

Idiopathic pulmonary fibrosis is a chronic and ultimately fatal disease characterized by a progressive decline in lung function. In some appropriate cases, the following agents are used to treat idiopathic pulmonary fibrosis: nintedanib, a tyrosine kinase inhibitor that targets multiple tyrosine kinases, including vascular endothelial growth factor, fibroblast growth factor, and PDGF receptors; and pirfenidone. Other treatments include lung transplantation. In some cases, lung transplantation for idiopathic pulmonary fibrosis (IPF) has been shown to confer a survival benefit over medical therapy.

The Telomerase RNA Component (TERC)

Telomerase has been a therapeutic target of great interest for over two decades, based on its activity in numerous cancers. Much of the focus has been on Telomerase reverse transcriptase (TERT), given its restricted expression in self-renewing cells, and its ability to confer immortality and transformation when introduced into non-self-renewing cells. TERC is expressed more broadly and has largely been overlooked as a potential target for manipulation.

The telomerase RNA component (TERC) serves two critical functions: it encodes the template sequence used by telomerase reverse transcriptase (TERT) for the addition of hexanucleotide repeats to telomeres, and it is the scaffold that nucleates multiple proteins that target telomerase to the Cajal body, where telomeres are extended.

In addition, TERC contains a box H/ACA domain at its 3' end, a motif that is functionally separable from the template domain and dispensable for telomerase activity in vitro. In vivo, the H/ACA motif is bound by a heterotrimer of dyskerin, NOP10, and NHP2 which stabilize TERC, and also by TCAB1, which is responsible for localizing the telomerase complex to Cajal bodies (Venteicher, A. S. et al. A human telomerase holoenzyme protein required for Cajal body localization and telomere synthesis. Science 323, 644-8 (2009)). Disruption of any of these interactions can also compromise telomere maintenance and cause telomere disease (Mitchell, J. R., Wood, E. & Collins, K A telomerase component is defective in the human disease dyskeratosis congenita. Nature 402, 551-5 (1999); Vulliamy, T. et al. Mutations in the telomerase component NHP2 cause the premature ageing syndrome dyskeratosis congenita. Proceedings of the National Academy of Sciences of the United States of America 105, 8073-8 (2008); Walne, A. J. et al. Genetic heterogeneity in autosomal recessive dyskeratosis congenita with one subtype due to mutations in the telomerase-associated protein NOP10. Human molecular genetics 16, 1619-29 (2007)). The H/ACA motif serve as guides for pseudouridylation of other RNAs by dyskerin (Kiss, T., Fayet-Lebaron, E. & Jady, B. E. Box H/ACA small ribonucleoproteins. Molecular cell 37, 597-606 (2010)). Interestingly, the 3' ends of snoRNAs and TERC terminate in a similar context—precisely 3 nt downstream of the ACA sequence. However, most snoRNAs are encoded in the introns of other genes, whereas TERC is an autonomous RNA pol II transcript, indicating major differences in the initial and possibly latter stages of biogenesis.

Increasing telomerase activity can be beneficial in several degenerative and age-related disorders. Conversely, inhibiting telomerase activity would be of significant utility for the treatment of cancer and disorders in which hyper-proliferative cells depend on telomerase for self-renewal.

The strategies to manipulate modulators of TERC levels can provide important advances in treatment strategies for a broad array of telomere diseases or disorders associated with telomerase dysfunction, e.g., dyskeratosis congenital, aplastic anemia, pulmonary fibrosis, idiopathic pulmonary fibrosis, hematological disorder, hepatic disease (e.g., chronic liver disease), and cancer, e.g., hematological cancer and hepatocarcinoma, etc.

Identification of agents that modulate TERC or telomerase in cell lines that recapitulate the human condition, such as iPS cells or tumor cells derived from cancer patients, can provide mechanisms to manipulate cellular function at a fundamental level.

Poly(A) Specific Ribonuclease (PARN)

PARN is known as a 3'-5' exoribonuclease responsible for degradation of the poly(A) tails of eukaryotic mRNAs, which is a rate-limiting step in mRNA turnover (Korner, C. G. & Wahle, E. Poly(A) tail shortening by a mammalian poly(A)-specific 3'-exoribonuclease. The Journal of biological chemistry 272, 10448-56 (1997)). PARN is stimulated by presence of a m7G-cap, and requires a minimal substrate of adenosine di- or tri-nucleotides—in other words, oligo(A) rather than strictly poly(A). PARN is a widely-expressed cap-dependent, poly(A) deadenylase with a canonical role in regulating global mRNA levels during development, and additional, more specialized functions including end-trimming of the Dicer-independent microRNA (miR)-451 and deadenylation of small nucleolar (sno)RNAs. PARN loss-of-function mutations are implicated in idiopathic pulmonary fibrosis and dyskeratosis congenita. The disclosure provides methods and agents that modulate the level or activity of human PARN. The nucleotide sequence of human PARN is NM_002582 (SEQ ID NO: 1) and the amino acid sequence of PARN is O95453 (SEQ ID NO: 96) (Table 9; FIG. 27 and FIG. 28).

Topoisomerase-Related Function Protein 4-2 (TRF4-2)

TRF4-2 (also known as PAP Associated Domain Containing 5 or PAPD5) is one of the seven members of the family of noncanonical poly(A) polymerases in human cells. TRF4-2 has been shown to act as a polyadenylase on abnormal pre-ribosomal RNAs in vivo in a manner analogous to degradation-mediating polyadenylation by the non canonical poly(A) polymerase Trf4p in yeast. PAPD5 is also involved in the uridylation-dependent degradation of histone mRNAs.

Figure 9:
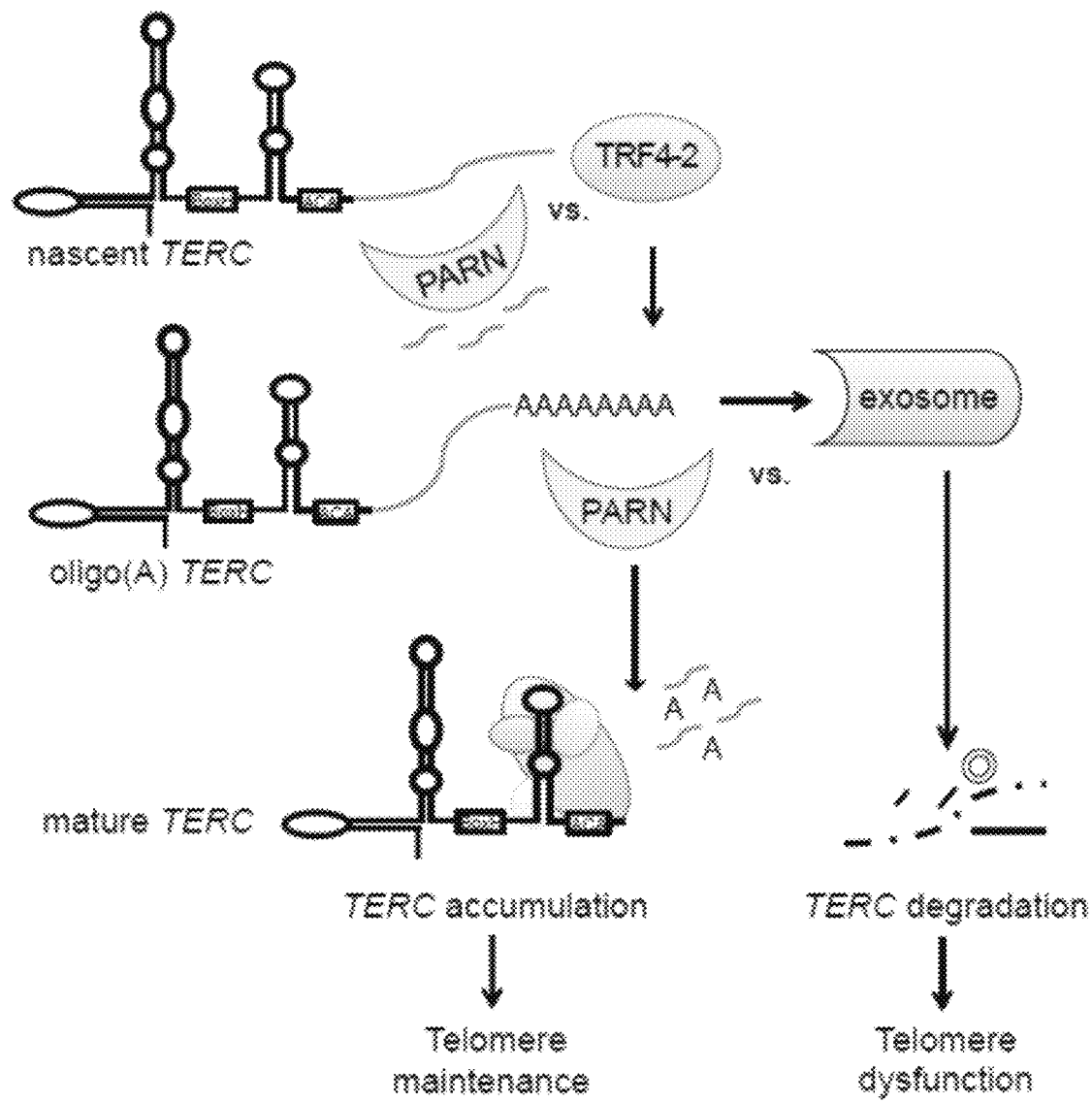
FIG. 9 is a diagram showing an exemplary model for TERC 3' end maturation by PARN.

Using somatic cells (fibroblasts) and induced pluripotent stem (iPS) cells from dyskeratosis congenita (DC) patients with genetic mutations, the present disclosure shows that PARN and TRF4-2 are involved in the 3'-end maturation of the telomerase RNA component (TERC). Patient cells, fibroblast cells as well as converted fibroblasts (iPS cells) in which PARN is disrupted show decreased levels of TERC which can be restored by decreasing levels of TRF4-2. Deep sequencing of TERC RNA 3' termini or ends, reveals that PARN and TRF4-2 are critically important for processing of post-transcriptionally acquired oligo(A) tails that target nuclear RNAs for degradation. Diminished TERC levels and the increased oligo(A) forms of TERC are normalized by restoring PARN or inhibiting TRF4-2. The disclosure describes reveals PARN and TRF4-2 as important players in the regulation and biogenesis of TERC (FIG. 9). FIG. 9 shows 3' ends of nascent TERC RNA are subject to TRF4-2-mediated oligo-adenylation, which targets transcripts for degradation by the exosome. PARN counteracts the degradation pathway by removing oligo(A) tails and/or trimming genomically-encoded bases (green) of nascent TERC to yield a mature 3' end. Mature TERC is protected from further oligo-adenylation and exonucleolytic processing, possibly by the dyskerin/NOP10/NHP2/GAR1 complex (colored ovals), and assembles into the telomerase holoenzyme to maintain telomeres. PARN deficiency tips the balance in favor of degradation, leading to reduced TERC levels and telomere dysfunction. Thus, the disclosure also provides methods and agents that modulate the level or activity of human TRF4-2. The nucleotide sequence of human TRF4-2 is NM_001040284 (SEQ ID NO: 2), and the amino acid sequence is Q8NDF8 (SEQ ID NO: 97) (Table 9; FIG. 29 and FIG. 30).

Modulating TERC Levels

Partly based on the role of PARN and TRF4-2 in the regulation and biogenesis of TERC, the disclosure provides methods to modulating TERC levels, e.g., by using agents that target TERC or agents that modulate the level or activity of TRF4-2 and/or PARN.

Figure 19:
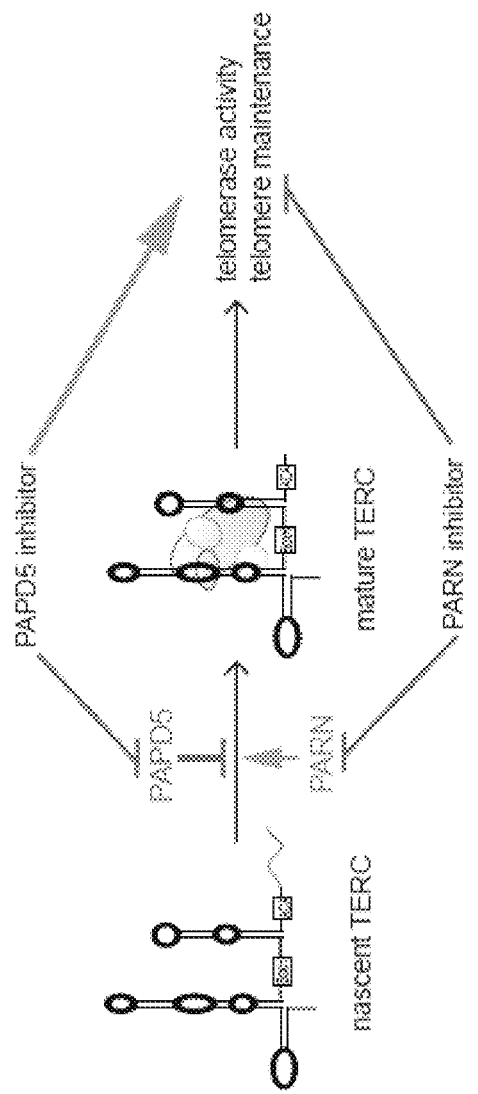
FIG. 19 is a schematic diagram showing an exemplary model of reciprocal regulation of TERC maturation by PARN and PAPD5.

FIG. 19 is a diagram demonstrating the reciprocal regulation of TERC levels by PAPD5 and PARN, and the potential for therapeutic manipulation of telomerase in degenerative or malignant disorders. As shown in FIG. 19, a PAPD5 inhibitor can inhibit PAPD5-mediated oligo-adenylation, which targets nascent TERC RNA for degradation by the exosome, thus increases the level or activity of TERC. In contrast, as PARN counteracts the degradation pathway by removing oligo(A) tails and/or trimming genomically-encoded bases of nascent TERC to yield a mature 3' end, PARN inhibitor will decrease the level or activity of TERC. In addition, increasing the level or activity of PARN can increase the level or activity of TERC, and increasing the level or activity of PAPD5 can decrease the level or activity of TERC.

In one aspect, the present disclosure provides methods of modulating TERC levels in cells. The cells can be, e.g., primary human cells, stem cells, induced pluripotent cells, fibroblasts, etc. The cells can be isolated from a sample obtained from the subject, e.g., the cells can be derived from any part of the body including, but not limited to, skin, blood, and bone marrow. The cells can also be cultured in vitro using routine methods with commercially available cell reagents (e.g., cell culture media). In some embodiments, the cells are obtained from a subject, having a telomere disease, being at risk of developing a telomere disease, or being suspected of having a telomere disease. In some embodiments, the subject has no overt symptoms.

The level or activity of TERC can be determined by various means, e.g., by determining the size of telomere in the cell, by determining the stability of TERC, by determining the amount of RNA, by measuring the activity of telomerase function, and/or by measuring oligo-adenylated (oligo(A)) forms of TERC. TERC stability can be assessed, e.g., by measuring the TERC decay rates. Oligo-adenylated (oligo(A)) forms of TERC can be measured, e.g., using rapid amplification of cDNA ends (RACE) coupled with targeted deep sequencing (e.g., at the TERC 3' end) to detect oligo-adenylated (oligo(A)) forms of TERC. The size of a telomere can be measured, e.g., using Flow-fluorescent in-situ hybridization (Flow-FISH) technique.

In some methods, the modulation of endogenous TERC is performed. Such methods can include, e.g., altering telomerase activity, e.g., increasing or decreasing telomerase activity. The methods can involve reducing RNA expression in cells, e.g., non-coding RNA in TERC. Telomerase activity can be, e.g., regulated by modulating TERC levels by contacting cells with test compounds known to modulate protein synthesis. The methods may involve targeting post-processing activity of the endogenous TERC locus. These methods involve manipulating TERC including identifying subjects with genetic mutation (e.g., mutation in PARN), isolating cells (e.g., fibroblast), and treating cells with agents that modulate TERC levels.

The present disclosure shows that TERC levels are modulated at the post-transcriptional level. Thus, in one aspect, methods of modulating the level or activity of TERC involve modulating the level or activity of PARN and TRF4-2.

In some embodiments, the methods involve an agent that modulates the level or activity of PARN, thereby altering the level or activity of TERC. In some cases, the agent increases the level or activity of PARN. Alternatively, the agent decreases the level or activity of PARN. In some embodiments, the agent is a nucleic acid comprising a nucleotide sequence that encodes PARN. The agent can also be an anti-PARN antibody or anti-PARN antibody fragment. In some embodiments, the agent is an antisense molecule or a small interfering nucleic acid which is specific for a nucleic acid encoding PARN. The antisense molecule can be an oligonucleotide. In some cases, the agent binds to PARN. In some embodiments, the method involves genome editing technology that target PARN.

In some embodiments, the methods involve an agent that modulates the level or activity of TRF4-2, thereby altering the level or activity of TERC. In some embodiments, the agent increases the level or activity of TRF4-2. Alternatively, the agent decreases the level or activity of TRF4-2. In some embodiments, the agent is a nucleic acid comprising a nucleotide sequence that encodes TRF4-2. The agent can also be an anti-TRF4-2 antibody or anti-TRF4-2 antibody fragment. In some embodiments, the agent is an antisense molecule or a small interfering nucleic acid which is specific for a nucleic acid encoding TRF4-2. The antisense molecule can be an oligonucleotide. In some cases, the agent binds to TRF4-2. In some embodiments, the method involves genome editing technology that target TRF4-2.

In some embodiments, the agents that decrease the level of PARN are shRNA that target PARN, e.g., SEQ ID NO: 74 and SEQ ID NO: 75.

In some embodiments, the agents that decrease the level of PAPD5 are shRNA that target PAPD5, e.g., SEQ ID NOs: 79-83. In some embodiments, the agent is SEQ ID NO: 79 or SEQ ID NO: 83.

In some embodiments, the agent that increase the level of PARN is a vector that includes a nucleic acid sequence that encodes PARN (SEQ ID NO: 96), e.g., a lentiviral vector that encodes PARN.

In some embodiments, the agent that increase the level of TRF4-2 is a vector that includes a nucleic acid sequence that encodes TRF4-2 (SEQ ID NO: 97), e.g., a lentiviral vector that encodes TRF4-2.

In some embodiments, CRISPR/Cas9 genome targeting can be performed to create biallelic null mutations. These mutations can decrease the level of PARN or TRF4-2. In some embodiments, lentiviral vectors containing guide RNAs (gRNAs) to PARN (e.g., SEQ ID NO: 90, 92, 94) are designed and used to transduce cells in order decrease the level of PARN. In some embodiments, lentiviral vectors containing guide RNAs (gRNAs) to TRF4-2 (e.g., SEQ ID NO: 84, 86, 88) are designed and used to transduce cells in order decrease the level of TRF4-2.

In some embodiments, a PAPD5 inhibitor and/or a PARN inhibitor can be used to modulate the level or activity of TERC. These agents include, but are not limited to, adenosine analogues, aminoglycosides, and purine nucleotides, etc.

In some cases, the aminoglycoside can be a member of the neomycin and kanamycin families. The aminoglycoside can be, for example, kanamycin B sulfate, pramycin sulfate, spectinomycin dihydrochloride pentahydrate, ribostamycin sulfate, sisomicin sulfate, amikacin disulfide, dihydrostreptomycin sesquisulfate, hygromycin B, netilmicin sulfate, paromomycin sulfate, kasugamycin, neomycin, gentamicin, tobramycin sulfate, streptomycin sulfate, or neomycin B, or derivatives thereof.

In some embodiments, the agent is a nucleoside analogue, e.g., a adenosine analogue, 8-chloroadenosine (8-Cl-Ado) and 8-aminoadenosine (8-amino-Ado), or the triphosphate derivative thereof, synthetic nucleoside analogues bearing a fluoroglucopyranosyl sugar moiety, benzoyl-modified cytosine or adenine, adenosine- and cytosine-based glucopyranosyl nucleoside analogues, or glucopyranosyl analogues bearing uracil, 5-fluorouracil or thymine, etc.

Adenosine analogues, aminoglycosides, and purine nucleotides are known in the art, and they are described, e.g., in Kim, Kyumin, et al. "Exosome Cofactors Connect Transcription Termination to RNA Processing by Guiding Terminated Transcripts to the Appropriate Exonuclease within the Nuclear Exosome." Journal of Biological Chemistry (2016): jbc-M116; Chen, Lisa S., et al. "Chain termination and inhibition of mammalian poly (A) polymerase by modified ATP analogues." Biochemical pharmacology 79.5 (2010): 669-677; Ren, Yan-Guo, et al. "Inhibition of Klenow DNA polymerase and poly (A)-specific ribonuclease by aminoglycosides." Rna 8.11(2002): 1393-1400; Thuresson, Ann-Charlotte, Leif A. Kirsebom, and Anders Virtanen. "Inhibition of poly (A) polymerase by aminoglycosides." Biochimie 89.10 (2007): 1221-1227; AA Balatsos, N., et al. "Modulation of poly (A)-specific ribonuclease (PARN): current knowledge and perspectives." Current medicinal chemistry 19.28 (2012): 4838-4849; Balatsos, Nikolaos A A, Dimitrios Anastasakis, and Constantinos Stathopoulos. "Inhibition of human poly (A)-specific ribonuclease (PARN) by purine nucleotides: kinetic analysis." Journal of enzyme inhibition and medicinal chemistry 24.2 (2009): 516-523; Balatsos, Nikolaos A A, et al. "Competitive inhibition of human poly (A)-specific ribonuclease (PARN) by synthetic fluoro-pyranosyl nucleosides." Biochemistry 48.26 (2009): 6044-6051; and Balatsos, Nikolaos, et al. "Kinetic and in silico analysis of the slow-binding inhibition of human poly (A)-specific ribonuclease (PARN) by novel nucleoside analogues." Biochimie 94.1 (2012): 214-221; each of which is incorporate by reference in its entirety.

Subjects

The terms "subject" and "patient" are used interchangeably throughout the specification and describe an animal, human or non-human. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

In some embodiments, the methods described in this disclosure involves identifying a subject as having, being at risk of developing, or suspected of having a disorder associated with telomerase dysfunction. The methods include determining the level or activity of TERC, PARN, or TRF4-2 in a cell from the subject; comparing the level or activity of TERC, PARN, or TRF4-2 to the reference level or reference activity of TERC, PARN, or TRF4-2; and identifying the subject as having, being at risk of developing, or suspected of having a disorder associated with telomerase dysfunction if the level or activity of TERC, PARN, or TRF4-2 is significantly different from the reference level or activity of TERC, PARN, or TRF4-2. In some embodiments, there reference level or activity of TERC, PARN, or TRF4-2 are determined by cells obtained from subjects without disorders associated with telomerase dysfunction.

The level or activity of TERC, PARN, or TRF4-2 can be determined in various types of cells from a subject. The methods can include obtaining cells from a subject, and transforming these cells to iPS cells, and these iPS cells can be used to determine the level or activity of TERC, PARN, or TRF4-2. These cells can be, e.g., primary human cells or tumor cells The subject may be one having a mutation at PARN, e.g., a deletion containing part of PARN gene or the entire PARN gene. For example, the mutation may be one wherein the amino acid residue at position 7 of PARN is not asparagine or serine. For example, the subject can have a missense variant c.19A>C, resulting in a substitution of a highly conserved amino acid p.Asn7His. The subject can have a missense mutation c.260C>T, encoding the substitution of a highly conserved amino acid, p.Ser87Leu.

Methods of Treatment

The methods described herein include methods for the treatment of disorders associated with telomerase dysfunction or at least one symptom associated with such disorders. The disorder can be, e.g., dyskeratosis congenital, aplastic anemia, pulmonary fibrosis, idiopathic pulmonary fibrosis, hematological disorder, hepatic disease (e.g., chronic liver disease), or cancer, e.g., hematological cancer or hepatocarcinoma.

Generally, the methods include administering a therapeutically effective amount of agents that modulate the level or activity of TERC as described herein, to a subject who is in need of, or who has been determined to be in need of, such treatment.

As used in this context, to "treat" means to ameliorate at least one symptom of the disorder associated with telomerase dysfunction. In some embodiments, the treatment results in an increase the telomerase level or activity; thus, a treatment can ameliorate symptoms that are associated with abnormal telomerase function or telomerase deficiency.

A subject can be administered at least one (e.g., at least 2, 3, 4, or 5) dose of the agent. The agent can be administered to the subject at least once a day (e.g., twice a day, three times a day, and four times a day), at least once a week (e.g., twice a week, three times a week, four times a week), and/or at least once a month. A subject can be treated (e.g., periodically administered the agent) for a prolonged period of time (e.g., at least one month, two months, six months, one year, two years, three years, four years, or five years). As described in detail herein, the dosage of the agent to be administered to the subject can be determined by a physician by consideration of a number of physiological factors including, but not limited to, the sex of the subject, the weight of the subject, the age of the subject, and the presence of other medical conditions. The agent can be administered to the subject orally, intravenously, intraarterially, subcutaneously, intramuscularly, intracranially, or via injection into the cerebrospinal fluid. Likewise, the agent may be formulated as a solid (e.g., for oral administration) or a physiologically acceptable liquid carrier (e.g., saline) (e.g., for intravenous, intraarterial, subcutaneous, intramuscular, or cerebrospinal administration).

In some embodiments, methods of treatment can include administering to a subject at least one (e.g., at least two, three, four, five, or six) agents (e.g., a nucleic acid) that increases the expression level or activity of one or more nucleic acids, e.g., PARN. Such methods of treatment can also include administering an agent to a subject (e.g., a small molecule) that can inhibit the expression or activity of one of more nucleic acids, e.g., TRF4-2.

In some embodiments, the agents are administered to a subject in any combination with treatments for telomere diseases that are known in the art.

Also provided are methods of treating a telomere, which includes administering to a subject at least one (e.g., at least two, three, four, five, or six) agent (e.g., a nucleic acid) that alters (e.g., decreases or increases) the expression (e.g., protein) or activity of one or more (e.g., at least two, three, four, five, or six) of the genes listed in Tables 3-7 (e.g., an inhibitory nucleic acid or antibody).

Induced Pluripotent Stem Cells

Induced pluripotent stem cells (iPSC or iPS), are somatic cells (e.g., derived from patient skin or other cell) that have been genetically reprogrammed to an embryonic stem cell-like state by being forced to express genes and factors important for maintaining the defining properties of embryonic stem cells. These cells are generated by methods known in the art.

It is known that mouse iPSCs demonstrate important characteristics of pluripotent stem cells, including expressing stem cell markers, forming tumors containing cells from all three germ layers, and being able to contribute to many different tissues, when injected into mouse embryos at a very early stage in development.

Human iPSCs also express stem cell markers and are capable of generating cells characteristic of all three germ layers. iPSCs can be generated from human fibroblasts and are already useful tools for drug development and modeling of diseases. Viruses are currently used to introduce the reprogramming factors into adult cells (e.g., lentiviral vectors disclosed herein), and this process can be carefully controlled and tested in cultured, isolated cells first to then treat cells (e.g., by contacting with a test compound) to express altered markers, e.g., iPSCs from tumor cells can be manipulated to differentiate or iPSCs from cardiomyocytes can be manipulated to de-differentiate.

The iPSC manipulation strategy can be applied to any cells obtained from a subject to test whether the compound can alter the level or activity of TERC, PARN, or TRF4-2. The cells are contacted with test compounds (e.g., small molecules). In some embodiments, these iPSC cells can be used for screening compounds that modulate TERC. In some embodiments, the iPSC cells are converted from patient skin fibroblasts.

Cancer

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells.

Many cancer cells have abnormal telomeres. Thus, treatments described herein can also be used to treat cancers. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. Cancers treatable using the methods described herein are cancers that have increased levels of TERC, an increased expression of genes such as TERC and/or TERT, or increased activity of a telomerase relative to normal tissues or to other cancers of the same tissues.

In some embodiments, the tumor cells isolated from subjects diagnosed with cancer can be used to screen test for compounds that alter TERC levels. In some embodiments, the tumor cells can be used to screen test compounds that alter the expressive or activity of PARN or TRF4-2. The cancer cells used in the methods can be, e.g., cancer stem cells. Such methods can be used to screen a library of test compounds, e.g., compounds that alter or change expression of protein or RNA of telomere-associated genes (e.g., TERC, PARN, TRF4-2/PAPD5).

In some embodiments, agents that decrease the level or activity of TERC (e.g., PANR inhibitors) are used to treat cancer. In some embodiments, these agents are used in combination with other cancer treatments, e.g., chemotherapies, surgery, or radiotherapy.

Aging

Telomeres shorten over the human life span. In large population based studies, short or shortening telomeres are associated with numerous diseases. Thus, telomeres have an important role in the aging process, and can contribute to various diseases. The role of telomeres as a contributory and interactive factor in aging, disease risks, and protection is described, e.g., in Blackburn, Elizabeth H., Elissa S. Epel, and Jue Lin. "Human telomere biology: A contributory and interactive factor in aging, disease risks, and protection," Science 350.6265 (2015): 1193-1198, which is incorporated by reference in its entirety.

As used herein, the term "aging" refers to degeneration of organs and tissues over time, in part due to inadequate replicative capacity in stem cells that regenerate tissues over time. Aging may be due to natural disease processes that occur over time, or those that are driven by cell intrinsic or extrinsic pressures that accelerate cellular replication and repair. Such pressures include natural chemical, mechanical, and radiation exposure; biological agents such as bacteria, viruses, fungus, and toxins; autoimmunity, medications, chemotherapy, therapeutic radiation, cellular therapy. As the telomere is an important factor in aging and disease development, the methods described herein can be used for treating, mitigating, or minimizing the risk of, a disorder associated with aging (and/or one or more symptoms of a disorder associated with aging) in a subject. The methods include the step of identifying a subject as having, or being at risk of a disorder associated with aging; and administering a pharmaceutical composition to the subject. In some embodiments, the pharmaceutical composition includes an agent that alters the level or activity of TERC, e.g., increase the level or activity of TERC.

As used herein, the term "disorders associated with aging" refers to disorders that are associated with the ageing process. Exemplary disorders include, e.g., macular degeneration, diabetes mellitus (e.g., type 2 diabetes), osteoarthritis, rheumatoid arthritis, sarcopenia, cardiovascular diseases such as hypertension, atherosclerosis, coronary artery disease, ischemia/reperfusion injury, cancer, premature death, as well as age-related decline in cognitive function, cardiopulmonary function, muscle strength, vision, and hearing.

The disorder associated with aging can be a degenerative disorder, e.g., a neurodegenerative disorder. Exemplary neurodegenerative disorders include Motor Neuron Disease, Creutzfeldt-Jakob disease, Machado-Joseph disease, Spinocerebellar ataxia, Multiple sclerosis (MS), Parkinson's disease, Alzheimer's disease, Huntington's disease, hearing and balance impairments, ataxias, epilepsy, mood disorders such as schizophrenia, bipolar disorder, and depression, dementia, Pick's Disease, stroke, CNS hypoxia, cerebral senility, and neural injury such as head trauma. Recent studies have shown the association between shorter telomeres and Alzheimer's disease. The relationship between telomere length shortening and Alzheimer's disease is described, e.g., in Zhan, Yiqiang, et al. "Telomere length shortening and Alzheimer disease—a Mendelian Randomization Study," JAMA neurology 72.10 (2015): 1202-1203, which is incorporated by reference in its entirety. In some embodiments, the neurodegenerative disorder is dementia, e.g., Alzheimer's disease.

It has also been determined that there an inverse association between leucocyte telomere length and risk of coronary heart disease. This relationship is described, e.g., in Haycock, Philip C., et al. "Leucocyte telomere length and risk of cardiovascular disease: systematic review and meta-analysis." (2014): g4227; and Codd, Veryan, et al. "Identification of seven loci affecting mean telomere length and their association with disease." Nature genetics 45.4 (2013): 422-427; each of which is incorporated by reference in its entirety. Thus, there is strong evidence for a causal role of telomere-length variation in cardiovascular disease (CVD), or coronary artery disease (CAD), In some embodiments, the disorder is a cardiovascular disease (CVD), and/or coronary artery disease (CAD), and the present disclosure provides methods of treating, mitigating, or minimizing the risk of, these disorders. In some cases, the disorder is an atherosclerotic cardiovascular disease.

Furthermore, a meta-analysis of 5759 cases and 6518 controls indicated that shortened telomere length was significantly associated with type 2 diabetes mellitus risk. The relationship between telomere length and type 2 diabetes mellitus is described, e.g., in Zhao, Jinzhao, et al. "Association between telomere length and type 2 diabetes mellitus: a meta-analysis." PLoS One 8.11 (2013): e79993, which is incorporated by reference in its entirety. In some embodiments, the disorder is a metabolic disorder, e.g., type 2 diabetes mellitus.

The methods described herein can be used for treating or diagnosing degenerative disorders in a subject. Degenerative disorders that can be treated or diagnosed using the methods described herein include those of various organ systems, such as affecting brain, heart, lung, liver, muscles, bones, blood, gastrointestinal and genito-urinary tracts. In some cases, degenerative disorders are those that have shortened telomeres, decreased levels of TERC, and/or decreased levels of telomerase relative to normal tissues.

In some embodiments, aged cells can be used to screen test compounds that alter the expressive or activity of PARN or TRF4-2. The aged cells used in the methods can be, e.g., those with genetic lesions in telomere biology genes, those isolated from elderly subjects, or those that undergo numerous rounds of replication in the lab. Such methods can be used to screen a library of test compounds, e.g., compounds that alter or change expression of protein or RNA of telomere-associated genes (e.g., TERC, PARN, TRF4-2/PAPD5). Exemplary methods of screening and screening techniques are described herein.

In some embodiments, agents that increase the level or activity of TERC (e.g., TRF4-2/PAPD5 inhibitors) are used to treat age-related degenerative disorders due to natural causes or environmental causes. In some embodiments, these agents are used in combination with other treatments.

Methods of Screening

Included herein are methods for screening test compounds, e.g., polypeptides, nucleic acids, fusion proteins, polynucleotides, inorganic or organic large or small molecule test compounds, to identify agents useful in the treatment of telomere diseases e.g., diseases associated with altered levels of TERC, activity and/or telomerase function. Also included are methods for screening test compounds, e.g., polypeptides, nucleic acids, fusion proteins, polynucleotides, inorganic or organic large or small molecule test compounds, to identify agents that modulate the level or activity of TERC, PARN, and/or TRF4-2.

The small molecules can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czamik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are nucleic acids (e.g., shRNA). In some embodiments, the test compounds are nucleic acids (e.g., isolated cDNA). In some embodiments, the test compounds are small molecules. In some embodiments, the test compounds are vectors comprising nucleic acids that can encode fusion proteins (e.g., CRSPR-based fusion proteins). In some embodiments, the fusion proteins can encode modified TRF4-2. In some embodiments, the fusion proteins can encode an active domain of PARN protein. In some embodiments, the test compounds can be peptides or peptidomimetic molecules e.g., molecules that bind TRF4-2. In some embodiments, the test compounds are viral encoded nucleic acids e.g., PARN cDNA.

As used herein, "nucleic acids" refers to isolated DNA fragments (e.g., cDNA), RNA (e.g., coding and non-coding RNA), nucleic acids or fragments thereof, vectors comprising nucleic acids (e.g., viral and plasmid vectors). The nucleic acids can be short or long comprising at least 10 to 100 nucleotides. The nucleic acids can be labelled at either ends (5'-tag or 3' tag). The nucleic acids can encode nuclear localization signal at their 3' and 5' ends.

Generally, the methods of screening involve isolating a cell, e.g., human or an animal cell, contacting the cell with a test compound, e.g., small molecules and/or nucleic acids, comparing levels or activity of TERC, PARN, and/or TRF4-2 to a reference level.

The term "reference" level is an art-known term and typically refers to a baseline value. Skilled practitioners will appreciate that baseline values can be established by standard methods and generally are determined in the absence of a test compound, treatment step, or disease. Often the reference level from a patient derived cell is compared to a reference level from a human or other eukaryotic cell that is recognized by a skilled artisan as a control level or a baseline level for the cell. For example, it is art recognized that normal cultured fibroblast cell with known characteristic levels of housekeeping genes, e.g., beta actin. All such levels are generally detectable, but can also be low or undetectable.

In the presently described methods, reference levels can include baseline RNA or protein levels that generally known to occur in a cell, in a "naïve" state, e.g., in absence of an administrative or a treatment step or disease. In some embodiments, a reference level is determined at baseline in a patient who is identified with a telomere disease. In some embodiments, the reference level is determined by way of determining amount of mature TERC species, before a compound is administered into a cell, e.g., a patient-derived iPS cell. In some embodiments, the reference level is the baseline RNA or protein level in a cell derived from a subject without telomere diseases.

The cells can be treated with commercially available reagents by standard methods, wherein the cells will be further manipulated with test compounds that modulate TERC in the cells. The desired effect is not limiting to any condition but in some embodiments can be to alter TERC levels. In some embodiment the desired effect can be to alter telomere size in the cell. In some embodiment the desired effect can restore or alter telomerase activity in the cell. In some embodiments, the desired effect can include alteration (increase or decrease) TERC species but not all RNA species in a cell.

In some embodiments, a test compound is applied to a cell, e.g., an isolated fibroblast cell, e.g., a normal fibroblast cell or a diseased fibroblast cell, and one or more effects of the test compound is evaluated, e.g., using a quantitative RT-PCR assay or, a polyacrylamide gel based telomerase activity assay (TRAP) in the presence of reducing agents including dithiothreitol (DTT) or mercaptoethanol, which detects change or modulation of telomerase activity by rendering fragments of telomeres that can be separated on a polyacrylamide gel.

A candidate compound that has been selected from the screening methods can be further validated and purified to test in animal models by further screening (in vivo screening methods).

A test compound can also be used to screen a library to develop a "probe" compound that may be further used in a counter-screen, e.g., sequencing probes. Such test compounds are not necessarily structurally or functionally similar but when contacted with a cell have an effect that is rendered in a robust manner, e.g., TERC levels are altered at desirable levels at any treatment time-point or upon repetition. By using a first screen and a counter-screen, the method disclosed will select a therapeutic compound that can be administered to treat one or more cellular defect of a said disorder (e.g., telomere size, TERC decay rate, TERC expression or telomerase maturation in the aspect of telomere disease), and can be considered a candidate therapeutic agent. Candidate therapeutic agents, once screened in an animal model and clinical setting, are therapeutic agents. Candidate compounds, candidate therapeutic agents, and therapeutic agents can be optionally optimized and/or derivatized, and formulated with physiologically acceptable excipients to form pharmaceutical compositions.

The candidate compound (e.g., test compounds that decrease TRF4-2 and restore steady-state levels of TERC and optionally, that also do not reduce cell proliferation or viability, and so not affect non-specific targets, and optionally that also have activity in an in vivo model) can be selected and systematically altered, e.g., using rational design, to optimize binding affinity, avidity, specificity, or other parameter for use in therapy. A variety of techniques useful for determining the structures of candidate compounds can be used, e.g., NMR, mass spectrometry, gas chromatography equipped with electron capture detectors, fluorescence and absorption spectroscopy.

The disclosure also provides methods for screening modulators of TERC, PARN and/or TRF4-2. In some embodiments, methods of screening include contacting a cell with a test compound, e.g., a nucleic acid or a small molecule; determining the level or activity of TERC, PARN or TRF4-2 in the cell; comparing the level or activity of TERC, PARN or TRF4-2 in the cells to a reference level. If the level or activity of TERC, PARN or TRF4-2 in the cells is significantly different from the reference level, the test compound will be selected as a candidate compound.

As used herein, the term "significant" or "significantly" refers to statistical significance (or a statistically significant result) is attained when a p-value is less than the significance level (denoted a, alpha). The p-value is the probability of obtaining at least as extreme results given that the null hypothesis is true whereas the significance level a is the probability of rejecting the null hypothesis given that it is true. In some embodiments, the significance level is 0.05, 0.01, 0.005, 0.001, 0.0001, or 0.00001, etc. In some embodiments, "significantly altered" or "significantly different" refers to the difference between the two groups have attained the statistical significance.

In some embodiments, the methods of screening involve determining whether the test compound can achieve a desired effect. In some embodiments, the "desired effect" is determined by the quality, density or source of cells (e.g., human or animal), and herein are provided in the various examples of cells that are contacted with a test compound, to elicit a desired effect.

These cells can be obtained from various sources, e.g., from a patient diagnosed with cancer, from a control subject, or from a cell line. In some embodiments, the cells are iPSC cells. In some embodiments, the iPSC cells are obtained from a subject who has telomere disease. In some embodiments, the cells are PARN deficient cells. The test compounds will be selected as a candidate compound if the test compound restores the level or activity of PARN to a normal level (the level or activity of PARN in a cell without PAN deficiency). In some embodiments, the test compound restores the level or activity or TERC to a normal level (the level or activity of PARN in a cell without PAN deficiency). In some embodiments, these cells are tumor cells or cancer cells.

The presence and/or level of a nucleic acid can be evaluated using methods known in the art, e.g., using polymerase chain reaction (PCR), reverse transcriptase polymerase chain reaction (RT-PCR), quantitative or semi-quantitative real-time RT-PCR, digital PCR i.e. BEAMing ((Beads, Emulsion, Amplification, Magnetics) Diehl (2006) Nat Methods 3:551-559); RNAse protection assay; Northern blot; various types of nucleic acid sequencing (Sanger, pyrosequencing, NextGeneration Sequencing); fluorescent in-situ hybridization (FISH); or gene array/chips) (Lehninger Biochemistry (Worth Publishers, Inc., current addition; Sambrook, et al, Molecular Cloning: A Laboratory Manual (3. Sup.rd Edition, 2001); Bernard (2002) Clin Chem 48(8): 1178-1185; Miranda (2010) Kidney International 78:191-199; Bianchi (2011) EMBO Mol Med 3:495-503; Taylor (2013) Front. Genet. 4:142; Yang (2014) PLOS One 9(11):e110641); Nordstrom (2000) Biotechnol. Appl. Biochem. 31(2):107-112; Ahmadian (2000) Anal Biochem 280:103-110. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, Proteins and Proteomics: A Laboratory Manual, Cold Spring Harbor Laboratory Press; 2002; Hardiman, Microarrays Methods and Applications: Nuts & Bolts, DNA Press, 2003), can be used to detect the presence and/or level of PARN, TERC or TRF4-2 Measurement of the level of a biomarker can be direct or indirect. For example, the abundance levels of TERC can be directly quantitated. For example, the RNA levels of PSRN or TRF4-2 can be directly quantitated using quantitative PCR. Alternatively, the amount of a protein or RNA can be determined indirectly by measuring abundance levels of cDNA, amplified RNAs or DNAs, or by measuring quantities or activities of other RNAs associated with the protein or protein-associated molecules (e.g., sno RNAs that interact with TERC RNA) that are indicative of the expression level of the protein or RNA. In some embodiments, a technique suitable for the detection of alterations in the structure or sequence of nucleic acids, such as the presence of deletions, amplifications, or substitutions, can be used for the detection of biomarkers of this invention.

Methods of Diagnosing

The present specification provides methods of diagnosing a subject as having telomere disease. As an example, if the level or activity of TERC, PARN, and/or TRF4-2 in a subject is comparable to the level or activity of TERC, PARN, and/or TRF4-2 in a subject having the telomere disease and, optionally, the subject has one or more symptoms associated with telomere disease (e.g., aplastic anemia, pulmonary fibrosis, hepatic cirrhosis), then the subject can be diagnosed as having or being at risk of developing a telomere disease.

In some embodiments, if the level or activity of TERC, PARN, and/or TRF4-2 in a subject is comparable to the level or activity of TERC, PARN, and/or TRF4-2 in a control subject who does not have a telomere disease, then the subject can be diagnosed as not having telomere disease or not being at risk of developing a telomere disease.

In some embodiments, the subject is determined to have or being at risk of developing a telomere disease if there is a mutation at PARN. The mutation can be a deletion containing part of PARN gene or the entire PARN gene. The mutation can also be a mutation at position 7 and/or 87 of PARN, e.g., the amino acid residue at position 7 is not asparagine, and/or the amino acid residue at position 87 of PARN is not serine. For example, the mutation can be a missense variant c.19A>C, resulting in a substitution of a highly conserved amino acid p.Asn7His. In some cases, the mutation is a missense mutation c.260C>T, encoding the substitution of a highly conserved amino acid, p.Ser87Leu.

In some embodiments, a subject has no overt signs or symptoms of a telomere disease, but the level or activity of TERC, PARN or TRF4-2 may be associated with the presence of a telomeres disease, then the subject has an increased risk of developing telomere disease. In some embodiments, once it has been determined that a person has telomere disease, or has an increased risk of developing telomere disease, then a treatment, e.g., with a small molecule or a nucleic acid encoded by a construct, as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of TRF4-2 protein, e.g., a control reference level that represents a normal level of TRF4-2 protein, e.g., a level in an unaffected subject or a subject who is not at risk of developing a disease described herein, and/or a disease reference that represents a level of the proteins associated with conditions associated with telomere disease, e.g., a level in a subject having telomere disease (e.g., pulmonary fibrosis, hepatic cirrhosis or aplastic anemia). In another embodiment, the reference comprises a predetermined value for a meaningful level of PARN protein, e.g., a control reference level that represents a normal level of PARN protein, e.g., a level in an unaffected subject or a subject who is not at risk of developing a disease described herein, and/or a disease reference that represents a level of the proteins associated with conditions associated with telomere disease, e.g., a level in a subject having telomere disease (e.g., pulmonary fibrosis, hepatic cirrhosis or aplastic anemia).

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein. In some embodiments, it may be desirable that the control subject is deficient in PARN gene (e.g., Dyskeratosis Congenita), and in other embodiments, it may be desirable that a control subject has cancer. In some cases, it may be desirable that the control subject has high telomerase activity, and in other cases it may be desirable that a control subject does not have substantial telomerase activity.

In some embodiments, the level of TERC or PARN in a subject being less than or equal to a reference level of TERC or PARN is indicative of a clinical status (e.g., indicative of a disorder as described herein, e.g., telomere disease). In some embodiments, the activity of TERC or PARN in a subject being greater than or equal to the reference activity level of TERC or PARN is indicative of the absence of disease.

The predetermined value can depend upon the particular population of subjects (e.g., human subjects or animal models) selected. For example, an apparently healthy population will have a different 'normal' range of levels of TERC than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art. In characterizing likelihood, or risk, numerous predetermined values can be established.

Nucleic Acid Composition

Agents useful in the methods of treatment or screening described herein include nucleic acid molecules that increase or decrease the level of TERC, or the expression or activity of any of the proteins (e.g., TRF4-2 and PARN) listed in Examples and Tables 3-8, or increase or decrease the expression or activity of any of the mRNAs encoding another marker listed in Table 3, 5 or 6. A sense nucleic acid can contain a sequence that is at least 80% (e.g., at least 90%, 95%, 96%, 97%, 98%, 99%, or 100%) identical to the sequence of any one of the genes (e.g., mature TERC, TRF4-2 and PARN) listed in Tables 3-8, or the sequence of any one of the mRNAs listed in Tables 6-8. Sense nucleic acids can contain one or more of any of the modifications (e.g., backbone modifications, nucleobase modifications, sugar modifications, or one or more conjugated molecules) described herein without limitation. Methods of making and administering sense nucleic acids are known in the art. Additional methods of making and using sense nucleic acids are described herein.

The methods of treatment include administration of composition comprising inhibitory nucleic acid molecules that are designed to inhibit a target RNA, e.g., antisense, shRNA, siRNA. The methods of screening include use of test compounds comprising various compositions, also comprising inhibitory nucleic acid molecules that are designed to inhibit a specific target RNA, e.g., antisense, shRNA, siRNA. RNA interference methods comprise modulating levels by inhibiting any one or more of TERC, PARN, or TRF4-2 or interacting protein, in a specific disease context but not global stead state levels of all RNA species. In some embodiments, the inhibitory nucleic acids inhibit TRF4-2 to treat symptoms of telomere disease or deficiency; in some embodiments, inhibitory nucleic acids inhibit binding of an interaction partner of TRF4-2, or TERC, e.g., a RNA species, by blocking its functional domain.

The inhibitory nucleic acids useful in the present methods are sufficiently complementary to the target genes, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of an RNA, then the bases are considered to be complementary to each other at that position. In some embodiments, 100% complementarity is not required. In some embodiments, 100% complementarity is required. Routine methods can be used to design an inhibitory nucleic acid that binds to the target sequence with sufficient specificity.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments of 5, 6, 7, 8, 9, 10 or more nucleotides in length comprising a stretch of at least five consecutive nucleotides within the seed sequence, or immediately adjacent thereto, are considered to be suitable for targeting as well. In some embodiments, target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the inhibitory nucleic acid contains about 5 to about 30 nucleotides). In some embodiments, target segments are represented by RNA sequences that comprise at least the 5 consecutive nucleotides from the 3'-terminus of one of the seed sequence (the remaining nucleotides being a consecutive stretch of the same miRNA beginning immediately downstream of the 3'-terminus of the target segment and continuing until the inhibitory nucleic acid contains about 5 to about 30 nucleotides). One having skill in the art armed with the sequences provided herein will be able, without undue experimentation, to identify further preferred regions to target.

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the disclosure, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a miRNA molecule or an mRNA molecule, then the inhibitory nucleic acid and the miRNA or mRNA are considered to be complementary to each other at that position. The inhibitory nucleic acids and the miRNA or mRNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the inhibitory nucleic acid and the miRNA target. For example, if a base at one position of an inhibitory nucleic acid is capable of hydrogen bonding with a base at the corresponding position of a miRNA or a mRNA, then the bases are considered to be complementary to each other at that position. 100% complementarity is not required.

In general, the inhibitory nucleic acids useful in the methods described herein have at least 80% sequence complementarity to a target region within the target nucleic acid, e.g., 90%, 95%, or 100% sequence complementarity to the target region within an miRNA. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol. 215:403-410, 1990; Zhang and Madden, Genome Res. 7:649-656, 1997).

In some embodiments, the inhibitory nucleic acid is a shRNA. shRNA mediated RNA interference is a process whereby double-stranded RNA (dsRNA) induces the sequence-specific degradation of homologous mRNA in mammalian cells. These nucleic acid molecules or constructs can include dsRNA molecules comprising 10-60, e.g., 10, 11-15, 16-18, 19, 20, 21, 22, 23, 24, 25, 26, 27, 28, 29, or 30 or 45 or 60 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, or can be transcribed in vitro from a DNA template, or in vivo from, e.g., small hairpin RNAs (shRNAs). The dsRNA molecules can be designed using any method known in the art; a number of algorithms are known, and are commercially available. Gene walk methods can be used to optimize the inhibitory activity of the siRNA.

The nucleic acid compositions can include both siRNA and modified siRNA derivatives, e.g., siRNAs modified to alter a property such as the pharmacokinetics of the composition, for example, to increase half-life in the body, as well as engineered RNAi precursors. The morpholino oligos can also be used for delivery of gene constructs.

shRNAs are be delivered into cells by methods known in the art, e.g., viral vectors, transduction, cationic liposome transfection, and can be delivered viaelectroporation. shRNA duplexes can be expressed within cells from engineered precursors, e.g., recombinant DNA constructs using mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the shNA transcript at a specific sequence. The shRNA is complementary to the sequence of the target gene in 5'-3' and 3'-5' orientations, and the two strands of the siRNA can be expressed in the same construct or in separate constructs. siRNAs, driven by H1 or U6 shRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing shRNA sequence under the control of T7 promoter also make functional shRNAs when transduced into the cells with a vector expression T7 RNA polymerase (Jacque (2002), supra). The vector constructs can further include plasmid vectors for transient transfection of cells.

Antisense and other compounds of the invention that hybridize to a miRNA or a mRNA are identified through routine experimentation. In general, the inhibitory nucleic acids must retain specificity for their target, i.e., must not directly bind to, or directly significantly affect expression levels of, transcripts other than the intended target.

Methods of introducing PARN shRNA and TRF4-2 shRNA into cells are described in Moon, Diane H., et al. "Poly (A)-specific ribonuclease (PARN) mediates 3 [prime]-end maturation of the telomerase RNA component," Nature genetics 47.12 (2015): 1482-1488; and Boyraz, Baris, et al. "Posttranscriptional manipulation of TERC reverses molecular hallmarks of telomere disease." The Journal of Clinical Investigation 126.9 (2016): 3377-3382, each of which is incorporated by reference in its entirety.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antibodies and Recombinant Fusion Proteins

Antibodies that specifically bind to TERC, PARN or TRF4-2 can be generated using standard methods known in the art. For example, a polyclonal antibody that specifically binds to a protein TERC, PARN or TRF4-2 can be generated by immunizing a mammal with the purified protein and isolating antibodies from the mammal that specifically bind to the purified protein. The antibodies used can be a monoclonal or polyclonal antibody. The antibodies administered can be an immunoglobulin G or immunoglobulin M. The antibodies administered can be chimeric (e.g., a humanized antibody) or a human antibody. The antibodies used can also be an antibody fragment (e.g., a Fab, F(ab')2, Fv, and single chain Fv (scFv) fragment).

Gene Therapy

The nucleic acids described herein, e.g., nucleic acids encoding TERC, TRF4-2, or PARN or active fragment thereof, or a nucleic acid encoding a protein or a RNA that modulates expression, level or activity of RNA or proteins associated with telomere size, can be incorporated into a construct to be used as a part of a gene therapy protocol. Patients can be identified by methods disclosed whereby gene alterations are first assessed, for example, diagnosed with a PARN deletion, or mutation, that leads to a telomere deficiency. Such patients can be used to draw or isolate cells from their body, and to test the efficacy of the gene constructs that will correct the alteration or mitigate the effects of genetic alteration. The methods include targeted expression vectors for in vitro transfection and expression of a polynucleotide, e.g., TRF4-2 and PARN, which can be translated into a gene construct for in vivo delivery e.g., via transfection or infection, into animal models, that mimic the cellular conditions identified in patient-derived cells, e.g., iPS cells. These constructs can encode a fusion polypeptide or active fragment thereof, or a protein, and alter the level or activity of TERC. They can also be delivered into cancer cells to treat cancers. Both cells and media can be collected for analysis.

One or more proteins listed in Table 4, and Examples, can also be administered to a subject for the treatment of a telomere disorder. Several methods are known in the art for the production of a fusion protein using molecular biology and cell culture techniques. In some embodiments, CRISPR based fusion proteins can be used to modulate TERC levels and or activity. For example, PARN protein encoded by a nucleic acid, can be ectopically transfected into a bacterial, yeast, or mammalian cell (using a protein expression plasmid or viral vector) that allows for the overexpression of the protein by the transfected cell. The transfected cells or the culture medium can be collected, and the recombinant protein or RNA can be isolated and purified using methods known in the art. The telomere associated proteins, e.g., TRF4-2 administered to the subject can contain a sequence having at least 80% (e.g., at least 85%, 90%, 95%, 96%, 97%, 98%, 99%, or 100%) identity to TRF4-2 or another protein in the TERC pathway, e.g., Table 4 and Experimental model FIG. 9. The fusion proteins administered to the subject can further include a modification (e.g., a polyethylene glycol or an HIV tat protein, or dCas9-or TET fusion or any other moiety that increases the cellular permeability of the inflammatory marker protein).

Expression constructs, e.g., expression constructs of telomere or associated genes, e.g., TRF4-2 and PARN, can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, or herpes simplex virus-1 virus vectors, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

In some embodiments, infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid. Retrovirus vectors, adenoviral and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems are art recognized. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses and adeno-associated viruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

In addition to viral transfer methods, such as those illustrated above, non-viral methods can also be employed to cause expression of a nucleic acid compound described herein (e.g., a nucleic acid or a nucleic acid encoding a compound that expression, levels or activity) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21):1867-74 (2000).

In some embodiments, a gene encoding a compound described herein, e.g., TERC or TRF4-2 or PARN or a compound modulating telomerase expression, level or activity, is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Pharmaceutical Compositions and Methods of Administration

The methods described herein include the use of pharmaceutical compositions comprising an agent that modulates the level or activity of TERC, PARN, or PAPD5 (e.g., PAPD5 shRNA). As used herein, an agent can be any number of agents, e.g., a small molecule, a nucleic acid, a polypeptide peptide, or a fragment thereof. In some embodiments, the agent can modulate the level or activity of PARN or PAPD5, e.g., a compound that can alter the level of a protein, e.g., PARN or PAPD5 protein (e.g., shRNA).

The terms "effective amount," "effective dose", and "effective to treat," as used herein, refer to an amount or a concentration of an agent, or composition comprising the agent, utilized for a period of time (including acute or chronic administration and periodic or continuous administration) that is effective within the context of its administration for causing an intended effect or physiological outcome.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Pharmaceutical compositions are typically formulated to be compatible with its intended route of administration into subjects. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Dosage

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays, e.g., human cell or cell lines. The cell based assays can employ patient-derived fibroblasts or iPS cells. A dose may be formulated in animal models to achieve a circulating plasma concentration range that includes the IC50 (i.e., the concentration of the test compound which achieves a half-maximal inhibition of symptoms) as determined in cell culture. A compound that is tested in a cell-based assay can display a low or high potency, defined by the range of concentration at which it is effective. The dosage of such compounds lies preferably within a range of circulating concentrations that include the IC50 with little or no toxicity. The dosage may vary within this range depending upon the dosage form employed and the route of administration utilized. Such information derived from initial cell based assays can be used to more accurately determine useful doses in humans. In some embodiments, prior to treatment, patients can be identified with genetic mutations, e.g., alterations in genes associated with telomere disease, and selected to be treated with composition, e.g., to treat telomere disease.

EXAMPLES

The disclosure further describes the following examples, which do not limit the scope of the invention.

Figure 2A:
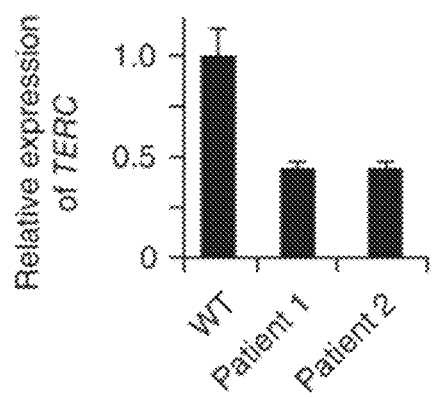
FIG. 2A is a graph showing quantitative PCR (qPCR) of TERC transcripts in patient and normal (WT) fibroblasts (n=2).
Figure 2B:
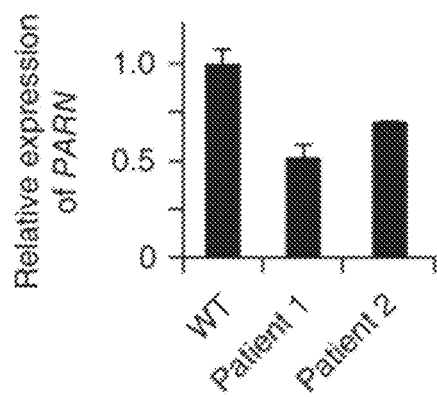
FIG. 2B is a graph showing qPCR of PARN transcripts in iPS cells (n=2).
Figure 2C:
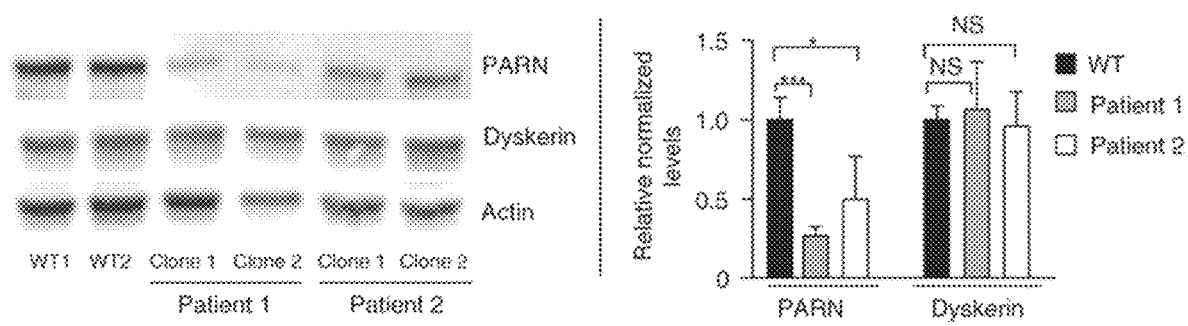
FIG. 2C is a photograph showing arepresentative western blot of PARN, dyskerin and actin proteins in iPS cells (left) and a graph showing quantitation of PARN and dyskerin protein levels normalized to actin (n=4; right).
Figures 2D, 2E, 2F, 2G:
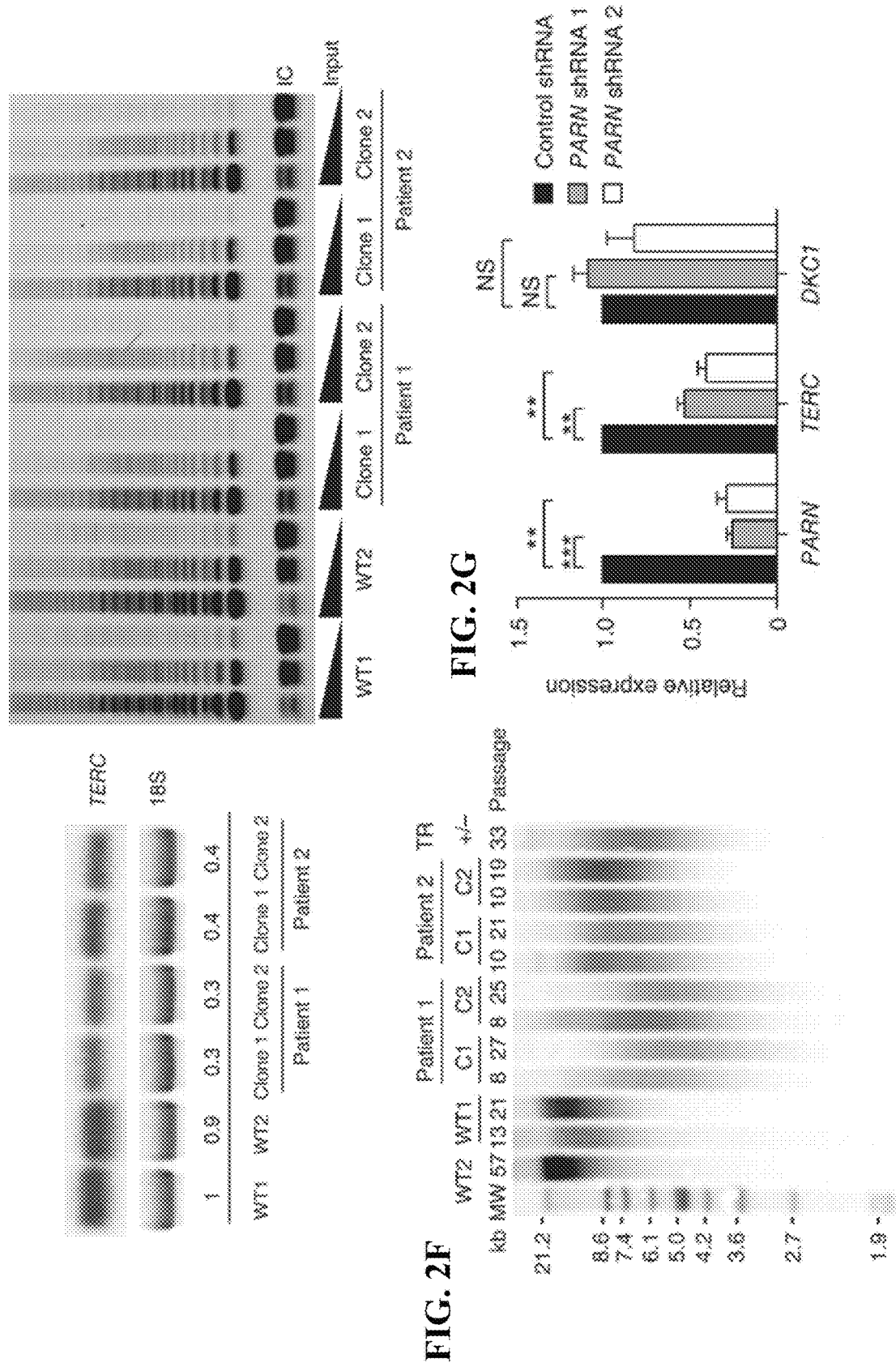
FIG. 2D is a photograph showing a Northern blot of TERC following denaturing agarose gel electrophoresis of RNA from iPS cells.
FIG. 2E is a photograph showing a telomerase activity (TRAP) assay for telomerase activity in iPS cells.
FIG. 2F is a photograph showing a Southern blot of telomere length by terminal restriction fragment length analysis in normal and patient iPS clones (cl), as well as control TERC haploinsufficient (TR+/−) iPS cells.
FIG. 2G is a graph showing a qPCR of PARN, TERC, and DKC1 transcripts from 293 cells transduced with lentivirus encoding shRNA directed against PARN versus luciferase as a control (ctrl) (n=3).

Example 1. Generation of iPS Cell Lines from Patients Identified with Short Telomeres Fibroblasts derived from patients with PARN mutations had decreased steady-state levels of TERC (FIG. 2A), not attributable to reduction in dyskerin protein. To overcome limitations of cell numbers and to study the effects of PARN mutations in telomerase-expressing cells, iPS cells from the fibroblasts of patients 1 and 2 with identified mutations and short telomere were generated and cultured in vitro for assessing TERC levels. These iPS cells showed PARN deficiency and reduced TERC levels compared to normal iPS cells, without diminished dyskerin protein (FIGS. 2C-2D). Furthermore, PARN-mutant iPS cells manifested decreased telomerase activity and impaired telomere elongation capacity compared to normal cells (FIGS. 2E-2F), but continuous self-renewal (>25 passages to date for all clones).

Figure 1B:
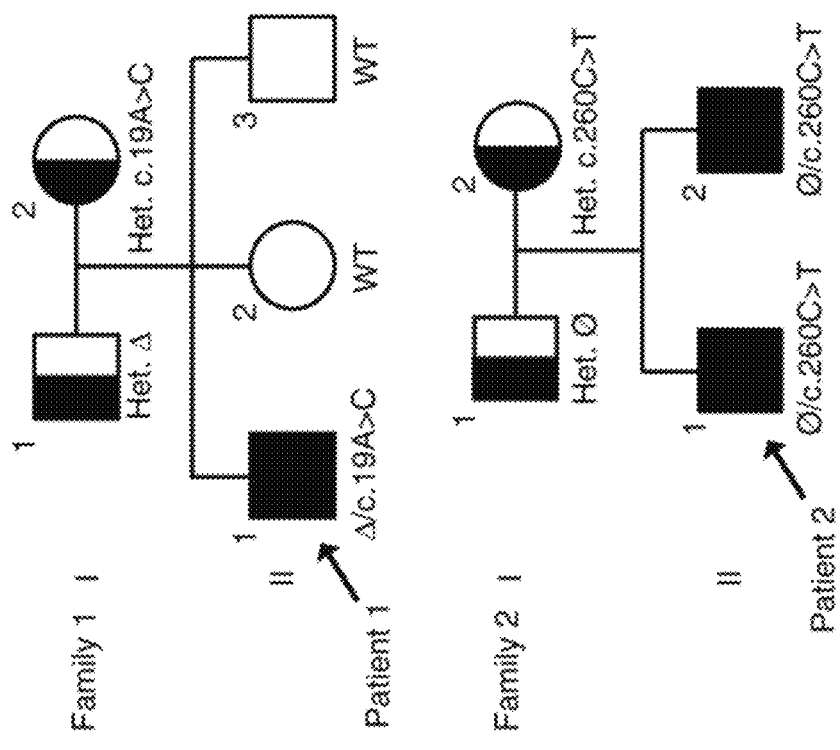
FIG. 1B is a graph showing flow cytometry-fluorescence assessment of telomere length measurement in lymphocytes (upper panel) and granulocytes (lower panel).
Figure 1C:
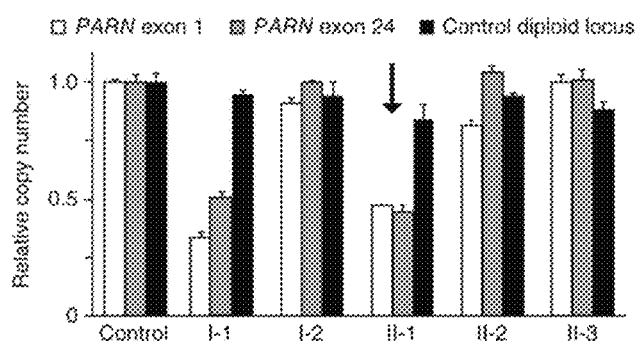
FIG. 1C is a graph showing quantitative PCR (qPCR) of peripheral blood genomic DNA from controls (ctrl) and members of family 1.
Figure 1D:
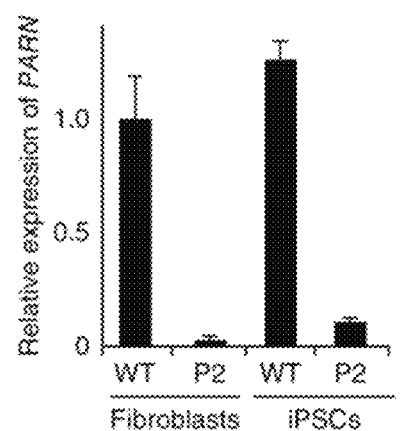
FIG. 1D is a graph showing a representative RT-PCR of cDNA using an allele-specific primer that distinguishes the wild type (WT; c.260C) versus mutant (c.260T) transcripts (n=2).

Example 2. Identification of Loss-of-Function Mutations in PARN in Patients from Two Families with Dyskeratosis Congenita (DC) and Short Telomeres By candidate gene sequencing in the subjects with genetically uncharacterized dyskeratosis congenita/telomere disease in the Pediatric Myelodysplastic Syndrome/Bone Marrow Failure registry at Boston Children's Hospital, biallelic defects in PARN in two families were identified (FIG. 1A), representing ~15% of the unrelated families in this disease category. The probands manifested classic features of dyskeratosis congenita and associated findings, including bone marrow failure and very short peripheral blood cell telomere length (Table 1 and FIG. 1B). Patient 1 was found to carry an undescribed missense variant c.19A>C on one allele, inherited from his mother, resulting in a substitution of a highly conserved amino acid p.Asn7His, and a large deletion encompassing the entire PARN gene on the other allele, inherited from his father (FIG. 1D and Table 2). The proband appears homozygous ("hom.") for c.19A>C and the father appears normal ("WT"). The proband manifests features of the Hoyeraal-Hreidarrson syndrome (HHS), a severe form of dyskeratosis congenita. Patient 2 was found to carry a heterozygous missense variant c.260C>T, encoding the substitution of a highly conserved amino acid, p.Ser87Leu, inherited from his unaffected mother (Table 2). He and his affected brother had no other potentially pathogenic exon-encoded variants. However, decreased PARN mRNA transcripts from the "normal" allele, indicated a non-coding defect on the allele inherited from his father (FIGS. 1D, and 2C). The proband, his affected brother and their unaffected mother are heterozygous for the variant. To explain this, expression of the individual alleles by RT-PCR of cDNA from the family members was investigated, which revealed a defect in accumulation of intact transcripts of the paternally-inherited allele in the brothers. RT-PCR of PARN exon 5 from cDNA shows expression of wild-type (c.260C) versus mutant (c.260T) alleles. The proband's mother shows equal representation of transcripts from both alleles, but the proband and affected brother show accumulation of transcripts predominantly from the mutant allele. The lack of detection of transcripts from the paternally-inherited allele by allele-specific qPCR (FIG. 1D) could be explained by alternative splicing that excludes exon 5. However, RT-PCR of cDNA from patient 2 fibroblasts and iPS cells reveals no major amplicon size variants that would indicate loss of exon 5 (*).

Figure 1E:
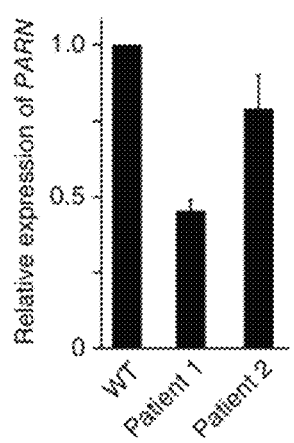
FIG. 1E is a graph showing a qPCR of PARN transcripts from patient and normal fibroblasts (n=3).
Figure 1F:
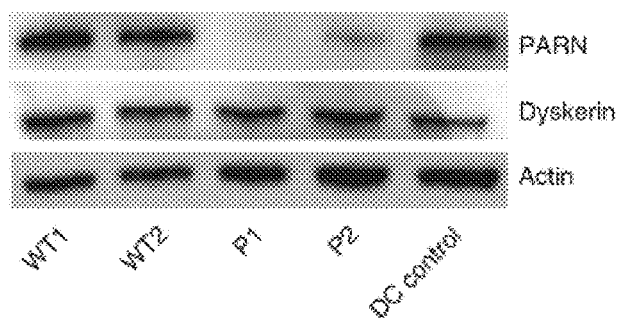
FIG. 1F is a photograph showing a representative Western blot of PARN, dyskerin and actin proteins in fibroblasts from normal individuals, patients 1 and 2 with PARN mutations, and a dyskeratosis congenita patient without PARN mutations (DC ctrl).

In keeping with these findings, PARN mRNA levels were diminished in fibroblasts from both patients (FIG. 1E), and PARN protein levels even more severely compromised (FIG. 1F). The primers used in sequencing PARN gene are compiled in Table 5. These data taken together show compound heterozygous loss-of-function mutations in PARN in two families with dyskeratosis congenita (DC) and very short telomeres can be detected. Diminished TERC levels can result from disruption of dyskerin, which binds and stabilizes TERC, but cells from these patients did not carry mutations in DKC1 nor demonstrate reductions in dyskerin protein (FIG. 1F).

The following methods are used in the Examples.

Patient Material

The probands and families were enrolled in the Pediatric Myelodysplastic Syndrome and Bone Marrow Failure registry at Boston Children's Hospital. Biological samples were procured under protocols approved by the Institutional Review Board at Boston Children's Hospital, and after written informed consent in accordance with the Declaration of Helsinki.

Telomere Length Measurements

By using Flow-FISH technique, telomere length in peripheral blood cell subsets was measured by flow cytometry-fluorescence in situ hybridization by Repeat Diagnostics, Vancouver, B. C.

Primary Cells and Cell Lines

Fibroblasts were cultured from skin biopsies obtained from patients and healthy volunteer subjects under approved protocols. Briefly 2 mm punch biopsies were diced and placed under a coverslip in DMEM media with 15% fetal calf serum (FCS) until keratinocyte and fibroblast outgrowths were apparent. Fibroblasts were sub-cultured and expanded using trypsin 0.05% and DMEM 15% FCS. Normal skin fibroblasts used in these experiments were from a healthy adult volunteer. HEK 293 (293) cells were sub-cultured and expanded using trypsin 0.05% and DMEM 10% FCS. Derivation, characterization, and culture conditions of iPS cells from fibroblasts for patient 1 was performed as described. NHSF2 and patient 2 fibroblasts were reprogrammed using the 4-in-1-dTomato lentiviral reprogramming vector. "WT1" iPS cells are derived from NHSF2. For feeder-free culture, iPS cells were maintained in Essential 8 medium (Life Technologies, Carlsbad, Calif.) on hES-qualified Matrigel matrix (BD Biosciences, San Jose, Calif.).

Northern Blots

Formaldehyde/agarose gel electrophoresis. 4-10 µg of total RNA was separated on 1.5% agarose/formaldehyde gels, transferred to Hybond N+ membranes (Amersham) in 10×SSC by capillary transfer, and hybridized with α-32P-dCTP-labeled full-length TERC probe in ULTRAhyb buffer (Life Technologies, Carlsbad, Calif.). Signals were normalized to 18S rRNA based on ethidium bromide staining. Quantification was performed using ImageJ.

TERC RNA Decay 0.5-1×106 iPS cells or 293 cells were treated with 5 µg/ml of actinomycin D (Life Technologies, Carlsbad, Calif.) and harvested in TRIzol at 0, 1, 2, and 4 hours following treatment. Purified RNA was subjected to Northern blot by 1.5% formaldehyde/agarose gel electrophoresis, and transferred to nylon membranes and hybridized as described above. TERC signals were normalized to 18S rRNA. Decay slopes were determined by simple linear regression and transcript half-life was calculated as the x-intercept at y=0.5, using GraphPad Prism.

Telomerase Activity Assay 293 and iPS cells were lysed in CHAPS lysis buffer and protein was quantified by the Bradford assay (Bio-Rad, Hercules, Calif.). Three-fold dilutions (90 ng, 45 ng and 15 ng) of cell extracts were subjected to the telomere repeat amplification protocol (TRAP) using the TRAPeze Telomerase Detection kit (Millipore, Billerica, Mass.). Products were resolved on 10% TBE polyacrylamide gels and visualized by staining with GelRed (Biotium, Fremont, Calif.).

3' Rapid Amplification of cDNA Ends (RACE)

500 ng of total RNA was ligated to 5 µM of 5'-adenylated, 3'-blocked adapter (Universal miRNA cloning linker, New England Biolabs, Ipswich, Mass.) with 280 units of T4 RNA ligase truncated KQ (New England Biolabs, Ipswich, Mass.), 25% PEG 8000, and 1 µl RNaseOUT (Life Technologies, Carlsbad, Calif.) in a 20 μl reaction at 25 degrees C. for 16¬¬-24 hr. After cleanup with RNA Clean and Concentrator columns (Zymo Research), followed by DNase treatment, cDNA was synthesized with 5 pmol of universal RT primer and SuperScript III. PCR amplification was carried out using 5 μM of TERC_L/universal RT primer sets (Table 6) with SsoAdvanced Universal SYBR Green Supermix (Bio-Rad, Hercules, Calif.). PCR products were directly analyzed run on 3% agarose gels to visualize mature and extended TERC transcripts.

Lentiviral RNA Interference and cDNA Expression of TRF4-2

Short-hairpin RNA (shRNA) constructs. Duplex oligonucleotides encoding shRNA targeting human TRF4-2 (ENA accession number: FR872509) and human PARN (NM_002582) or luciferase control (Table 6) were cloned into the pLKO.1-puro vector (Addgene #10878), and pLKO.1-blast vector (Addgene #26655). Lentiviral vector production and transduction of cells.

Lentiviral vectors encoding shRNAs were produced by co-transfection of 293 cells with lentiviral plasmids described above, pCMV_dR8.91 and pCMV_VSV-G, using branched polyethylenimine (Sigma). Supernatants were harvested, filtered and frozen in aliquots on days 3-4 following transfection. For knockdown experiments, cells were transduced with lentivirus and harvested 6 days after selection in puromycin (2 μg/ml for 293 cells; 0.2 μg/ml for iPS cells) or blasticidin (10 μg/ml for 293 cells). The primers used to amplify transcripts specific to TRF4-2 (i.e., PAPD5) and RNA interference constructs are shown in Table 8, and includes the shRNA constructs PAPD5 shRNA1 and PAPD5 shRNA2, that knocked-down PAPD5 to significant levels and restored the TERC levels in their presence in fibroblasts and patient-derived cells.

Terminal Restriction Fragment (TRF) Length Analysis.

1.8 μg of genomic DNA was digested with HinfI/RsaI restriction enzymes and separated on 0.8% agarose gels, followed by Southern blot using the TeloTAGGG telomere length assay kit (Roche, Basel, Switzerland).

DNA Sequencing and Genetic Analysis

DNA isolation and sequencing. Genomic DNA from primary cells and cell lines was extracted using Gentra Puregene kit (Qiagen). DNA from research subject saliva samples was extracted with prepIT kit (Oragene DNA Genotek). Primers for PARN gene amplification and sequencing are provided in Table 5. Sanger sequencing was performed by Genewiz.

Copy Number Determination by Quantitative PCR (qPCR)

PARN locus copy number in fibroblast, peripheral blood or saliva genomic DNA from family 1 was determined by performing qPCR using primers spanning PARN exon 1, PARN exon 24, and a control diploid locus (GPR15) (PARNcopy_ex1L/R; PARNcopy_ex24L/R; GPR15copy_L/R; Table 6). A standard curve was generated for each primer pair and used to calculate relative copy number of each PARN amplicon, calibrated to GPR15. Quantification results were normalized to genomic DNA from a healthy volunteer.

Genome-Wide SNP Microarray Analysis.

Microarray analysis was performed on peripheral blood DNA from patient 1 using the Infinium Assay with the Illumina CytoSNP-850K BeadChip platform by the Cytogenetics program, Cincinnati Children's Hospital Medical Center.

RNA Isolation, cDNA Synthesis and Quantitative RT-PCR

RNA from patient blood samples was processed using the PAXgene blood RNA kit (Qiagen). RNA from cultured cells was recovered using TRIzol (Ambion). After DNase treatment (Turbo DNA-free, Ambion), cDNA was synthesized using 1 μg of total RNA, 50 ng random hexamers or 7.5 ng oligo(dT)10, and 1 μl SuperScript III Reverse Transcriptase (Invitrogen, Carlsbad, Calif.) in a total volume of 20 μl for 1 hr at 50° C. qPCR was performed using SsoAdvanced Universal SYBR Green Supermix (Bio-Rad, Hercules, Calif.) and primers in Table 6 (PARN_L/R, TERC_L1/R1, DKC1_L/R, POLR2A_L/R, ACTB_L/R) in a CFX96 Real-Time PCR detection system (Bio-Rad, Hercules, Calif.). Quantification of PARN, TERC, and DKC1 was normalized to POLR2A and/or ACTB, which in direct comparisons gave similar results. Graphing and statistical analysis of qPCR results were performed using GraphPad Prism. Sequences of primers used for wild type allele-specific qPCR of the PARN gene in patient 2 (PARNcDNA_ex3L, PARNcDNA_ex5RWT), and for cDNA sequencing of PARN transcripts from peripheral blood cell cDNA from family 2 (PARNcDNA_ex4L, PARNcDNA_ex6R) are provided in Table 6.

To estimate the proportion of TERC that is oligo-adenylated relative to total TERC (FIG. 3B), standard curves were generated for TERC amplification using hexamer-primed cDNA and oligo(dT)¬10-primed cDNA, after normalizing to ß-actin. Oligo(A) TERC levels were derived from oligo(dT)¬10-primed cDNA, and represented as a percentage of total TERC levels which were derived from hexamer primed cDNA. Primers: TERC_L/R, ACTB_L/R (Table 6).

Denaturing polyacrylamide gel electrophoresis of in vitro transcribed TERC specific amplicons Formaldehyde/agarose gel electrophoresis. 4-10 μg of total RNA was separated on 1.5% agarose/formaldehyde gels, transferred to Hybond N+ membranes (Amersham) in 10×SSC by capillary transfer, and hybridized with α-32P-dCTP-labeled full-length TERC probe in ULTRAhyb buffer (Life Technologies, Carlsbad, Calif.). Signals were normalized to 18S rRNA based on ethidium bromide staining. Quantification was performed using ImageJ.

Denaturing polyacrylamide gel electrophoresis (PAGE). 1-2 μg of total RNA was separated on 5% polyacrylamide-TBE/Urea gels, transferred to Hybond N+ membranes by electroblotting, and hybridized with α-32P-dCTP-labeled full-length TERC or U1 snRNA probes. 20 pg of in vitro-transcribed TERC RNA was loaded as a control. Signals were normalized to U1 snRNA. Quantification was performed using ImageJ. Primers used to amplify probes are TERC: TERC_L4/TERC_R2; U1: U1snRNA_L/U1snRNA_R (Table 6).

In Vitro Transcription of TERC RNA

Full-length TERC transcripts used for denaturing PAGE/Northern blots were generated by in vitro transcription using a T7-promoter-TERC PCR amplicon template (MAXIscript T7, Life Technologies, Carlsbad, Calif.). Primers used to generate the T7-promoter-TERC template: T7_TERC_L/TERC_R2 (Table 6).

TERC RNA Decay to Determine Stability of TERC mRNA 0.5-1×106 iPS cells or 293 cells were treated with 5 μg/ml of Actinomycin D (Life Technologies, Carlsbad, Calif.) and harvested in TRIzol at 0, 1, 2, and 4 hours following treatment. Purified RNA was subjected to Northern blot by 1.5% formaldehyde/agarose gel electrophoresis, and transferred to nylon membranes and hybridized as described above. TERC signals were normalized to 18S rRNA. Decay slopes were determined by simple linear regression and transcript half-life was calculated as the x-intercept at y=0.5, using GraphPad Prism.

Telomerase Activity Assay (TRAP Assay)

2×105 iPS cells were lysed in CHAPS lysis buffer and protein was quantified by the Bradford assay (Bio-Rad, Hercules, Calif.). Five-fold dilutions (100 ng, 20 ng and 4 ng) of cell extracts were subjected to the telomere repeat amplification protocol (TRAP) using the TRAPeze Telomerase Detection kit (Millipore, Billerica, Mass.). Products were resolved on 10% TBE polyacrylamide gels and visualized by staining with GelRed (Biotium, Fremont, Calif.).

3' Rapid Amplification of cDNA Ends (RACE) of TERC 600 ng of total RNA was ligated to 5 µM of 5'-adenylated, 3'-blocked adapter (Universal miRNA cloning linker, New England Biolabs, Ipswich, Mass.) with 280 units of T4 RNA ligase truncated KQ (New England Biolabs, Ipswich, Mass.), 25% PEG 8000, and 1 µl RNaseOUT (Life Technologies, Carlsbad, Calif.) in a 20 µl reaction at 25 degrees C. for 16-24 hr. After cleanup with RNA Clean and Concentrator columns (Zymo Research, Irvine, Calif.), followed by DNase treatment, cDNA was synthesized with 5 pmol of universal RT primer and SuperScript III. PCR amplification was carried out using 5 µM of TERC_L2/universal RT or TERC_L3/universal RT primer sets (Table 6) with SsoAdvanced Universal SYBR Green Supermix (Bio-Rad, Hercules, Calif.). PCR products were directly analyzed run on 2.5% agarose gels to visualize mature and extended TERC transcripts, or subject to Qiaquick PCR purification columns (Qiagen, Hilden, Germany) for library preparation for deep sequencing. For Sanger sequencing, 3' RACE PCR products were directly cloned into the pCR4_TOPO vector (Life Technologies, Carlsbad, Calif.), and individual clones were sequenced using the TERC_L2 or TERC_L3 primers.

MiSeq Library Preparation and Analysis for Mapping of TERC End Processing by Sanger Sequencing RACE products were prepared for deep sequencing using the TruSeq Nano DNA LT Library Prep Kit (Illumina, San Diego, Calif.). Briefly, for each sample, linkers carrying unique barcodes were ligated to RACE products with DNA ligase, amplified using Illumina adapters, and size selected using magnetic beads (Ampure). The completed libraries were submitted to the Tufts University Genomics Core for sequencing and data analysis. The quality and quantity of each library was determined on an Advanced Analytical Fragment Analyzer. The libraries were then pooled to equimolar concentrations. The pooled library was sequenced on an Illumina MiSeq with paired-end 250 bases using the Illumina TruSeq V2 500 cycles kit. The reads were demultiplexed with CASAVA 1.8.2 and the read 1 and read 2 fastq files for each sample were generated. For data analysis, the Illumina adapter sequence was first removed from the end of each read using Trimmomatic50. The resulting unbroken pair was then joined using FLASH51. The joined-reads from each sample were then mapped to the TERC gene (NR_001566; SEQ ID NO: 99) with the Bowtie2 mapper52, and outputted to a SAM file. The SAM file from each sample was then used as input for custom developed Perl scripts to remove the 3' RACE universal adapter sequence, determine the position at which the genomic sequenced ended, and the position and length of the oligo(A) tail. Code availability: Perl scripts for TERC RNA end analysis will be made available upon request.

RNA-Seq Library Preparation and Analysis for Transcriptome Profiling for Estimation of Non-Coding and Protein Coding RNAs RNA integrity was verified using the Advanced Analytical Fragment Analyzer (FA). 0.5-1 µg of total RNA was used as input for library preparation using TruSeq Stranded Total RNA with RiboZero Gold kit (Illumina, San Diego, Calif.). The molar concentrations of the libraries were determined using the FA, and pooled at equimolar concentrations. The pooled libraries were sequenced on two lanes of HiSeq 2500 High Output single read 50 bases format. Sequence reads were aligned to the human transcriptome using HISAT version 0.1.653. The transcriptome file consisted of protein-coding and ncRNA sequences downloaded from ENSEMBL (release 80). To estimate transcript abundances, Salmon version 0.3.254 was applied to the aligned reads and summarized transcript abundances into gene-level expression levels by summing all transcript expression levels mapping to the same gene. Gene-to-transcript mappings, and transcript type annotations (e.g., assignment of transcript to categories such as snRNA, snoRNA, etc.) were downloaded also from ENSEMBL. Auto-annotation was manually adjusted by annotating TERC and other scaRNAs as snoRNAs, for the purpose of this analysis.

Two approaches were undertaken to find genes that were commonly differentially expressed between normal and PARN-deficient cell lines. First, the Wilcoxon signed-rank test was performed on the 13,508 genes that had expression levels of at least 1 transcripts per million (TPM) in one sample, using the following pairs of samples: WT1 FIB versus Patient 1 FIB; WT1 IPS versus Patient 1 c12 iPS; WT2 iPS versus Patient 2 cl1 iPS; 293 control KD versus 293 PARN KD. No genes were nominally significantly differentially expressed across all pairs using this approach, or using the paired t-test. Second, because TERC levels are decreased in PARN-deficient cell lines by quantitative RT-PCR and Northern blot, it was reasoned that its fold change magnitude would be an appropriate threshold to define other genes as differentially expressed in a paired comparison manner. The comparison-specific thresholds in absolute values, which was referred to as TERC-defined thresholds, are provided in Table 7. Only one transcript, a snoRNA (SCARNA13), showed a fold-change in all 7 comparisons to an extent exceeding TERC (Table 4). The stringency of the ad hoc metric of differential expression was lessened, by allowing genes to be considered differentially expressed if they exceeded TERC-defined thresholds in fewer (5 or 6) than all 7 pairwise comparisons. In this analysis, the question was whether the number of genes in each category of transcript was different than would be expected by chance given the total number of genes differentially expressed using the Chi-squared test (Table 3).

Western Blot Analysis

Total cellular lysates were subjected to SDS-PAGE and transfer to PVDF membranes using standard procedures. Detection of PARN and dyskerin was performed using primary antibodies to human PARN (Abcam ab-188333, dilution 1:5000) and dyskerin (Santa Cruz sc-48794, dilution 1:1000) and horseradish peroxidase (HRP)-conjugated goat anti-rabbit secondary antibody (Biorad 170-5046, dilution 1:15,000), followed by chemiluminescent detection using Clarity Western ECL substrate (Biorad, Hercules, Calif.). Protein loading was determined using HRP-conjugated actin antibodies (Santa Cruz sc-1615, dilution 1:1000) on the same membranes and used for normalization. Imaging and quantification of chemiluminescent signals was performed using the Biorad ChemiDoc Touch imaging system. Graphing and statistical analyses were performed using GraphPad Prism.

Short-Hairpin RNA (shRNA) Constructs

Duplex oligonucleotides encoding shRNA targeting human PARN (NM_002582) or luciferase control (Table 6) were cloned into the pLKO.1-puro vector (Addgene #10878).

cDNA expression constructs. cDNAs encoding the PARN open reading frame (NM_002582; bases 147-2066) or enhanced green fluorescent protein (EGFP) were PCR amplified and cloned into the BsrGI/AgeI sites of pLX301 (puromycin resistance; Addgene plasmid #25895) and pLX304 (blasticidin resistance; Addgene plasmid #25890).

Lentiviral vector production and transduction. Lentiviral vectors encoding shRNAs and cDNAs were produced by co-transfection of 293T cells with lentiviral plasmids described above, pCMV_dR8.91 and pCMV_VSV-G, using branched polyethylenimine (Sigma, St. Louis, Mo.). Supernatants were harvested, filtered and frozen in aliquots on days 3-4 following transfection. cDNA expressing lentiviral vectors were concentrated by centrifugation. Titers, knockdown efficiency, and cDNA expression were determined by infecting 293T cells for 16-24 hrs using varying quantities of viral supernatant in the presence of 10 µg/ml protamine sulfate. After 24-36 hr, infected cells were selected with 2 µg/ml of puromycin or 10 µg/ml of blasticidin for 3-5 days and RNA and/or protein was harvested for analysis. For knockdown experiments, cells were transduced with lentivirus and harvested 5-6 days after selection in puromycin (2 µg/ml for 293 cells; 1 µg/ml for fibroblasts; 0.2 µg/ml for iPS cells). For rescue experiments, control or knockdown cells that were selected for 5-6 days after shRNA transduction were infected with pLX304-based lentiviral vectors expressing PARN or EGFP, and harvested 4 days after selection in blasticidin (10 µg/ml for 293 cells; 5 µg/ml for fibroblasts).

Patient Material Used for TRF4-2 Studies

Biological samples were procured under protocols approved by the Institutional Review Board at Boston Children's Hospital, and after written informed consent in accordance with the Declaration of Helsinki.

Primary Cells and Cell Lines for TRF4-2 Studies

Fibroblasts were cultured from skin biopsies obtained from patients and healthy volunteer subjects under approved protocols. Briefly 2 mm punch biopsies were diced and placed under a coverslip in DMEM media with 15% fetal calf serum (FCS) until keratinocyte and fibroblast outgrowths were apparent. Fibroblasts were sub-cultured and expanded using trypsin 0.05% and DMEM 15% FCS. Normal skin fibroblasts used in these experiments were from a healthy adult volunteer: NHSF2. HEK 293 (293) cells were sub-cultured and expanded using trypsin 0.05% and DMEM 10% FCS. Derivation, characterization, and culture conditions of iPS cells from fibroblasts for patient 1 was performed as described. NHSF2 and patient 2 fibroblasts were reprogrammed using the 4-in-1-dTomato lentiviral reprogramming vector. "WT1" iPS cells are derived from NHSF2. For feeder-free culture, iPS cells were maintained in Essential 8 medium (Life Technologies, Carlsbad, Calif.) on hES-qualified Matrigel matrix (BD Biosciences, San Jose, Calif.).

RNA Isolation, cDNA Synthesis and Quantitative RT-PCR

RNA from cultured cells was recovered using TRIzol (Ambion). After DNase treatment (Turbo DNA-free, Ambion), cDNA was synthesized using 1 µg of total RNA, 50 ng random hexamers or 7.5 ng oligo(dT)10, and 1 µl SuperScript III Reverse Transcriptase (Invitrogen, Carlsbad, Calif.) in a total volume of 20 µl for 1 hr at 50° C. qPCR was performed using SsoAdvanced Universal SYBR Green Supermix (Bio-Rad, Hercules, Calif.) and primers in Table 5, 6 and 8 (PARN_L/R, TRF4-2_L/R, POLR2A_L/R) in a CFX96 Real-Time PCR detection system (Bio-Rad, Hercules, Calif.). Quantification of TRF4-2 and PARN was normalized to POLR2A.

Graphing and statistical analysis of qPCR results were performed using GraphPad Prism.

Northern Blots

Formaldehyde/agarose gel electrophoresis. 4-10 µg of total RNA was separated on 1.5% agarose/formaldehyde gels, transferred to Hybond N+ membranes (Amersham) in 10×SSC by capillary transfer, and hybridized with $\alpha$-$^{32}$P-dCTP-labeled full-length TERC probe in ULTRAhyb buffer (Life Technologies, Carlsbad, Calif.). Signals were normalized to 18S rRNA based on ethidium bromide staining. Quantification was performed using ImageJ.

TERC RNA Decay 0.5-1×10$^6$ iPS cells or 293 cells were treated with 5 µg/ml of actinomycin D (Life Technologies, Carlsbad, Calif.) and harvested in TRIzol at 0, 1, 2, and 4 hours following treatment. Purified RNA was subjected to Northern blot by 1.5% formaldehyde/agarose gel electrophoresis, and transferred to nylon membranes and hybridized as described above. TERC signals were normalized to 18S rRNA. Decay slopes were determined by simple linear regression and transcript half-life was calculated as the x-intercept at y=0.5, using GraphPad Prism.

Telomerase Activity Assay 293 and iPS cells were lysed in CHAPS lysis buffer and protein was quantified by the Bradford assay (Bio-Rad, Hercules, Calif.). Three-fold dilutions (90 ng, 45 ng and 15 ng) of cell extracts were subjected to the telomere repeat amplification protocol (TRAP) using the TRAPeze Telomerase Detection kit (Millipore, Billerica, Mass.). Products were resolved on 10% TBE polyacrylamide gels and visualized by staining with GelRed (Biotium, Fremont, Calif.). 3' Rapid Amplification of cDNA Ends (RACE) 500 ng of total RNA was ligated to 5 µM of 5'-adenylated, 3'-blocked adapter (Universal miRNA cloning linker, New England Biolabs, Ipswich, Mass.) with 280 units of T4 RNA ligase truncated KQ (New England Biolabs, Ipswich, Mass.), 25% PEG 8000, and 1 µl RNaseOUT (Life Technologies, Carlsbad, Calif.) in a 20 µl reaction at 25 degrees C. for 16-24 hr. After cleanup with RNA Clean and Concentrator columns (Zymo Research), followed by DNase treatment, cDNA was synthesized with 5 pmol of universal RT primer and SuperScript III. PCR amplification was carried out using 5 µM of TERC_L/universal RT primer sets (Table 6) with SsoAdvanced Universal SYBR Green Supermix (Bio-Rad, Hercules, Calif.). PCR products were directly analyzed run on 3% agarose gels to visualize mature and extended TERC transcripts.

Lentiviral RNA Interference and cDNA Expression short-hairpin RNA (shRNA) constructs. Duplex oligonucleotides encoding shRNA targeting human TRF4-2 (ENA accession number: FR872509; SEQ ID NO: 2) and human PARN (NM_002582; SEQ ID NO: 1) or luciferase control (Table 6) were cloned into the pLKO.1-puro vector (Addgene #10878), and pLKO.1-blast vector (Addgene #26655).

Lentiviral vector production and transduction. Lentiviral vectors encoding shRNAs were produced by co-transfection of 293 cells with lentiviral plasmids described above, pCMV_dR8.91 and pCMV_VSV-G, using branched polyethylenimine (Sigma). Supernatants were harvested, filtered and frozen in aliquots on days 3-4 following transfection. For knockdown experiments, cells were transduced with lentivirus and harvested 6 days after selection in puromycin (2 µg/ml for 293 cells; 0.2 µg/ml for iPS cells) or blasticidin (10 µg/ml for 293 cells).

Example 3. Knocking Down PARN in Cell Lines Reduces TERC Levels

Figure 2H:
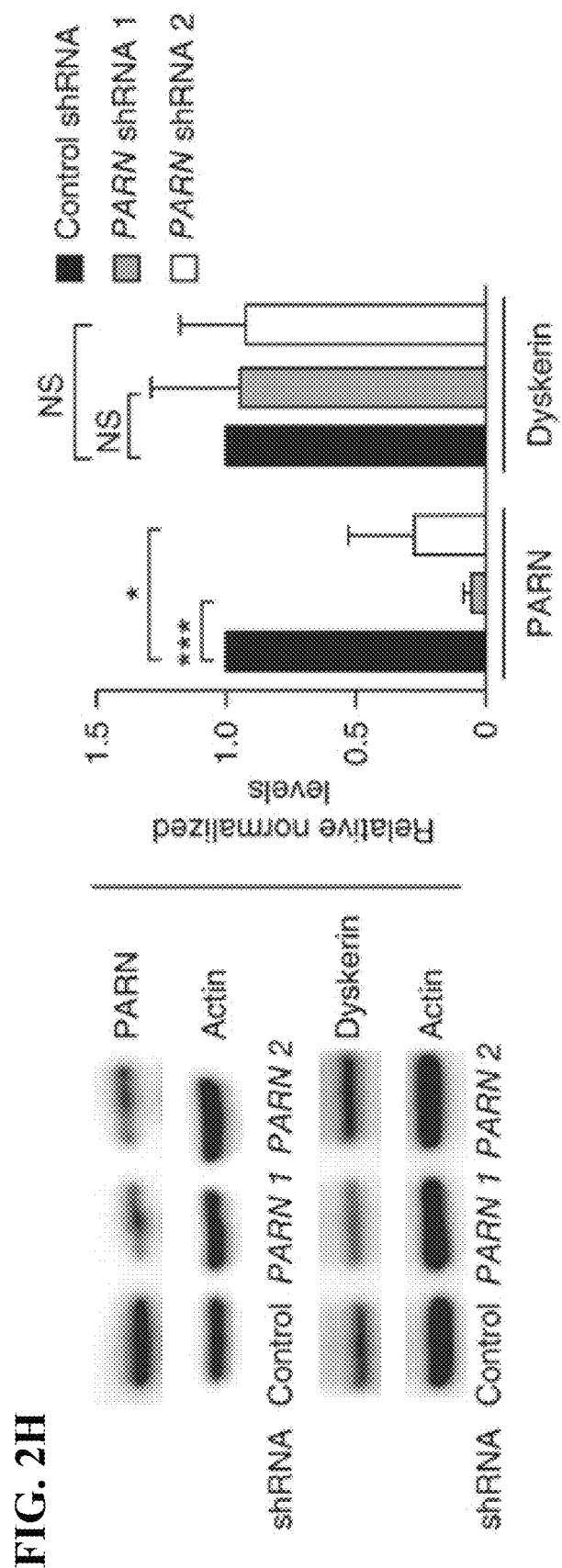
FIG. 2H is a photograph showing a representative western blot of PARN, dyskerin and actin proteins in 293 cells transduced with lentivirus encoding shRNA directed against PARN versus luciferase (left).

To further investigate how PARN affects TERC levels, PARN was knocked down in HEK293 (293) cells, and again showed reductions in TERC levels but not DKC1 or dyskerin (FIGS. 2G-2H). In FIG. 2H, quantitation of PARN and dyskerin protein levels normalized to actin (n=4; right). For all panels, error bars represent standard deviations and significance is indicated by p-values (*≤0.05; ≤0.01; *≤0.001; n.s. not significant). These studies demonstrate that PARN deficiency results in diminished TERC levels independent of DKC1/dyskerin, as well as deficits in telomerase activity and telomere maintenance. Table 6 shows the 2 sh RNA constructs (SEQ ID NO: 74 and 75) used for PARN knockdown among primers and constructs that were generated to investigate the role of PARN in cell lines specifically manipulated using vector constructs that comprise PARN specific shRNAs. It also reveals the PARN-specific primers that were used to amplify regions of PARN locus to measure alteration in PARN levels and further used the cells with deficiency of PARN to compare TERC levels to the reference level found HEK293 or 293 fibroblast cells.

Example 4. PARN Deficiency Results in Abnormal TERC RNA Species with Modified Tails in Patient Derived Cells (iPS) and Cell Lines (293 Fibroblasts)

Box H/ACA snoRNAs are intron-encoded and undergo maturation by exonucleolytic processing of spliced intermediates. Nascent snoRNAs are subject to oligo-adenylation by TRF4-2, a component of the TRAMP (TRF4-2, AIR2, MTR4) complex, which stimulates degradation of nuclear RNAs by the exosome. PARN counteracts snoRNA oligo-adenylation and promotes 3' end maturation, which may prevent further TRAMP-mediated oligo(A) addition and subsequent degradation8. TERC is transcribed by RNA polymerase II (pol II) as an autonomous genetic unit. It has a 7-methylguanosine cap and a precise 3' end, but unlike other pol II transcripts, TERC RNA does not contain a long poly(A) tail, and the mechanisms of its 3' end maturation are unknown. Based on the box H/ACA architecture shared between snoRNAs and TERC, and the recent finding that TERC exists in oligo(A)-containing forms, it was hypothesized that PARN participates in TERC 3' end maturation and stabilization by removing oligo(A) in nascent transcripts.

The presence of oligo(A) forms of TERC by oligo(dT) 10-priming of total RNA was verified for cDNA synthesis (FIG. 3A), and compared the relative proportions of oligo (A) versus total TERC. It was found a higher proportion of oligo(A) TERC in PARN mutant fibroblasts and iPS cells compared to normal cells (FIG. 3B).

Figures 3E, 3F:
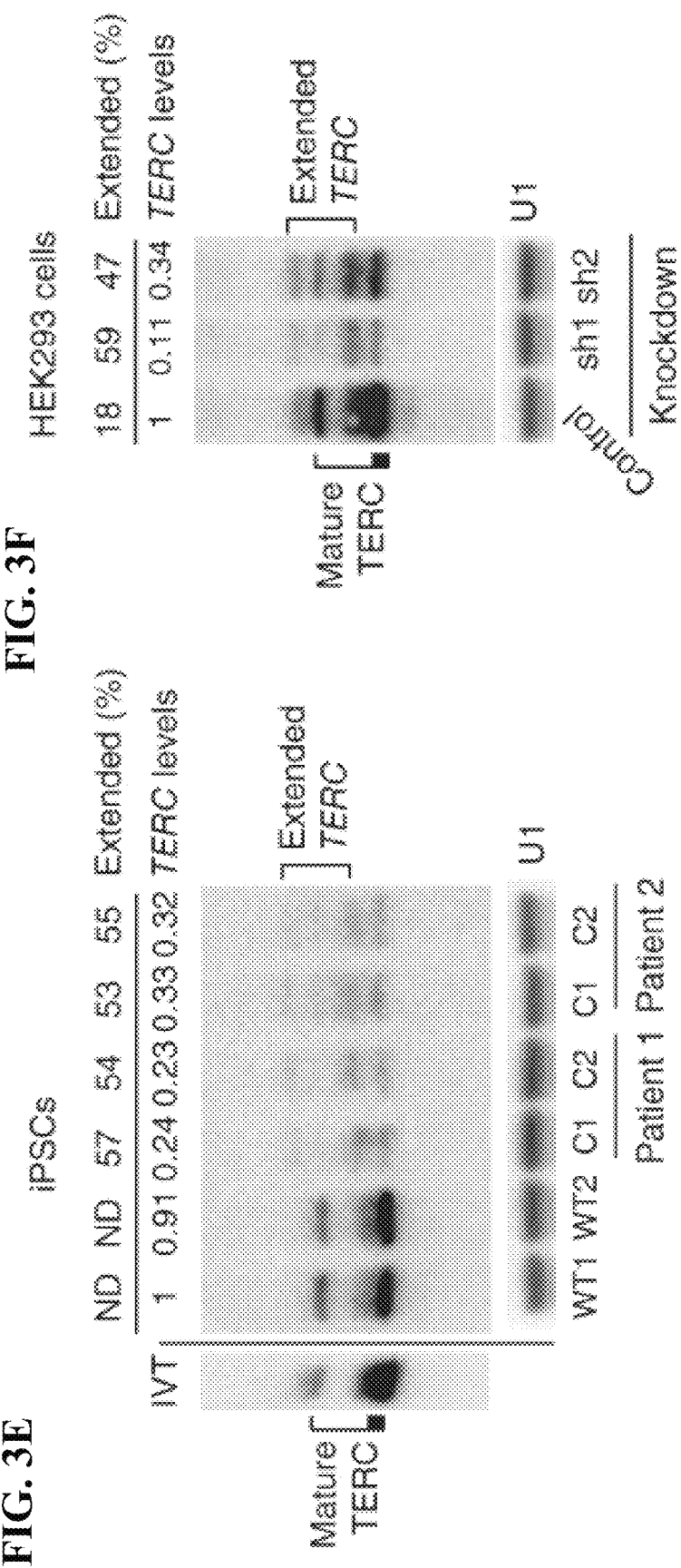
FIG. 3E is a photograph showing a Northern blot of TERC using RNA from iPS cells, separated by denaturing polyacrylamide gel electrophoresis. U1 snRNA represents loading control.
FIG. 3F is a photograph showing a Northern blot of TERC using RNA from 293 cells subjected to shRNA-mediated knockdown of PARN (sh) versus luciferase.

Because TERC oligo(A) tails average 6-7 nucleotides in length and may not be quantified accurately using oligo(dT), 3' rapid amplification of cDNA ends (RACE) was performed (FIG. 3C). The data shows a significant alteration in the size distribution of TERC 3' ends in both patient fibroblasts and iPS cells compared to normal cells, in that the intensity of the amplicon at the expected size was reduced, and larger, extended transcripts predominated (FIG. 3D). These results were recapitulated in 293 cells upon transient PARN knockdown (FIG. 3D). By Northern blot using denaturing polyacrylamide gels, in vitro transcribed TERC and endogenous, mature TERC transcripts migrate as multiple bands. In addition to these, slowly migrating species in PARN-deficient cells were discovered, in a high proportion (~50%) of total TERC compared to normal cells, which are likely to represent the extended TERC transcripts (FIGS. 3E-3F). These data indicate that PARN deficiency results not only in diminished TERC steady-state levels but also in increased TERC RNA species with abnormal 3' ends or tails.

Figure 7:
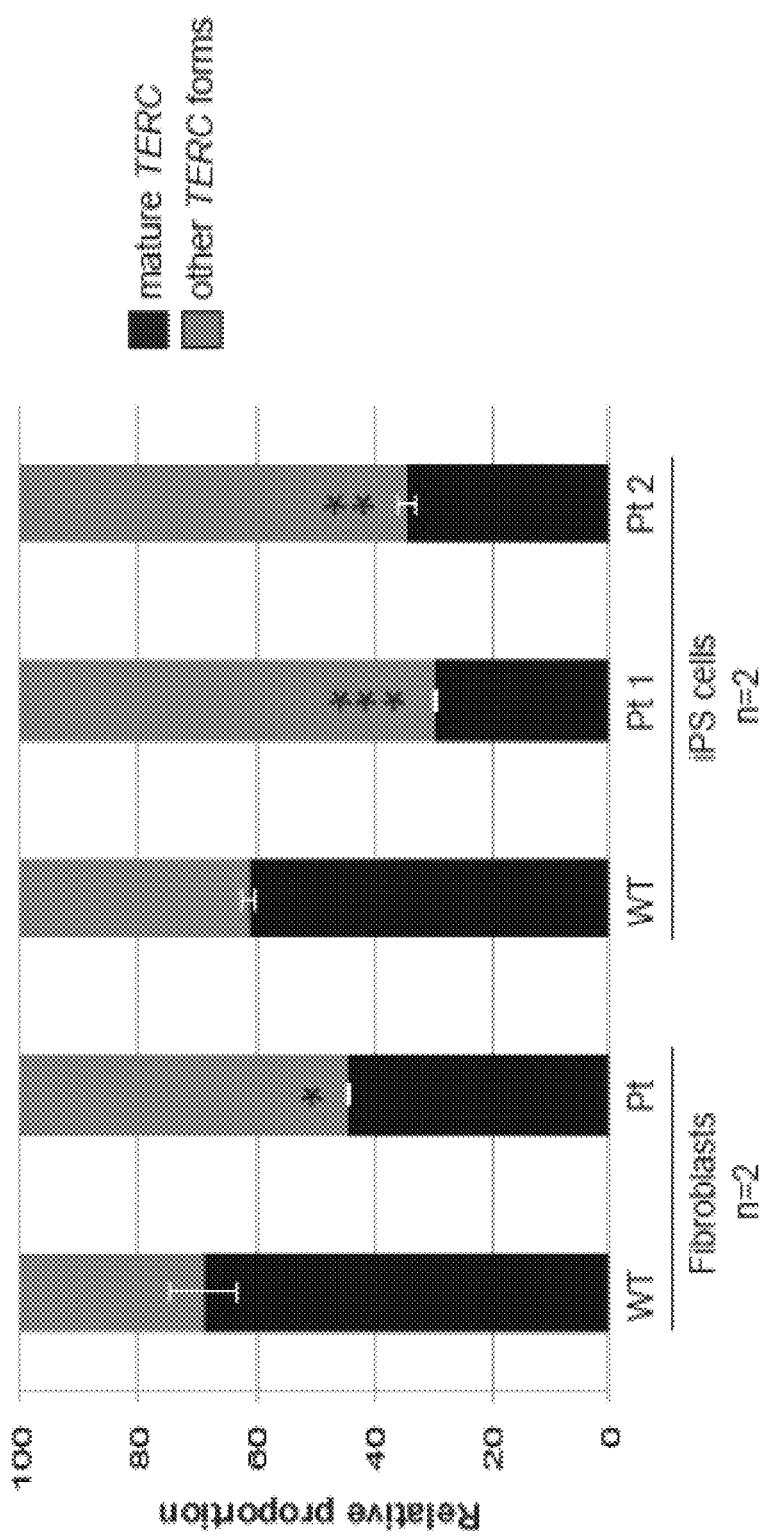
FIG. 7 is a bar graph showing categorized TERC reads from deep sequencing of 3' RACE products.

As further revealed in Table 7 TERC mRNA levels (TERC-defined threshold fold-change in RNA) in Wild Type (WT) versus patient derived cells (e.g., Patient for 2 indicate patient fibroblasts or iPS, with PARN alteration locus). The patient 1 and 2 noted in this below Table were identified via exon sequencing of PARN locus. The TERC data complements data derived from shRNA mediated knockdown of PARN in cell lines and demonstrates that PARN deficiency, both in vivo, from patients, and using cell lines that mimic such human condition as PARN deficiency, show diminished TERC levels compared to control groups (with no known PARN deficiency). Reference levels are determined from control groups. Upon further comparison across cell lines and as shown in FIG. 7, the percentages of mature TERC forms were significantly decreased in patient-derived cells (iPS or fibroblasts), thus altering the normal distribution of TERC. In FIG. 7, TERC forms other than mature TERC are increased in PARN-mutant patient cells. Of total trimmed reads, the proportion representing mature TERC is in black, and the proportion representing all extended forms of TERC, including genomically and non-genomically encoded bases, is in grey. Error bars represent standard deviation. Paired t-test calculations were performed between WT and patient cells for each cell type, with p values shown by asterisks (*≤0.05; ≤0.01; *≤0.001).

Example 5. Profiling Oligo(A) Forms of TERC Ends Demonstrate that PARN Deficiency Results in Increased TERC RNA Species with Abnormal (Extended) 3' Ends To investigate TERC maturation more closely, the 3' ends of TERC RNA were profiled in fibroblasts and iPS cells by deep sequencing (FIG. 4). A significant increase in the proportion of TERC species other than mature TERC in patient cells versus normal cells, including transcripts extended beyond the canonical 3' end (5' . . . ACAUGC-3' TERC canonical end), and a diverse range of non-genomically encoded additions (FIG. 4).

Figure 4A:
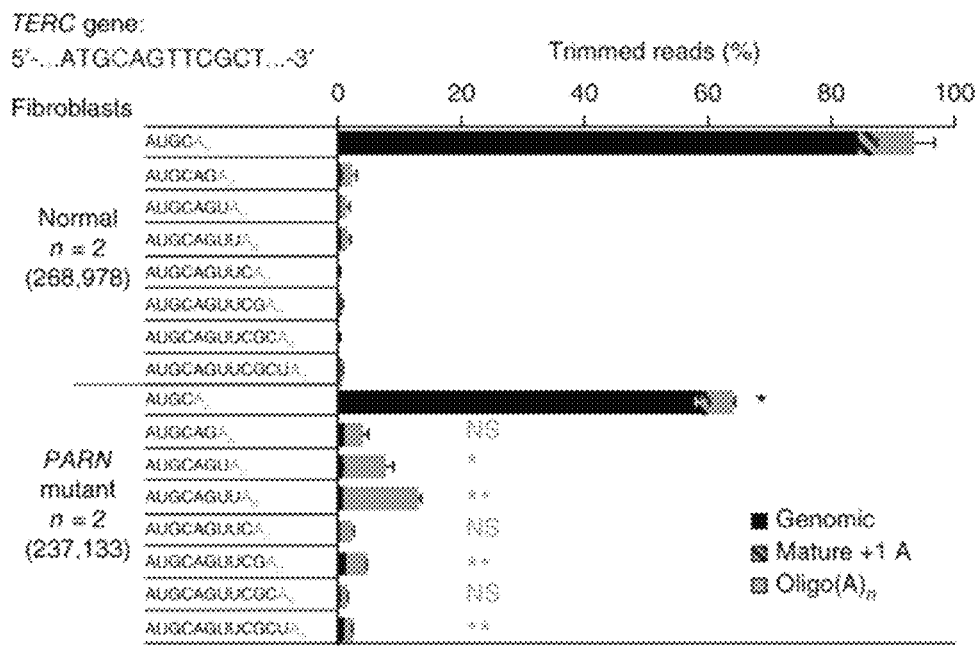
FIG. 4A is a bar graph showing TERC 3' end reads in fibroblasts. The sequenced products include AUGCAGUUCGCUA$_n$ (SEQ ID NO: 100), AUGCAGUUCGCA$_n$ (SEQ ID NO: 101), AUGCAGUUCGA$_n$ (SEQ ID NO: 102), AUGCAGUUCA$_n$ (SEQ ID NO: 103), AUGCAGUUA$_n$, AUGCAGUA$_n$, AUGCAGA$_n$, AUGCAA$_n$, and AUGCA$_n$. (A)$_n$ is oligo (A)$_n$.

The data above shows the distribution and frequency of two classes of TERC species: those containing up to eight genomically-encoded bases beyond the canonical TERC end, and the corresponding oligo(A) forms, which together comprised the majority of TERC forms across all samples. In patient fibroblasts, the percentage of mature TERC (i.e. ending at the canonical 5' . . . ACAUGC-3' sequence) was markedly reduced compared to normal fibroblasts (59% versus 84%; FIG. 4A). In FIG. 4A, 3' RACE PCR products from normal and PARN mutant patient fibroblasts were subjected to deep sequencing and aligned to the TERC gene.

Because the total amount of TERC in patient fibroblasts is ~45% of normal fibroblasts (FIG. 2), the level of mature TERC in patient fibroblasts is approximately one-third of that found in normal fibroblasts (27% versus 84%). At the same time, a significant increase in the proportion of oligo (A) forms of TERC were noted, including transcripts with genomically-encoded sequences beyond the mature TERC 3' end (FIG. 4A).

Figure 4B:
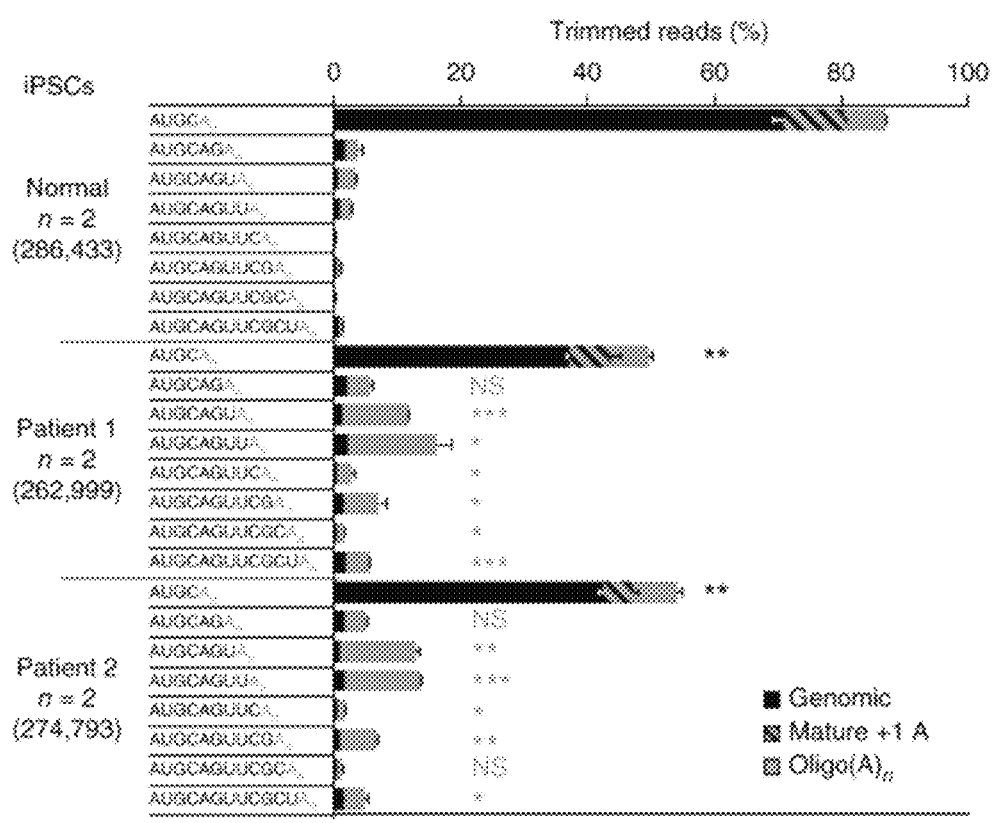
FIG. 4B is a bar graph showing TERC 3' end reads in iPS cells. The sequenced products include AUGCAGUUCGCUA$_n$ (SEQ ID NO: 100), AUGCAGUUCGCA$_n$ (SEQ ID NO: 101), AUGCAGUUCGA$_n$ (SEQ ID NO: 102), AUGCAGUUCA$_n$ (SEQ ID NO: 103), AUGCAGUUA$_n$, AUGCAGUA$_n$, AUGCAGA$_n$, AUGCAA$_n$, and AUGCA$_n$. (A)$_n$ is oligo (A)$_n$.

Haploinsufficiency due to deletion of one PARN allele in fibroblasts from patient 1's father yielded an intermediate phenotype. In iPS cells, mature TERC comprised ~70% of all species in normal cells but only ~40% in patient cells (FIG. 4B). In FIG. 4B, 3' RACE PCR products from normal and PARN mutant patient iPS cells were subjected to deep sequencing and aligned to the TERC gene.

Figure 8:
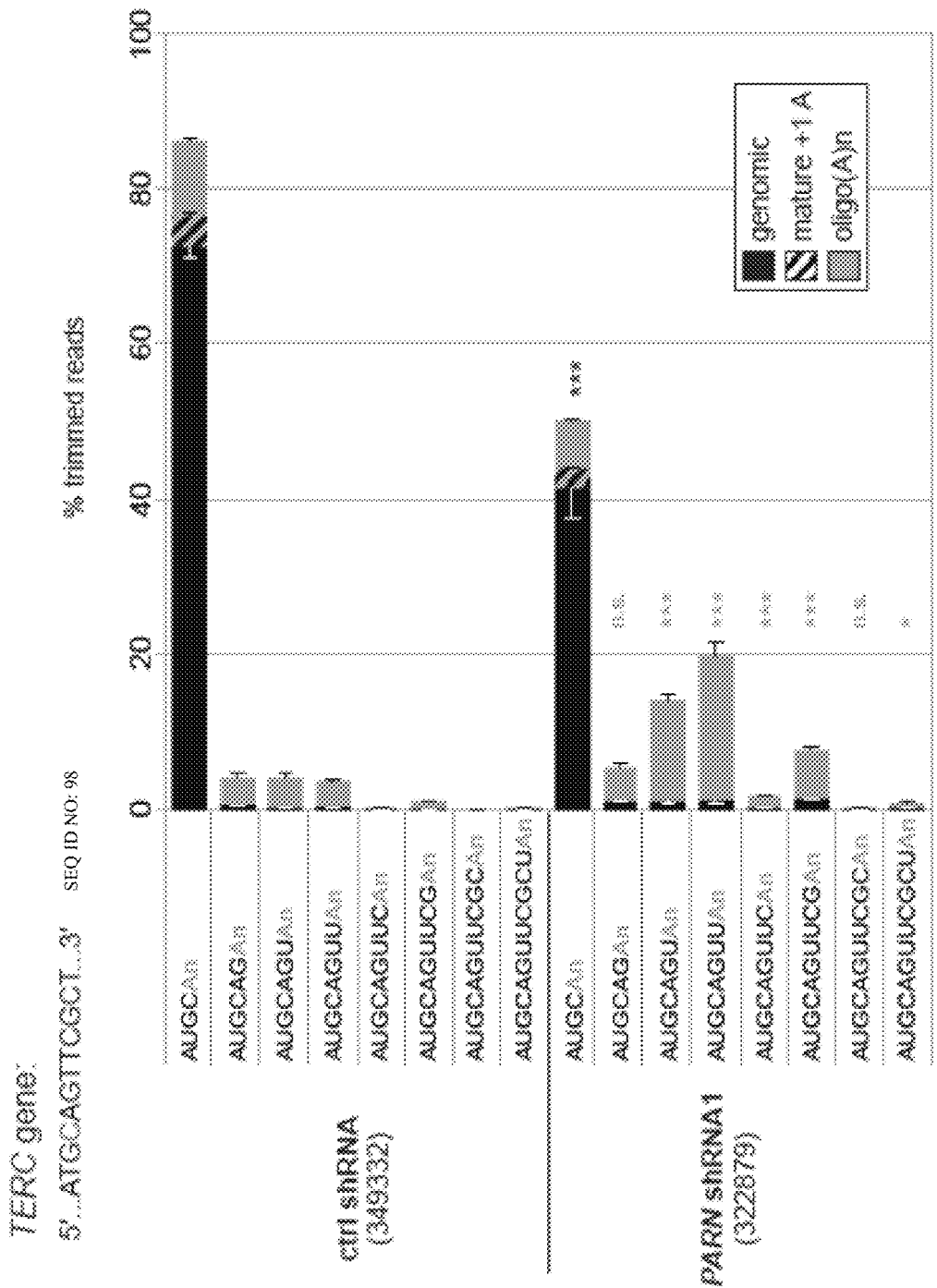
FIG. 8 is a graph showing PARN disruption in 293 cells results in increased 3'-extended and oligo-adenylated forms of TERC. The sequenced products include AUGCAGUUCGCUA$_n$ (SEQ ID NO: 100), AUGCAGUUCGCA$_n$ (SEQ ID NO: 101), AUGCAGUUCGA$_n$ (SEQ ID NO: 102), AUGCAGUUCA$_n$ (SEQ ID NO: 103), AUGCAGUUA$_n$, AUGCAGUA$_n$, AUGCAGA$_n$, AUGCAA$_n$, and AUGCA$_n$. (A)$_n$ is oligo (A)$_n$.

Again, significant increases in oligo(A) forms of TERC transcripts that extended beyond the mature 3' terminus were found, which in aggregate, comprised the majority of total TERC species in patient iPS cells (FIG. 3). Next, 293 cells were profiled in which PARN had been disrupted by RNA interference (using PARN specific shRNA constructs depicted in Table 6), and similarly diminished levels of mature TERC and increased oligo(A) forms (FIG. 8) in PARN deficient cells were found. In FIG. 8, total RNA prepared from 293 cells transduced with lentivirus-encoded shRNAs directed against PARN (shRNA1) versus control (ctrl) was subjected to 3' RACE and deep sequencing. The canonical TERC RNA terminus is indicated in red, in the context of the gene sequence. Genomically-encoded termini are in black, mature TERC with a single A (which may or may not be genomically-encoded) is hatched, and oligo(A) additions of any length (n) are solid blue. Profiles represent the averages from three independent experiments using two different TERC-specific primers. The total number of trimmed reads for each group is shown in parentheses. Error bars represent standard deviations and significance is indicated by p-values (*≤0.05; ≤0.01; *≤0.001; n.s. not significant).

Sanger sequencing of 3' RACE products corroborated the deep sequencing results. 3' RACE products from PARN-deficient versus control cells were PCR amplified, cloned and subjected to Sanger sequencing. Consistently across all profiling experiments in patient cells and PARN knockdown cells, it was observed a significant enrichment of oligo(A) forms of nascent TERC transcripts that were extended at +3, +4, and +6 bases beyond the canonical 3' end. Collectively, the analyses performed in the setting of PARN deficiency revealed intermediates in TERC biogenesis, and indicated a critical and non-redundant function for PARN in counteracting the oligo-adenylation of nascent TERC transcripts.

Figure 5A:
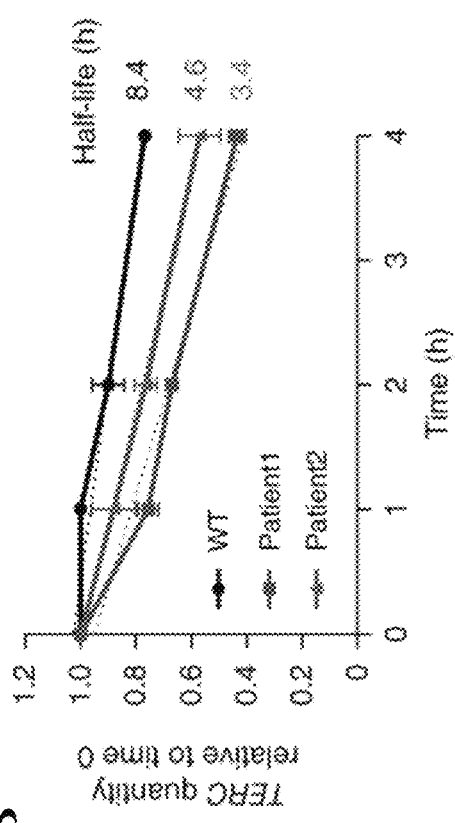
FIG. 5A is a photograph showing a representative Northern blot of TERC RNA levels in normal versus patient iPS cells, at 0, 1, 2 and 4 hours (h) following actinomycin treatment.
Figure 5B:
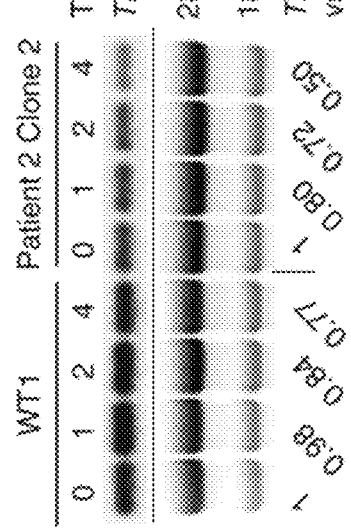
FIG. 5B is a graph showing TERC decay rate in normal and patient iPS cells.
Figure 5C:
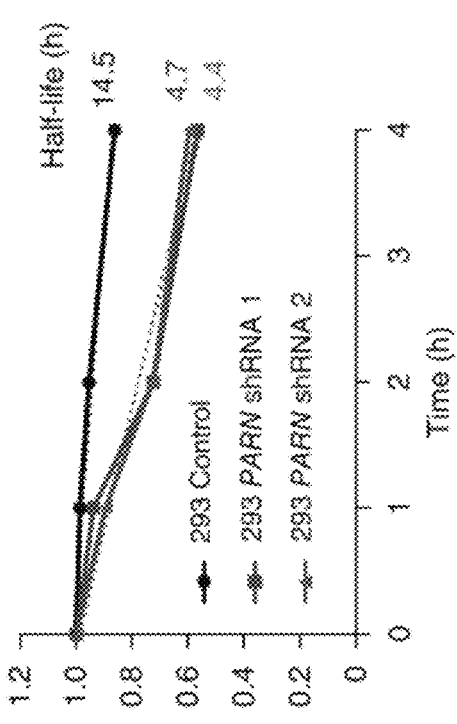
FIG. 5C is a photograph showing a Northern blot of TERC RNA in 293 cells subjected to shRNA-mediated knockdown of PARN (sh) versus control (ctrl).
Figure 5D:
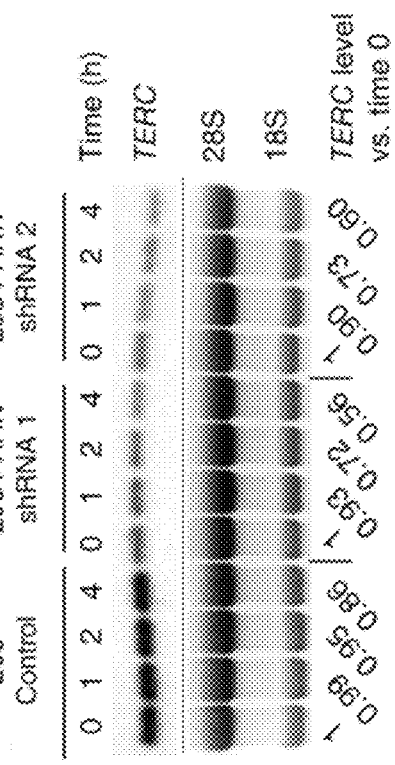
FIG. 5D is a graph showing decay rates of TERC RNA in 293 cells subjected to shRNA-mediated knockdown of PARN (sh) versus control (ctrl).

Example 6. PARN Knockdown Results in Decreased Half-Life and Destabilization of TERC RNA Oligo-adenylation is predicted to target nuclear RNA transcripts for degradation, and therefore the decay rate of TERC RNA was determined in PARN-deficient versus normal cells. The pol II transcription machinery of the cells was fully inhibited using Actinomycin and TERC RNA was quantified by a Northern blot. The data showed a decreased half-life of TERC transcripts in patient iPS cells compared to normal iPS cells, and also in PARN-knockdown 293 cells compared to control knockdown 293 cells (FIG. 5). In FIG. 5B, TERC decay rate is calculated from Northern blot analysis as shown in FIG. 5A. (n=2 for each group; error bar represent standard deviation). The dashed line reflects the slope determined by simple linear regression, and half-life is the calculated x-intercept at y=0.5. These results indicate that PARN deficiency results in destabilization of TERC RNA, and provide a mechanism for the observed decrease in steady-state TERC levels.

Example 7. Assessment of PARN Knockdown Specificity to TERC

PARN is widely expressed in a wide variety of cells. As such PARN's canonical role is believed to be in mRNA turnover. To isolate the effect of PARN deficiency as a specific manifestation at the level of telomere deficiency and TERC, RNA-Seq was performed to assess the global effects of PARN deficiency. Remarkably, no global change in no protein-coding mRNAs was manifested—(increase or decrease) that consistently exceeded the change in TERC levels in all 7 sample pairs (Table 3). These results suggest that the degree of PARN deficiency that is sufficient to disrupt TERC RNA transcript levels, 3' end processing, and stability and such deficiency in PARN does not result in changes of a similar magnitude in the levels of mRNAs expressed across cell types. This data confirms that the effect of PARN is highly specific to TERC and inhibiting it or deficiency of it does not affect global mRNA steady state levels.

Further gene transcript analysis (Table 4) using RNA from PARN deficient cells reveal specific genes that are alter in the setting of PARN deficiency revealing a gene expression profile that includes both increases and decreases in genes across seven types of pairwise comparisons. Interestingly, snoRNAs are highly modulated increased and decreased, revealing a regulatory pattern that distinguishes normal cell transcription from PARN deficient cells.

Figure 6E:
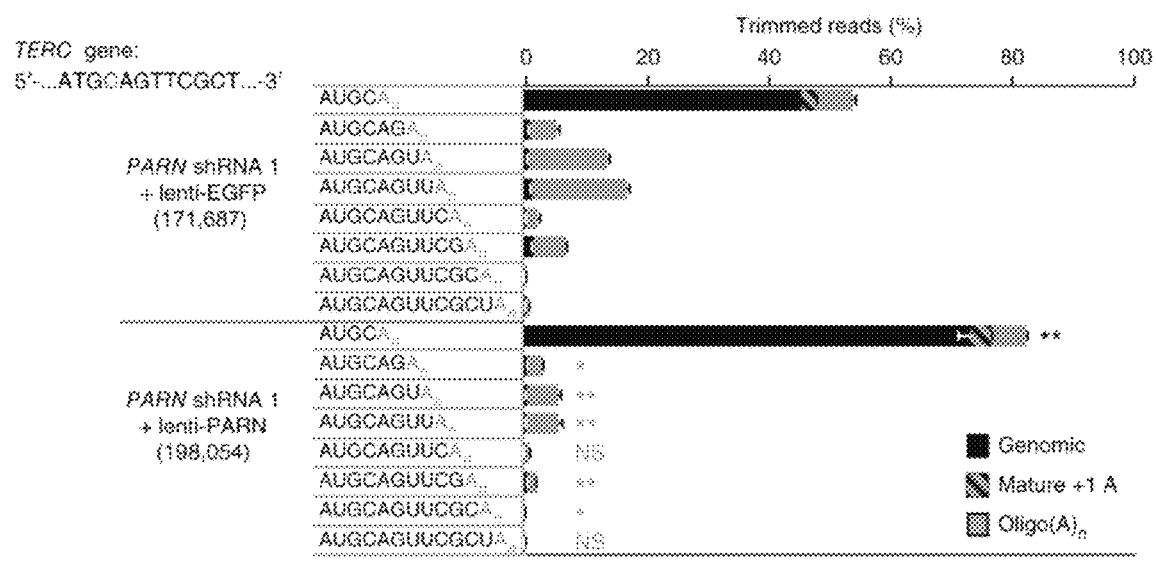
FIG. 6E is a graph showing data deep sequencing of 3' RACE PCR products from 293 cells in which PARN is disrupted by shRNA and rescued by lentivirus expressing PARN and EGFP. The sequenced products include AUGCAGUUCGCUA$_n$ (SEQ ID NO: 100), AUGCAGUUCGCA$_n$ (SEQ ID NO: 101), AUGCAGUUCGA$_n$ (SEQ ID NO: 102), AUGCAGUUCA$_n$ (SEQ ID NO: 103), AUGCAGUUA$_n$, AUGCAGUA$_n$, AUGCAGA$_n$, AUGCAA$_n$, and AUGCA$_n$. (A)$_n$ is oligo (A)$_n$.

Example 8. Overexpression of PARN Rescues TERC Steady State Levels and 3'-End Processing in Patient Cells The effects of ectopic PARN expression on TERC 3' end processing by using lentiviral vectors to overexpress PARN in 293 cells where PARN had been knocked-down using a hairpin (shRNA1) targeting the 3' untranslated region. The knockdown was highly specific for PARN compared to control cells expressing EGFP. Quantification of PARN is normalized to actin (n=3). The data shows a rescue of the diminished TERC steady-state levels (FIG. 6A), and also a restoration of TERC processing, as evidenced by an increased proportion of 3' RACE amplicons of the expected size relative to extended forms (FIG. 6B). Ethidium bromide staining of 18S rRNA is used as a loading control. Normalized TERC levels relative to control knockdown/EGFP-transduced 293 cells are shown. Similar results were obtained in patient fibroblasts (FIGS. 6C-6E). In FIG. 6C, normalized TERC levels are also indicated. Deep sequencing confirmed an increased proportion of mature TERC (72% versus 45%) and decreased oligo(A) forms after PARN rescue in 293 cells (FIG. 6E), and partial restoration of 3' end processing with ectopic PARN expression in patient fibroblasts. In FIG. 6E, statistical comparisons were between cells ectopically expressing PARN versus EGFP. Significance is indicated by p-values (*<0.05; <0.01; *<0.001; n.s. not significant; black for mature TERC, blue for extended, oligo(An) forms).

Figure 6F:
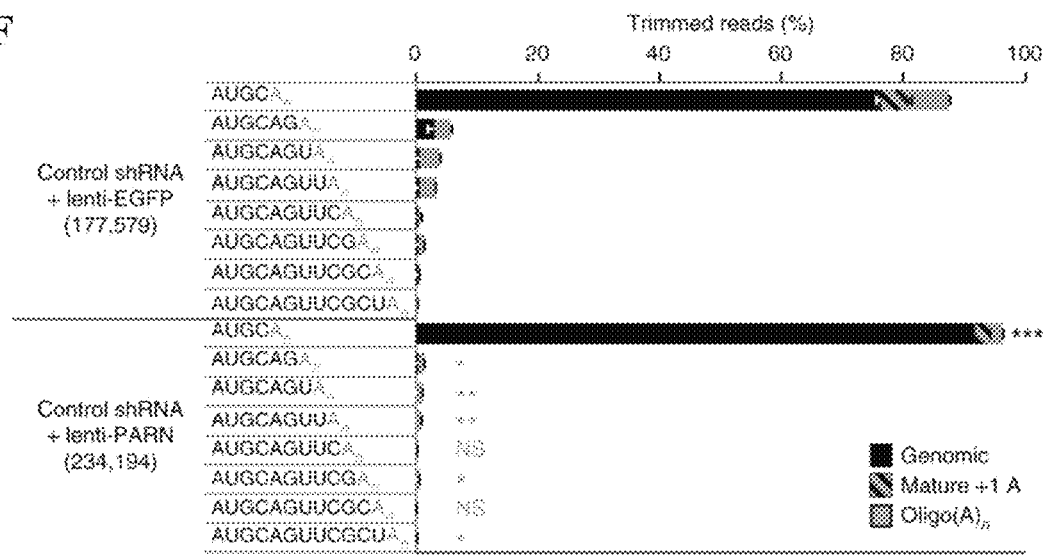
FIG. 6F is a graph showing data deep sequencing of 3' RACE PCR products from 293 control cells transduced with lentivirus overexpressing PARN or EGFP. The sequenced products include AUGCAGUUCGCUA$_n$ (SEQ ID NO: 100), AUGCAGUUCGCA$_n$ (SEQ ID NO: 101), AUGCAGUUCGA$_n$ (SEQ ID NO: 102), AUGCAGUUCA$_n$ (SEQ ID NO: 103), AUGCAGUUA$_n$, AUGCAGUA$_n$, AUGCAGA$_n$, AUGCAA$_n$, and AUGCA$_n$. (A)$_n$ is oligo (A)$_n$.

There were no increase levels of PARN protein in patient iPS cells using lentivirus vectors, possibly due to silencing or toxicity. Importantly, when PARN was overexpressed in control 293 cells, there was a significant increase in the proportion of mature TERC (92%, versus 75%) as well as a decrease in extended species and oligo(A) forms (FIG. 6F).

Furthermore, the effect of knockdown of PARN in iPS cells shown at the level of protein suggesting effective knockdown of protein activity for PARN. Taken together, these studies demonstrate that the defects in TERC biogenesis in patients with PARN mutations can be restored by ectopic expression of PARN and effect of shRNAs transduced into cells or 293 cell lines or primary cells derived from skin fibroblasts yield a highly specific reduction in both PARN mRNA and protein These data also reveal that PARN is limiting for TERC post-transcriptional processing, and thus can play a pivotal role in determining telomerase levels in cells. Equally, PARN activation using overexpression constructs (lentiviral constructs comprising PARN specific isolated cDNA) in iPS cells or fibroblasts or cell lines such as 293 reveal that augmenting PARN expression, rescues TERC levels and activity, e.g., TERC end processing. The data also demonstrate that TERC ends are highly relevant in cellular capacity to maintain telomere ends (mature ends), and that the cells that are deficient in PARN accumulate extended immature forms beyond the canonical C at the 3'end.

Example 9. PARN Deficiency in Human Patients Causes a Specific Impairment in the Processing of Nascent TERC, Resulting in Decreased TERC Levels, Impaired Telomerase Function and DC In two patients with classic DC, BMF and very short telomere length, biallelic defects in the PARN gene were identified. One patient carried a missense mutation c.19A>C encoding the substitution of a highly conserved amino acid, p.Asn7His, a variant that is not described in databases (Exome Variant Server and 1000 genomes), and which is predicted to be pathogenic by in silico (PolyPhen2) analysis (FIG. 5A). He appeared to be homozygous for the variant but SNP array analysis (not shown) and genomic qPCR indicate that he has inherited a large deletion encompassing the entire PARN gene from his father. Second patient carried a heterozygous missense mutation c.260C>T encoding the substitution of a highly conserved amino acid, p.Ser87Leu, from his healthy mother, also not described in variant databases, and which is predicted to be pathogenic at the amino acid level. He had no other potentially pathogenic exonic variants, nor does his healthy father. To find an explanation for this, the PARN mRNA was transcribed from the "wild-type" allele (without the exonic variant) and quantified. The PARN mRNA transcripts from that allele accumulated at only ~10% of the predicted amount in patient fibroblasts and iPS cells. These data and studies of the family demonstrate that this patient (patient 2) inherited a non-coding defect on the other PARN allele from his father that affects accumulation of its mRNA. Therefore, both patients have compound heterozygous mutations in PARN with defects in gene expression and missense mutations.

iPS cells were from the skin fibroblasts of these patients. It was noted that there were lower levels of PARN mRNA in both patients, commensurate with the deletion in patient 1, and in keeping with defective transcription from one allele in patient 2. Importantly, both patients show low TERC levels (FIG. 6). These findings are recapitulated by shRNA in 293 cells, wherein disrupting PARN results in significant reductions in TERC level. Importantly, decreases in DKC1 transcripts were not observed, nor in other telomere biology associated genes including TERF1 and RTEL1 (not shown). These data indicate defects in TERC levels in the setting of PARN deficiency that are independent of reductions in other telomere biology genes, most importantly DKC1.

The Examples set forth above provide a basis of a therapeutic strategy whereby a skilled practitioner can manipulate any number of genes that are modulated in cells, including TRF4-2, PARN or TERC RNA and would be in a position to interrogate cells with compounds known in the art; contact cells with compound to detect oligo(A) form of TERC, compare the proportion of this oligo(A) forms of TERC to total cellular TERC RNA in the provided cell; and further restore mature TERC levels to steady state levels, to thereby promote or restore the cell's ability to self-renew or regenerate and more specifically, restore levels or activity of TERC or other non-coding RNA, also by contributing to post-transcriptional processing.

This possibility is validated by data shown above and throughout the application that the mature forms of TERC in PARN deficient cells is at least or about 4-fold higher than that in normal cells (47% versus 12%). What can also be estimated is the exact proportion of the extended or oligo(A) form of TERC is present in an iPS cell compared to fibroblasts (45% versus 17%). Remarkably, these studies indicate that the vast majority of total cellular TERC in PARN mutant patient iPS cells is of the oligo(A) form. This strategy overall comprises methods to identify compounds that mitigate the effect of the decreased steady-state TERC levels and deficits in telomerase function by measurement of total TERC levels and different forms of TERC, and to optionally, treat telomere or other diseases.

Example 10. Post-Transcriptional Manipulation of TERC Reverses Molecular Hallmarks of Telomere Disease Poly(A) specific ribonuclease (PARN) is required for post-transcriptional maturation of the telomerase RNA component, TERC. PARN mutations result in the accumulation of 3' oligo-adenylated forms of nascent TERC RNA transcripts, which are targeted for destruction, thus causing telomerase deficiency and telomere diseases. It is hypothesized that inhibiting post-transcriptional oligo-adenylation of TERC would counteract the effects of PARN deficiency and restore telomere homeostasis. Here, it is shown that disruption of the non-canonical poly(A) polymerase PAPD5 restores TERC levels, telomerase activity and telomere elongation in PARN-mutant patient cells. Overexpression of TERC RNA resulted in telomere elongation in PARN-mutant patient cells. The noncanonical poly(A) polymerase PAPD5 oligo-adenylates nuclear RNAs including TERC post-transcriptionally. It shows that disruption of PAPD5 increased TERC stability and steady state levels in PARN-mutant patient cells. Furthermore, in patient induced pluripotent stem cells, PAPD5 knockdown increased telomerase activity and restored telomere length, without a pronounced impact on the transcriptome or cellular viability. The results indicate that TERC levels depend on the balance of PARN and PAPD5 in human stem cells, which in turn are key regulators of telomerase activity and telomere maintenance. PAPD5 is identified as a component of the post-transcriptional machinery potentially amenable to pharmacological inhibition, to restore telomere maintenance in patients with DC and IPF caused by PARN mutations. The results demonstrate that manipulation of post-transcriptional regulatory pathways can reverse molecular hallmarks of telomere disease.

Methods

Primary Cells and Cell Lines Fibroblast cultures and iPSCs were generated from NHSF2 and PARN-mutant skin fibroblasts as described, e.g., in Agarwal, Suneet, et al. "Telomere elongation in induced pluripotent stem cells from dyskeratosis congenita patients." Nature 464.7286 (2010): 292-296.; Moon, Diane H., et al. "Poly (A)-specific ribonuclease (PARN) mediates 3 [prime]-end maturation of the telomerase RNA component." Nature genetics 47.12 (2015): 1482-1488. PARN-mutant patient fibroblasts were immortalized by transduction with pBABE-hTERT-puro retroviral vectors. iPSCs were maintained in E8 medium (Life Technologies, Carlsbad, Calif.) on hES-qualified Matrigel matrix (BD Biosciences, San Jose, Calif.). HEK 293 were subcultured and expanded using trypsin 0.05% and DMEM 10% FCS.

RNA Interference and cDNA Expression short-hairpin RNA (shRNA) constructs. Duplex oligonucleotides encoding shRNA targeting human PAPD5 (ENA accession: FR872509) or luciferase control (Table 13) were cloned into the pLKO.1-puro vector and pLKO.1-blast vectors (Addgene #10878 and #26655). shRNA constructs targeting human PARN (NM_002582) were as described, e.g., in Moon, Diane H., et al. "Poly (A)-specific ribonuclease (PARN) mediates 3 [prime]-end maturation of the telomerase RNA component." Nature genetics 47.12 (2015): 1482-1488.

cDNA expression constructs. Codon-optimized cDNA encoding the PAPD5 open reading frame (ENA accession: FR872509) with an N-terminal FLAG tag was synthesized (Integrated DNA Technologies), and cloned into pLX304 (blasticidin; Addgene #25890). Lentiviral vectors encoding EGFP and PARN were cloned into pLX301 (puromycin; Addgene #25895) and pLX304. Retroviral and lentiviral vectors pBABE-hTERT-puro (Addgene #1171), p-MIG-DKC1 and pHIV7/SF-U3-TER-500 and controls were described in e.g., Agarwal, Suneet, et al. "Telomere elongation in induced pluripotent stem cells from dyskeratosis congenita patients." Nature 464.7286 (2010): 292-296.

Viral vector production and transduction. Retroviral particles were produced by co-transfection of HEK 293T cells with retroviral vectors, VSV-G and Gag-Pol packaging plasmids as described in e.g., Agarwal, Suneet, et al. "Telomere elongation in induced pluripotent stem cells from dyskeratosis congenita patients." Nature 464.7286 (2010): 292-296. Lentiviral particles were produced by co-transfection of HEK 293T cells with lentiviral vectors, pCMV_dR8.91 and pCMV_VSV-G. For knockdown and overexpression experiments, HEK 293 cells, fibroblasts and iPSCs were transduced with viral vectors in the presence of protamine sulfate (10 µg/ml) for 8-12 hours. For TERC and DKC1 experiments, transduced HEK 293 cells and fibroblasts were sorted for mCherry or EGFP expression and cultured without further selection. For antibiotic selection in shRNA and other overexpression experiments, HEK 293 cells and fibroblasts were cultured in puromycin (1-2 µg/ml) and/or blasticidin (5-10 µg/ml), and iPSCs were cultured in puromycin (0.2 µg/ml) and/or blasticidin (3-5 µg/ml).

RNA Isolation, cDNA Synthesis and Quantitative RT-PCR

RNA was isolated using TRIzol (Ambion). After DNase treatment (Turbo DNA-free, Ambion), cDNA was synthesized using SuperScript III Reverse Transcriptase (Invitrogen, Carlsbad, Calif.). qPCR was performed using SsoAdvanced Supermix (Bio-Rad, Hercules, Calif.) and primers PAPD5_L/R and POLR2A_L/R (Table 13) in a CFX96 Real-Time PCR detection system (Bio-Rad, Hercules, Calif.). Quantification of PAPD5 was normalized to POLR2A. Graphing and statistical analysis was performed using GraphPad Prism.

Western Blot Analysis

Cell lysates were subjected to SDS-PAGE and transferred to PVDF membranes using standard procedures. Proteins were detected using antibodies in Table 14 and Clarity Western ECL reagent (Biorad, Hercules, Calif.). Quantification was performed using the ChemiDoc Touch imaging system (Biorad, Hercules, Calif.).

Northern Blots

Formaldehyde/agarose gel electrophoresis. Total RNA was separated on 1.5% agarose/formaldehyde gels, transferred to Hybond N+ membranes (Amersham), and hybridized with $\alpha$-$^{32}$P-dCTP-labeled TERC probe (TERC_L2/TERC_R (Table 13)) in ULTRAhyb (Life Technologies, Carlsbad, Calif.). Signals were normalized to 18S rRNA by ethidium bromide staining. Quantification was performed using ImageJ.

TERC RNA Decay $10^6$ iPSCs were treated with 5 µg/ml of actinomycin D (Life Technologies, Carlsbad, Calif.) and harvested in TRIzol. Purified RNA was subjected to Northern blot. TERC signals were normalized to 18S rRNA. Decay slopes were determined by simple linear regression and transcript half-life was calculated as the x-intercept at y=0.5, using GraphPad Prism.

3' Rapid Amplification of cDNA Ends (RACE)

3' RACE was performed as described (Moon, Diane H., et al. "Poly (A)-specific ribonuclease (PARN) mediates 3 [prime]-end maturation of the telomerase RNA component." Nature genetics 47.12 (2015): 1482-1488). Total RNA was ligated to 5'-adenylated, 3'-blocked adapter (New England Biolabs, Ipswich, Mass.) with T4 RNA ligase KQ (New England Biolabs, Ipswich, Mass.). cDNA was synthesized using universal RT primer and SuperScript III. PCR amplification was carried out using TERC_L/universal RT primers (Table 13) with SsoAdvanced Supermix (Bio-Rad, Hercules, Calif.). PCR products were run on 3% agarose gels.

RNA Profiling and Transcriptome Analysis by Next Generation Sequencing

3' End Sequencing of TERC RNA

TERC RNA 3' ends were profiled as described in e.g., Moon, Diane H., et al. "Poly (A)-specific ribonuclease (PARN) mediates 3 [prime]-end maturation of the telomerase RNA component." Nature genetics 47.12 (2015): 1482-1488. Briefly, RACE products were ligated and amplified using barcoded Illumina adapters, and sequenced on an Illumina MiSeq platform. Reads mapping to the TERC gene were analyzed using custom developed Perl scripts.

RNA-Seq

Transcriptome analysis of the alterations in coding and non-coding RNAs from pairs of PAPD5 versus luciferase control knockdown cell lines (HEK 293, WT iPSC, Patient 1 clone 1 and clone 2 iPSCs) was performed using methods described in e.g., Moon, Diane H., et al. "Poly (A)-specific ribonuclease (PARN) mediates 3 [prime]-end maturation of the telomerase RNA component." Nature genetics 47.12 (2015): 1482-1488. Briefly, total RNA was processed using the Total RNA with RiboZero Gold kit, and barcoded libraries were pooled and sequenced on two lanes of HiSeq 2500 High Output single read 50 bases format.

Mapping and analysis were performed to find genes that were commonly differentially expressed after PAPD5 knockdown. The fold-change was used in TERC in HEK 293 and Patient 1 clone 1 and clone 2 iPSCs as a threshold to define genes as differentially expressed in a paired comparison manner. The TERC-defined thresholds (ln(1+TPM)), were: HEK 293 (0.25); Patient 1 clone 1 iPSC (0.67); Patient 1 clone 2 iPSC (1.24). Individual transcripts altered by PAPD5 knockdown to a degree exceeding this fold change were compared to define those that were commonly altered in all 3 cell types or in 2 of 3 comparisons (Table 11-12). The next question is whether the number of commonly altered genes in each category of transcript was different than what would be expected by chance using the Chi-squared test (Table 10).

Telomerase Activity and Telomere Length

Telomere repeat amplification protocol (TRAP) and terminal restriction fragment (TRF) length analysis were performed as described in e.g., Moon, Diane H., et al. "Poly (A)-specific ribonuclease (PARN) mediates 3 [prime]-end maturation of the telomerase RNA component." Nature genetics 47.12 (2015): 1482-1488.

Results

TERC is Limiting for Telomere Maintenance in PARN Deficient Cells

Figure 10A:
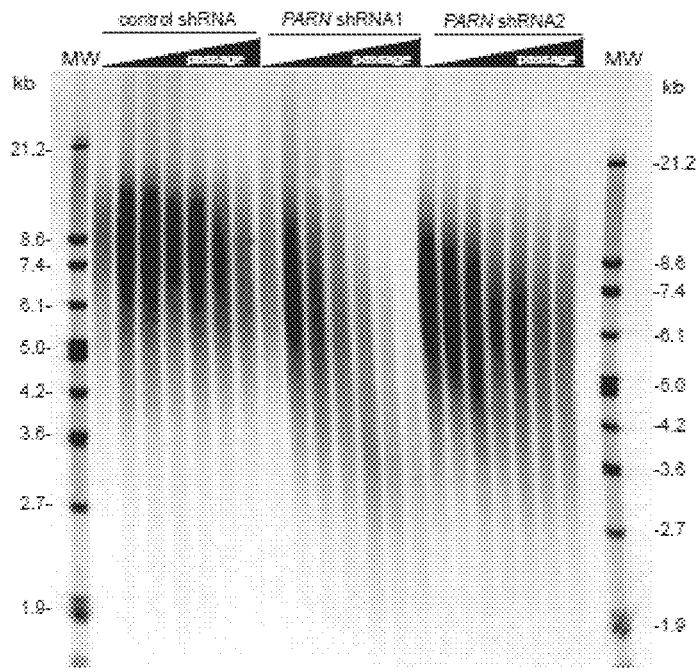
FIG. 10A is a photograph of Southern blot showing telomere restriction fragment (TRF) length analysis in HEK293 cells infected with lentivirus encoding shRNAs targeting luciferase (control) versus PARN.
Figure 10A:
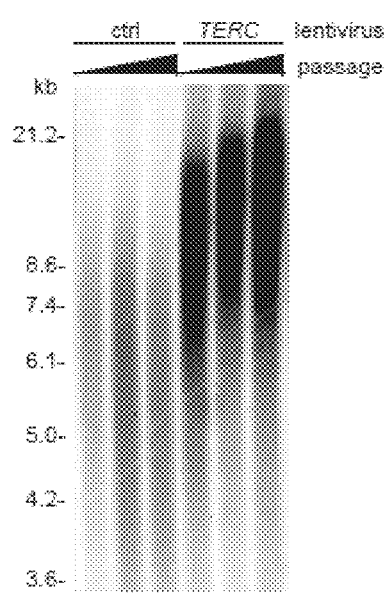
Figure 10A:
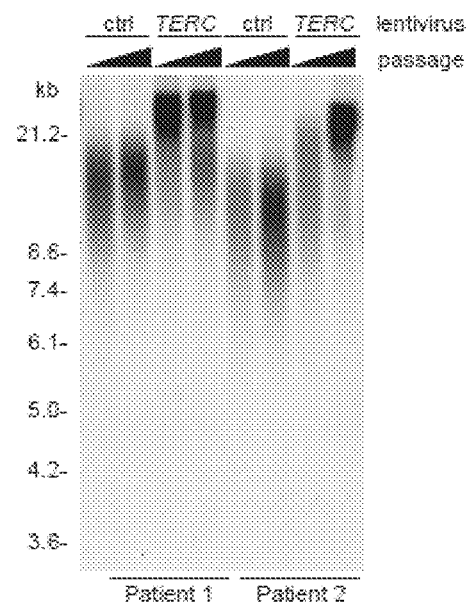
Figure 13:
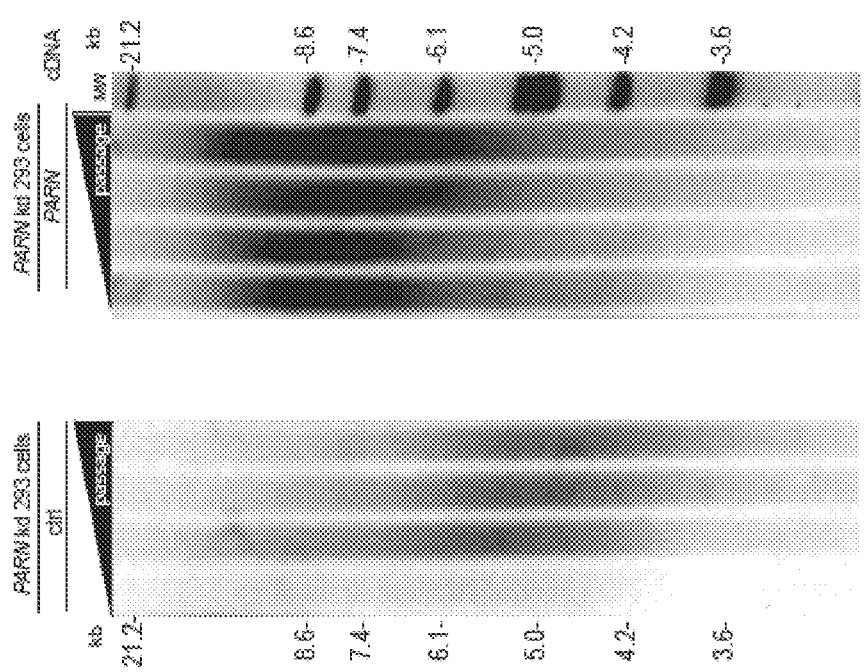
FIG. 13 is a graph showing telomere length in PARN kd 293 cells after PARN overexpression.
Figure 14:
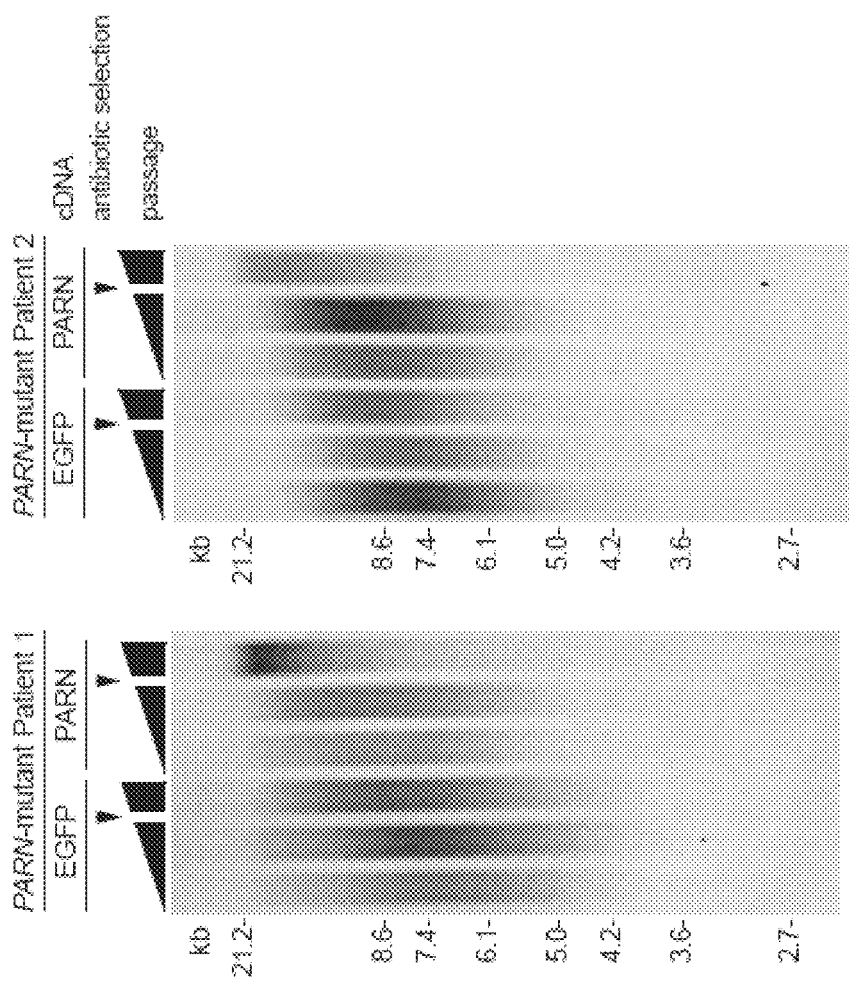
FIG. 14 is a graph showing telomere elongation in immortalized PARN-mutant fibroblasts after PARN rescue.

To directly assess the effects of PARN deficiency on telomere maintenance, PARN was disrupted in HEK 293 cells using lentivirus-encoded short-hairpin RNAs (shRNAs), and continuously cultured the transduced cells under antibiotic selection. In PARN knockdown cells, using two independent shRNAs, it was observed telomere attrition over time as compared to control cell lines (FIG. 10A). When a PARN cDNA was overexpressed, which is not susceptible to knockdown by one of the shRNAs that targets the 3' untranslated region, it was observed telomere length increased as compared to control cells (FIG. 13). In FIG. 13, southern blot of telomere length by telomere restriction fragment length analysis in PARN kd 293 cells. Cell were transduced with lentivirus containing vector alone (ctrl) or encoding PARN. Telomere length was followed for 12 passages. (~6 weeks). Next, the effects of restoring PARN expression on telomere maintenance in patient cells was evaluated. In TERT-immortalized fibroblasts from patients with DC caused by PARN loss-of-function mutations, PARN expression restored telomere elongation. These results confirm that PARN deficiency compromises telomere maintenance, and indicate that PARN is limiting for telomere maintenance in human cells, despite the presence of TERT (FIG. 14). In FIG. 14, Southern blot of telomere length by telomere restriction fragment length analysis in TERT-immortalized, PARN-mutant patient fibroblasts. Cells were transduced with lentivirus encoding either EGFP or PARN and also carrying a blasticidin resistance cassette. Blasticidin selection was performed at the time point indicated by the arrowhead.

To determine whether PARN deficiency affects telomere elongation primarily via effects on TERC, TERC was stably overexpressed via lentiviral vectors in PARN deficient cells and analyzed telomere length over time. Expression of TERC in PARN-knockdown HEK 293 cells led to rapid elongation of telomeres (FIG. 10B). Similarly, expression of TERC in TERT-immortalized fibroblasts from patients with PARN mutations led to elongation of telomeres (FIG. 10C).

To determine whether dyskerin deficiency plays a role in PARN-mutant cells, a DKCJ cDNA was ectopically expressed in PARN-knockdown HEK 293 cells, but did not observe a restoration of telomere length. These data demonstrate that PARN deficiency impairs telomere maintenance via a direct impact on TERC RNA, and suggest that enhancing TERC will restore telomere elongation in PARN-mutant cells.

Figure 15A:
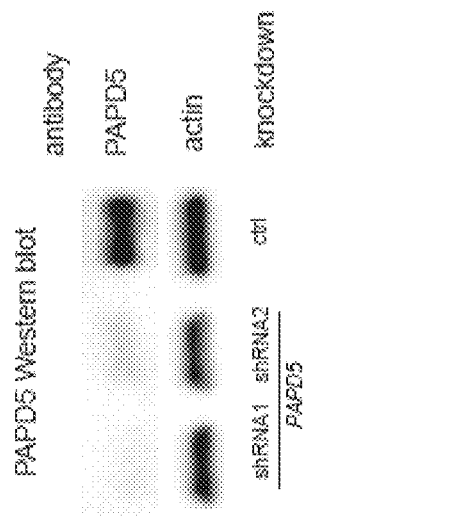
FIG. 15A is a bar graph showing quantitative PCR (qPCR) of PAPD5 transcripts from HEK 293 cells transduced with lentiviruses expressing shRNAs against luciferase (ctrl) versus PAPD5.
Figure 15B:
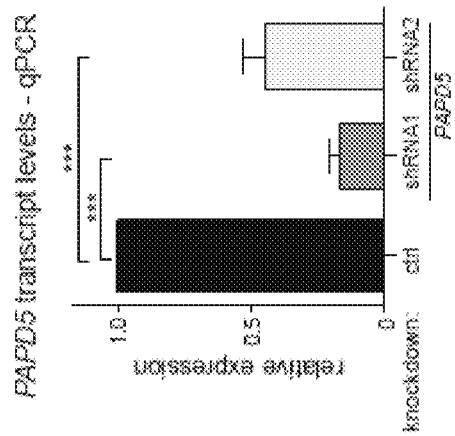
FIG. 15B is a photograph of immunoblot of PAPD5 and actin protein levels in HEK293 cells transduced with lentivirus encoding shRNA against luciferase (ctrl) or PAPD5.

PAPD5 Negatively Regulates TERC Via Oligo-Adenylation and Opposes PARN-Mediated Maturation of TERC It is hypothesized that if the primary role of PARN in telomere biology is to counteract oligo-adenylation and degradation of TERC, then PAPD5 inhibition should be sufficient restore TERC processing and increase telomerase activity in human cells. To investigate this, a comprehensive analysis of the effects of PAPD5 loss-of-function and gain-of-function on TERC was performed. PAPD5 in HEK 293 cells was disrupted using lentivirus-encoded shRNAs and performed rapid amplification of complementary DNA ends (RACE) to characterize TERC 3' ends (FIG. 11A; FIG. 15). In FIG. 15A, quantitative PCR (qPCR) of PAPD5 transcripts from HEK 293 cells transduced with lentiviruses expressing shRNAs against luciferase (ctrl) versus PAPD5. n=3 biological replicates. Error bar indicates standard deviation, and significance is indicated by P value≤0.001 (***).

With PAPD5 knockdown, there was an alteration in the size distribution of TERC 3' ends, in that the intensity of the amplicon corresponding to the mature form of TERC was increased relative to the immature, extended form of TERC that predominates in PARN knockdown cells (FIG. 11B). In FIG. 11B, immunoblot of PAPD5 and actin protein levels in HEK293 cells transduced with lentivirus encoding shRNA against luciferase (ctrl) or PAPD5. The expected amplicon representing mature TERC and the extended forms are indicated (arrows) (n=4). 3' ends of TERC RNA was profiled by deep sequencing with and without PAPD5 knockdown. PAPD5 inhibition significantly reduced the proportion of genomically extended TERC species that were oligo-adenylated, as well as the average oligo(A) tail length of nascent TERC transcripts (FIGS. 11C-11D). In FIG. 11C, the canonical TERC 3' terminus is shown in red. The relative proportions of mature TERC and TERC RNA species extending up to 8 bases into the genomic sequence, with or without post-transcriptionally added oligo(A) tails, are depicted. Genomically-encoded termini are in black, mature TERC with a single A (which may or may not be genomically-encoded) is hatched, and oligo(A) additions of any length (n) are in solid blue. Total trimmed reads in parentheses. n=2 biological replicates. Error bars=standard deviation. For statistical evaluations, mature TERC forms and oligo(An) ends for all genomically extended TERC species were compared between control and PAPD5 knockdown cells in a two-tailed t-test. P values: *≤0.05; ≤0.01; *≤0.001; n.s. not significant; blue for extended, oligo(An) forms.

Figure 11E:
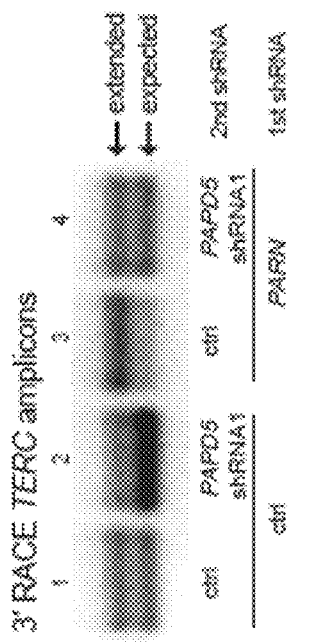
FIG. 11E is a photograph of Northern blot of TERC from HEK293 cells transduced with lentivirus encoding shRNA against PAPD5 versus luciferase, followed by transfection with plasmids expressing PAPD5 versus EGFP cDNAs.
Figure 16:
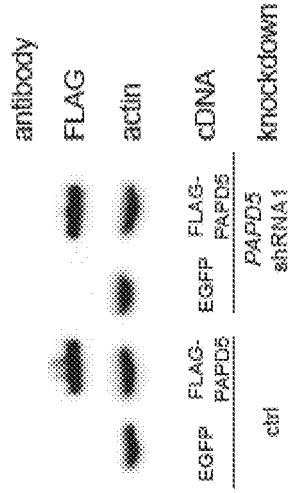
FIG. 16 is a photograph of Western blots showing overexpression of PAPD5 in control and PAPD5 knockdown cells.

Conversely, both the percentage of mature TERC (FIGS. 11C-11D) and steady-state levels of TERC transcripts were increased in PAPD5 knockdown cells (FIG. 11E; lanes 1 and 3). When PAPD5 cDNA was overexpressed in cells (FIG. 16), total TERC RNA transcript levels were decreased to approximately one-third of those found in control cells within 48 hours (FIG. 11E; lanes 1 and 2). In PAPD5 knockdown cells, expression of PAPD5 cDNA (which is codon-optimized and insensitive to PAPD5 shRNAs) also reduced TERC levels to less than those found in control cells (FIG. 11E; lanes 3 and 4). In FIG. 11E, ethidium bromide staining of 18S rRNA is used as a loading control. TERC levels are normalized to those in cells with control knockdown and EGFP expression. n=3 biological replicates. These data confirm that PAPD5 negatively regulates TERC via oligo-adenylation of nascent RNA transcripts. In FIG. 16, Western blots of cell lysates from control knockdown versus PAPD5 knockdown HEK 293 cells, with lentiviral overexpression of either a cDNA encoding FLAG-tagged, codon-optimized PAPD5 or EGFP. Actin is shown as a loading control. Cells are those used in FIG. 11E.

Figure 11F:
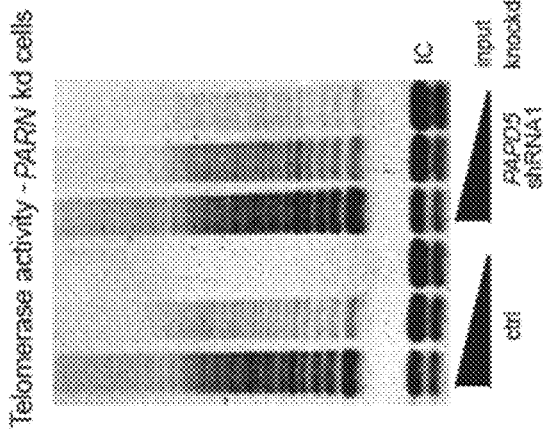
FIG. 11F is a graph showing 3' RACE TERC amplicons from HEK 293 cells stably transduced with lentivirus encoding shRNA directed against PARN versus luciferase, followed by transduction with lentivirus encoding shRNA directed against PAPD5 or luciferase.

To establish the relationship between PAPD5 and PARN in post-transcriptional regulation of TERC, PAPD5 was disrupted in the setting of PARN deficiency. By 3' RACE, PARN knockdown results in an accumulation of extended TERC forms (FIG. 11F, lane 3 versus lane 1). PAPD5 inhibition in PARN deficient cells restored the distribution of TERC 3' ends to that observed in control cells (FIG. 11F; compare lanes 4 and 1). Double antibiotic selection was employed. n=3 biological replicates.

Figure 17B:
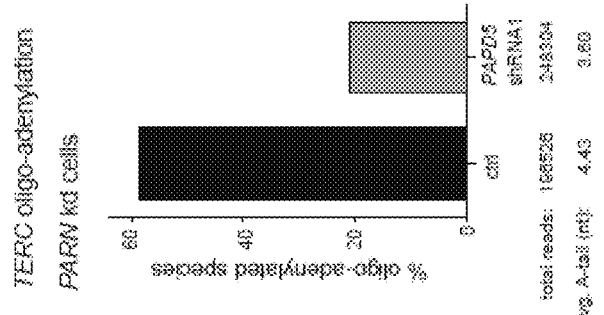
FIG. 17B is a bar graph showing oligo(An) species as a proportion of total reads are indicated in control versus PAPD5 knockdown, PARN-deficient HEK293 cells.
Figure 17A:
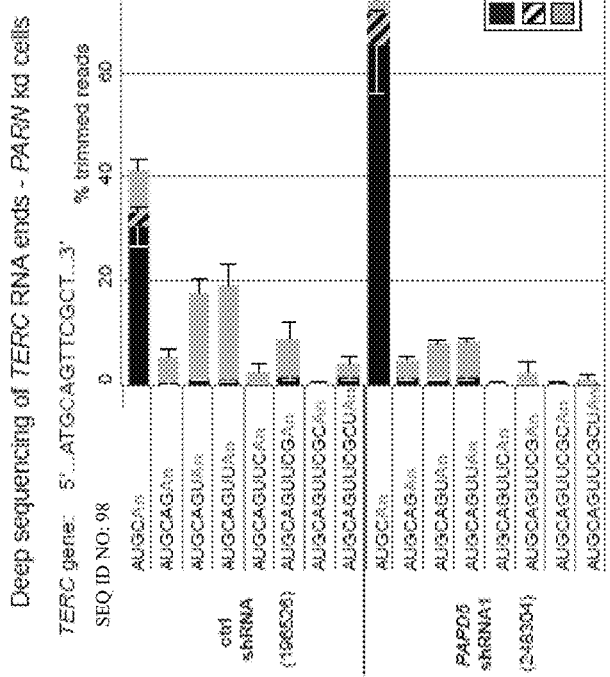
FIG. 17A is a graph showing 3' RACE PCR products from PARN knockdown HEK 293 cells transduced with lentivirus encoding shRNA against PAPD5 versus control were subjected to deep sequencing, as in FIG. 11C. The sequenced products include AUGCAGUUCGCUA$_n$ (SEQ ID NO: 100), AUGCAGUUCGCA$_n$ (SEQ ID NO: 101), AUGCAGUUCGA$_n$ (SEQ ID NO: 102), AUGCAGUUCA$_n$ (SEQ ID NO: 103), AUGCAGUUA$_n$, AUGCAGUA$_n$, AUGCAGA$_n$, AUGCAA$_n$, and AUGCA$_n$. (A)$_n$ is oligo (A)$_n$.

By deep sequencing of 3' RACE products, it was noted that the proportion of mature TERC was significantly increased after PAPD5 knockdown in PARN deficient cells (65% versus 32%, P≤0.05). Moreover, the increased proportion (~60%) of oligo(A) TERC species found in PARN deficient cells was decreased by 3-fold after inhibiting PAPD5, and the average length of oligo(A) tails was also reduced (FIG. 17). In FIG. 17A, 3' RACE PCR products from PARN knockdown HEK 293 cells transduced with lentivirus encoding shRNA against PAPD5 versus control were subjected to deep sequencing. Proportions are averaged from 2 biological replicates for each group. Error bars represent standard deviations. For statistical evaluations, mature TERC forms and oligo(An) ends for all genomically-extended TERC species were compared between control and PAPD5 knockdown cells in a two-tailed t-test. Significance for difference in proportion of mature TERC is indicated by P value≤0.05 (*). In FIG. 17B, oligo(An) species as a proportion of total reads are indicated in control versus PAPD5 knockdown, PARN-deficient HEK293 cells. The A-tail length in nucleotides (nt) was averaged (avg) over the entire population of oligo(An) species for each condition and is indicated.

Figure 11G:
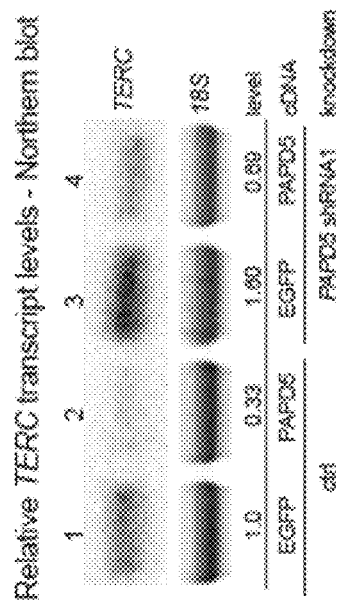
FIG. 11G is a photograph of Northern blot of TERC RNA from cells stably transduced with lentivirus encoding shRNA directed against PARN versus luciferase, followed by transduction with lentivirus encoding shRNA directed against PAPD5 versus luciferase.
Figure 18:
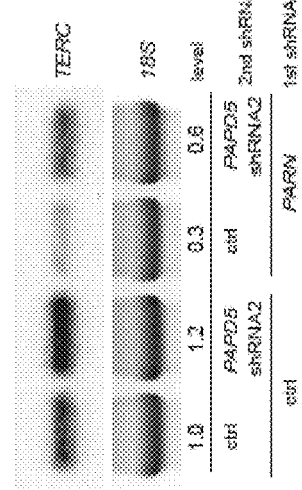
FIG. 18 is a photograph of Northern blot showing relative TERC transcript levels in control and PARN-deficient cells with PAPD5 knockdown.

By Northern blot, it was noted that steady state levels of TERC transcripts were increased by PAPD5 inhibition in both normal and PARN deficient cells (FIG. 11G; FIG. 18). In FIG. 18, Northern blot of RNA from control versus PARN-deficient HEK 293 cells, with lentiviral knockdown using either control (ctrl) shRNA or shRNA targeting PAPD5. Ethidium bromide staining of 18S rRNA is shown as a control for loading. Results using PAPD5 shRNA2 shown here are consistent with the results using PAPD5 shRNA1.

Figure 11H:
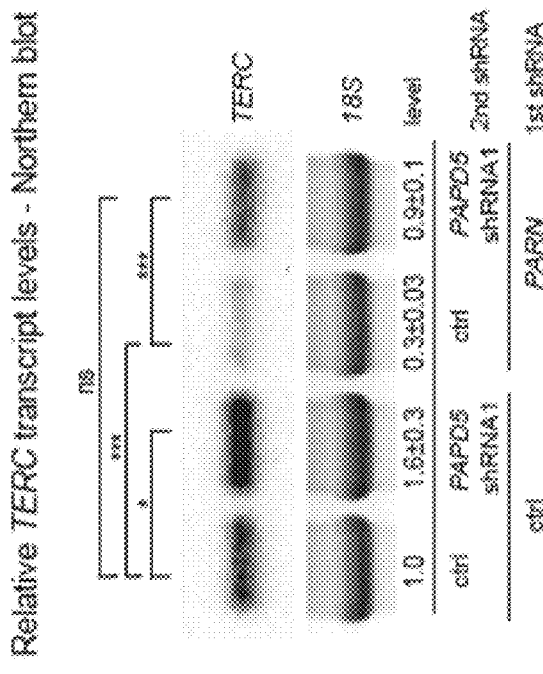
FIG. 11H is a graph showing TRAP assay for telomerase activity in control versus PAPD5 knockdown, PARN deficient HEK293 cells, using 3-fold dilutions of input cell extract.

Notably, TERC RNA was restored in PARN deficient cells by PAPD5 knockdown to levels found in control cells (FIG. 11G). FIG. 11G shows Northern blot of TERC RNA from cells stably transduced with lentivirus encoding shRNA directed against PARN versus luciferase, followed by transduction with lentivirus encoding shRNA directed against PAPD5 versus luciferase. TERC levels are normalized to those in cells with control knockdown. n=3 biological replicates. Standard deviations are indicated. P values: *≤0.05; ***≤0.001; n.s. not significant. To determine the effects of changes in TERC on telomerase function, the telomerase repeat amplification protocol (TRAP) assay was performed and it was noted that PAPD5 knockdown increased telomerase activity in PARN-deficient cells (FIG. 11H). In FIG. 11H, internal control (IC) amplification standard is indicated. n=3 biological replicates.

These data indicate that PAPD5 and PARN mediate opposing and non-redundant effects in the post-transcriptional maturation of nascent TERC transcripts. Despite the presence of other poly(A) polymerases and deadenylases in cells, the manipulation of these two factors significantly impacts TERC RNA levels and cellular telomerase activity.

Figure 12B:
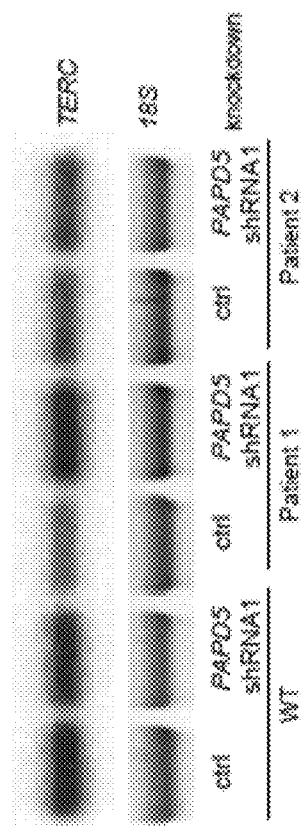
FIG. 12B is a graph showing representative Northern blot of TERC RNA from normal versus PARN-mutant iPSCs stably transduced with lentivirus encoding shRNA directed against PAPD5 versus luciferase.
Figure 12D:
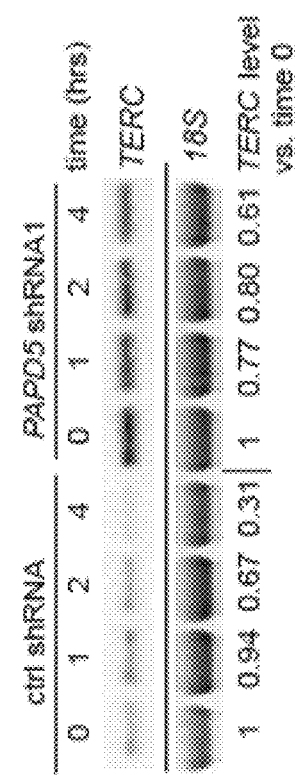
FIG. 12D is a graph showing representative Northern blot of TERC levels in PARN-mutant patient iPSCs after transduction with PAPD5 versus control shRNA, at 0-4 hours following actinomycin treatment.
Figure 12A:
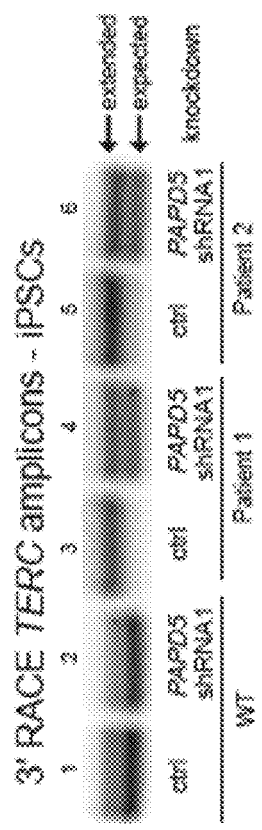
FIG. 12A is a graph showing 3' RACE TERC amplicons from normal (WT) versus PARN-mutant iPSCs stably transduced with lentivirus encoding shRNA directed against PAPD5 versus luciferase as a control (ctrl). n=3 biological replicates.
Figure 12C:
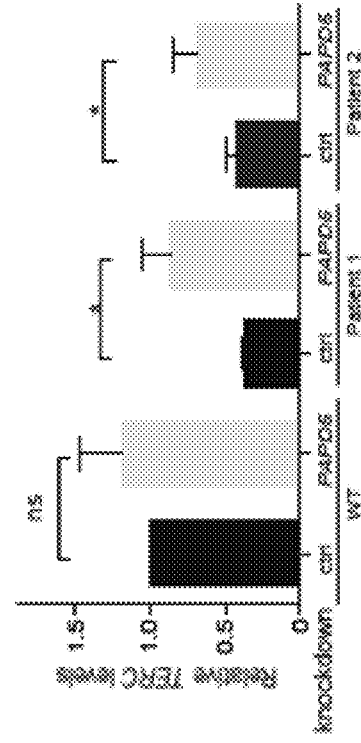
FIG. 12C is a bar graph showing relative TERC levels are normalized to those in normal cells with control knockdown. Average of n=3 biological replicates, standard deviations indicated. P values (*≤0.05; n.s. not significant).
Figure 12E:
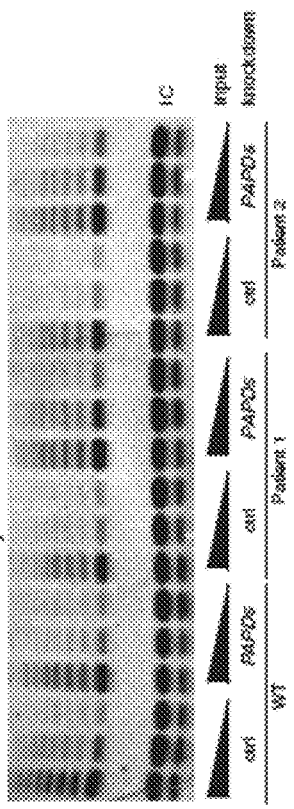
FIG. 12E is a graph of TERC decay rate in PARN-mutant patient iPSCs after transduction with PAPD5 versus control shRNA.

PAPD5 Inhibition Restores TERC Processing, TERC Levels, Telomerase Activity and Telomere Elongation in DC Patient Cells The results indicate that TERC is limiting in PARN-deficient cells due to inadequate deadenylation of nascent TERC transcripts, and that this effect can be reversed by inhibiting the major adenylating activity, PAPD5. Therefore, it is important to determine whether inhibiting post-transcriptional adenylation by PAPD5 could reverse molecular features of telomere disease in PARN-mutant DC patient cells. Induced pluripotent stem cells (iPSCs) were transduced from two DC patients harboring pathogenic PARN mutations with lentiviral vectors encoding PAPD5 shRNA. By 3' RACE, PARN-mutant patient cells show a predominance of extended TERC forms (FIG. 12A, lanes 1, 3, and 5). This altered distribution of TERC species in PARN-mutant patient cells was normalized by PAPD5 knockdown, as evidenced by an increase in the proportion of amplicons corresponding to the mature form of TERC (FIG. 12A). Accordingly, by Northern blot, PAPD5 inhibition rescued total TERC levels in patient iPSCs (FIG. 12B-12C). The increased TERC steady state levels were due to higher stability of RNA transcripts, which were demonstrated by inhibiting Pol II transcription using actinomycin D in patient iPSCs with or without PAPD5 inhibition. When decay rates by Northern blot was compared, it was noted that PAPD5 knockdown increased the half-life of TERC transcripts in PARN-mutant patient iPSCs compared to cells expressing control shRNA (FIG. 12D-12E). In FIG. 12D, normalized TERC levels relative to time 0 for each sample are indicated. In FIG. 12E, n=2 biological replicates. Dashed line reflects slope determined by simple linear regression. Collectively, these results indicate that PAPD5 inhibition is sufficient to restore TERC processing, stability and steady-state levels in the setting of PARN mutations.

Figure 12F:
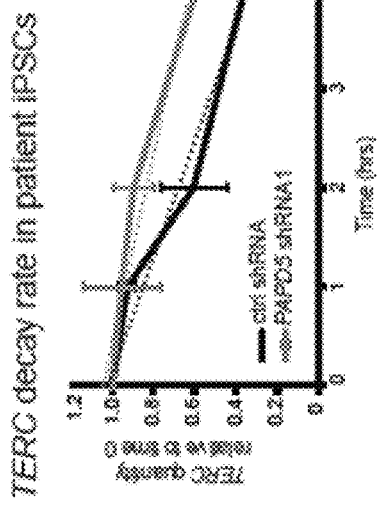
FIG. 12F is a graph showing TRAP assay in normal versus PARN-mutant iPSCs stably transduced with lentivirus encoding shRNA directed against PAPD5 versus luciferase.
Figure 12G:
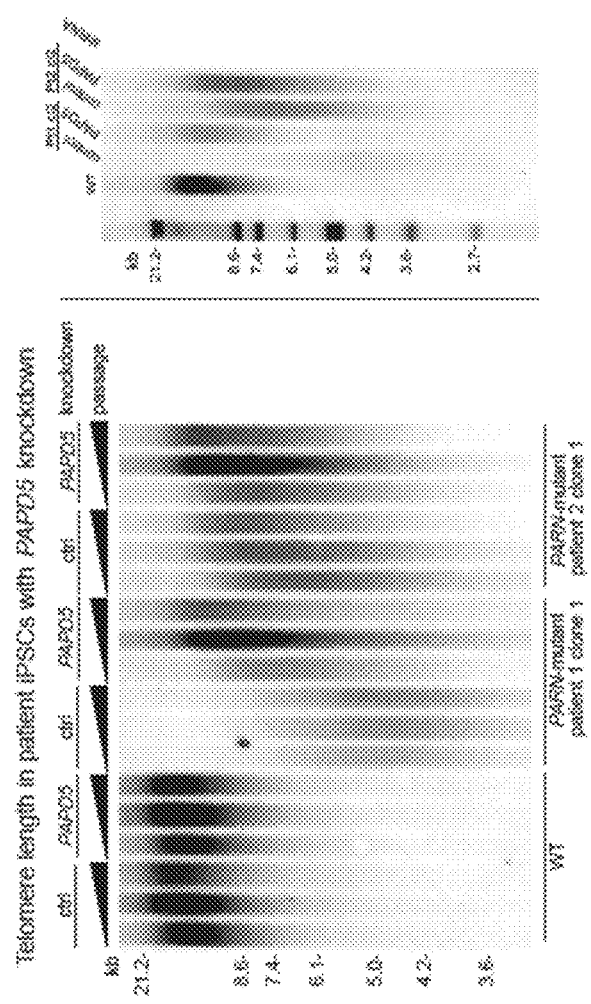
FIG. 12G are graphs showing TRF length analysis of normal (WT) and PARN-mutant patient iPSCs, stably transduced with lentivirus expressing shRNA against PAPD5 versus luciferase (ctrl), over time in culture (20 passages; ~10 weeks) (left), and TRF length analysis of additional clones of PARN-mutant patient iPSCs, 12 passages (~6 weeks) after transduction (right).

The next question was whether PAPD5 inhibition would be sufficient to rescue telomerase activity and telomere elongation. Using TRAP assays, it was noted that PAPD5 inhibition in PARN-mutant patient iPSCs using a lentivirus-encoded shRNA increased cellular telomerase activity (FIG. 12F; n=3 biological replicates). Remarkably, when telomere length was assayed by Southern blot, it was noted that PAPD5 knockdown in PARN-mutant patient iPSCs led to a rapid increase in telomere lengths, approximating those found in control iPSCs (FIG. 12G). Patient iPSCs with stable PAPD5 knockdown showed continuous self-renewal in culture. A global analysis of transcriptional changes after PAPD5 knockdown was performed by RNA sequencing. In patient iPSCs, it was noted that only a small number of transcripts (11 genes) whose levels were altered to a degree that exceeded the increase in TERC; of those, only non-coding RNAs were commonly affected more than would be predicted by chance (Tables 10-12). Taken together, the data indicate that PAPD5 inhibition restores TERC levels, telomerase activity and telomere length in cells from patients with PARN mutations.

Post-Transcriptional Regulation of TERC: A Target for Therapeutic Manipulation

Low TERC levels may be sufficient to explain telomere disease in patients with PARN mutations. Consistent with this hypothesis, TERC expression can restore telomere length in PARN deficient cell lines and PARN-mutant patient cells. These results support the hypothesis that TERC deficiency underlies defective telomere maintenance in patients with PARN mutations. Given the findings of increased oligo-adenylation and destabilization of TERC RNA species in the setting of PARN mutations, the focus is on reversing this post-transcriptional modification as a means of normalizing TERC levels.

The results indicate a critical role for PAPD5 in regulating human TERC biogenesis, a discovery that stems from the findings of PARN mutations in patients with telomere diseases. It was noted that PAPD5 oligo-adenylates and destabilizes nascent TERC transcripts in cells. From modulating PARN and PAPD5 individually or in combination, it shows that their functions in TERC maturation are largely non-redundant, despite the presence of other poly(A) polymerases and deadenylases in the cell. The data further show that the increases in TERC levels due to PAPD5 inhibition are sufficient to augment telomerase activity and telomere length in PARN-mutant patient cells, but without a pronounced impact on the transcriptome or cellular viability. A model is proposed where the balance of PARN and PAPD5 activities serves to establish TERC steady state levels, which in turn plays a major role in determining telomerase activity and telomere maintenance in TERT-expressing cells, such as stem cells and cancer cells (FIG. 19). The results provide a novel example of how enzymes that regulate non-coding RNA processing might be targeted to reverse disease phenotypes. Although non-coding RNAs play a variety of roles in diseases, prospective therapies generally depend on delivery of the RNA or anti-sense strategies.

Ectopically expressing TERC is sufficient to extend telomere length in cells from patients with various forms of DC, but this approach poses significant challenges for clinical translation. The results presented here identify PAPD5 as a component of the post-transcriptional machinery potentially amenable to pharmacological inhibition, to restore telomere maintenance in patients with DC and IPF caused by PARN mutations. More broadly, the results suggest an unanticipated therapeutic window for PARN and PAPD5 manipulation that might be exploited to alter telomerase activity and self-renewal in a range of degenerative and malignant diseases (FIG. 19).

Figures 20A, 20B:
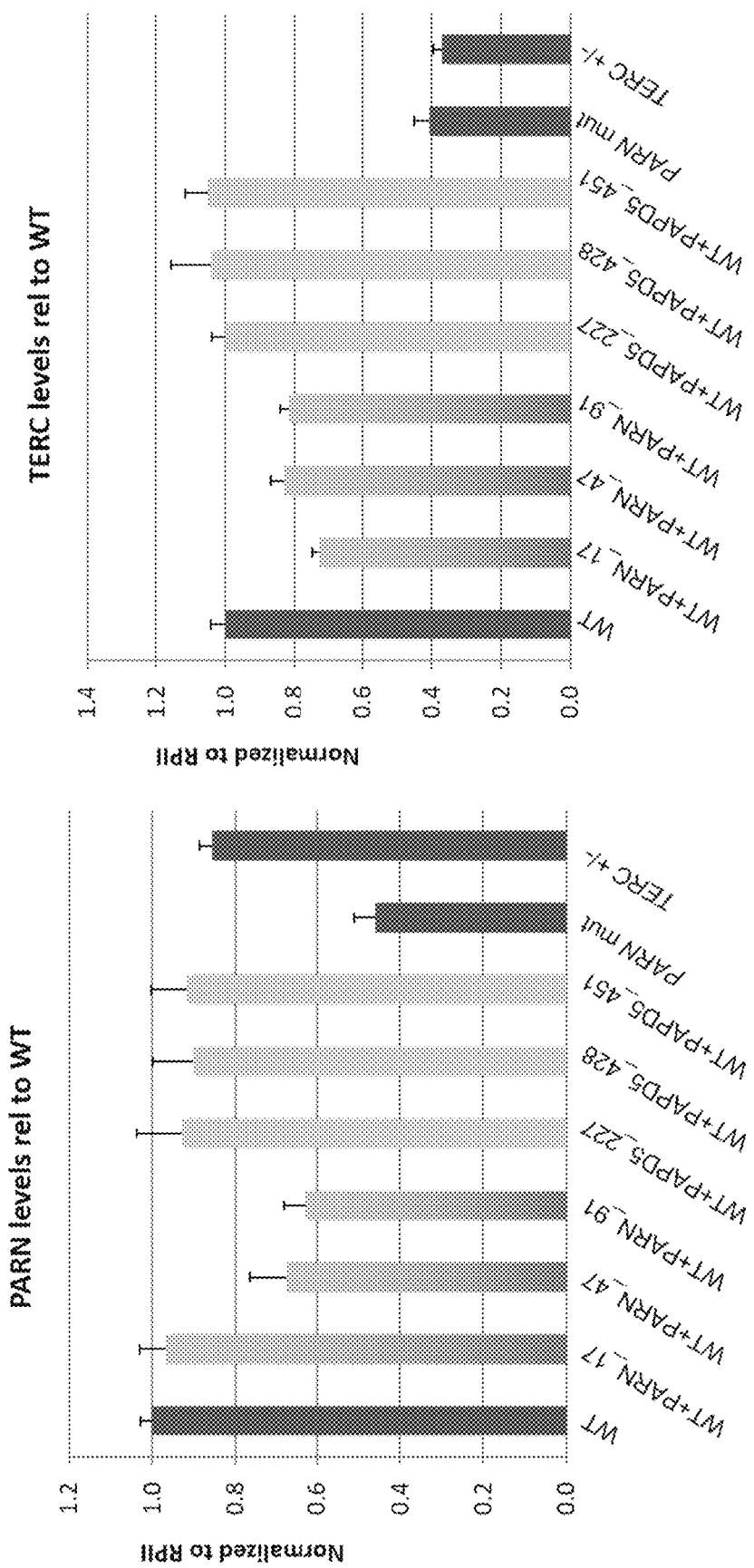
FIG. 20A is a bar graph showing PARN transcript levels by qPCR after CRISPR targeting.
FIG. 20B is a bar graph showing TERC transcript levels by qPCR after CRISPR targeting.
Figures 21A, 21B:
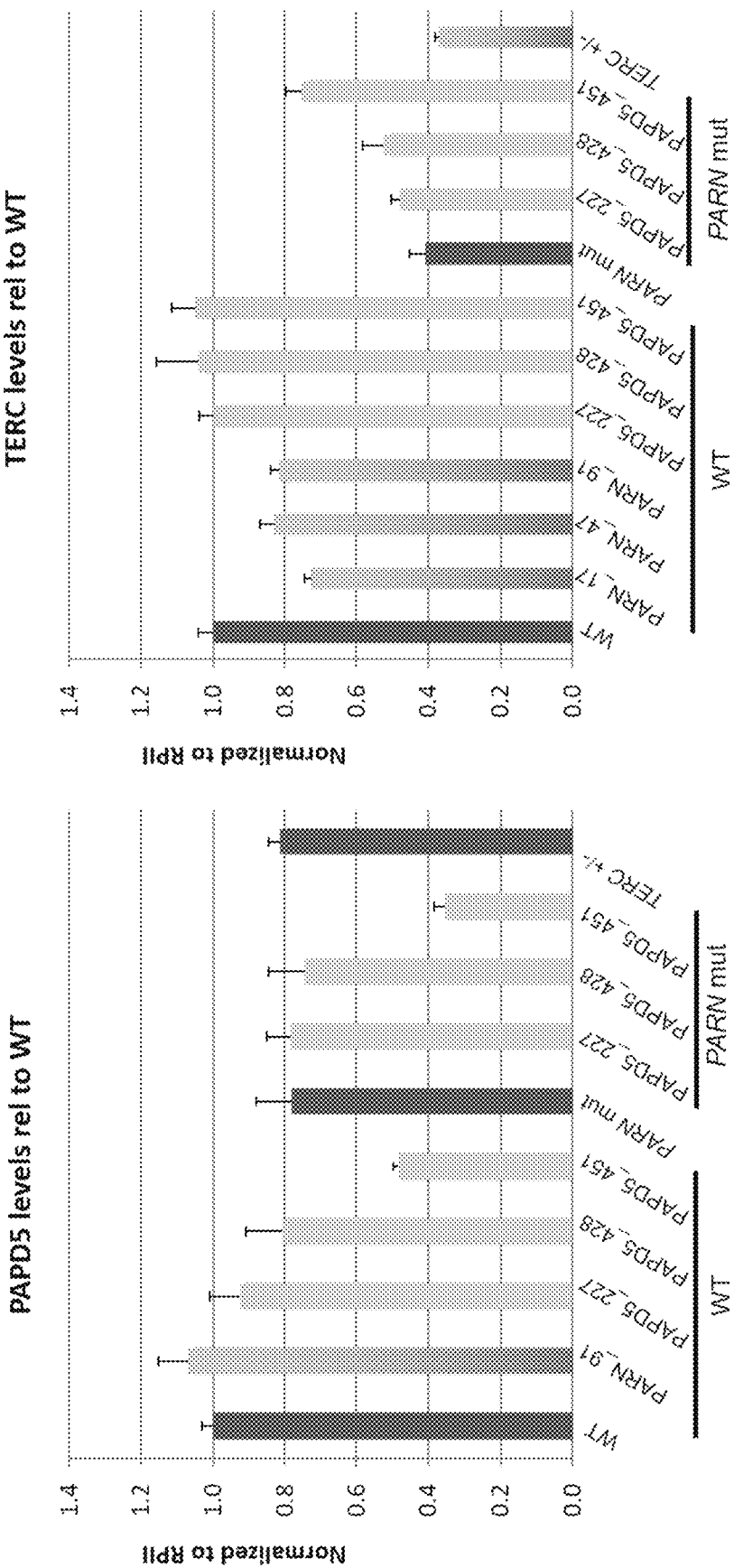
FIG. 21A is a bar graph showing PAPD5 transcript levels by qPCR after CRISPR targeting.
FIG. 21B is a bar graph showing TERC transcript levels by qPCR after CRISPR targeting.
Figure 22:
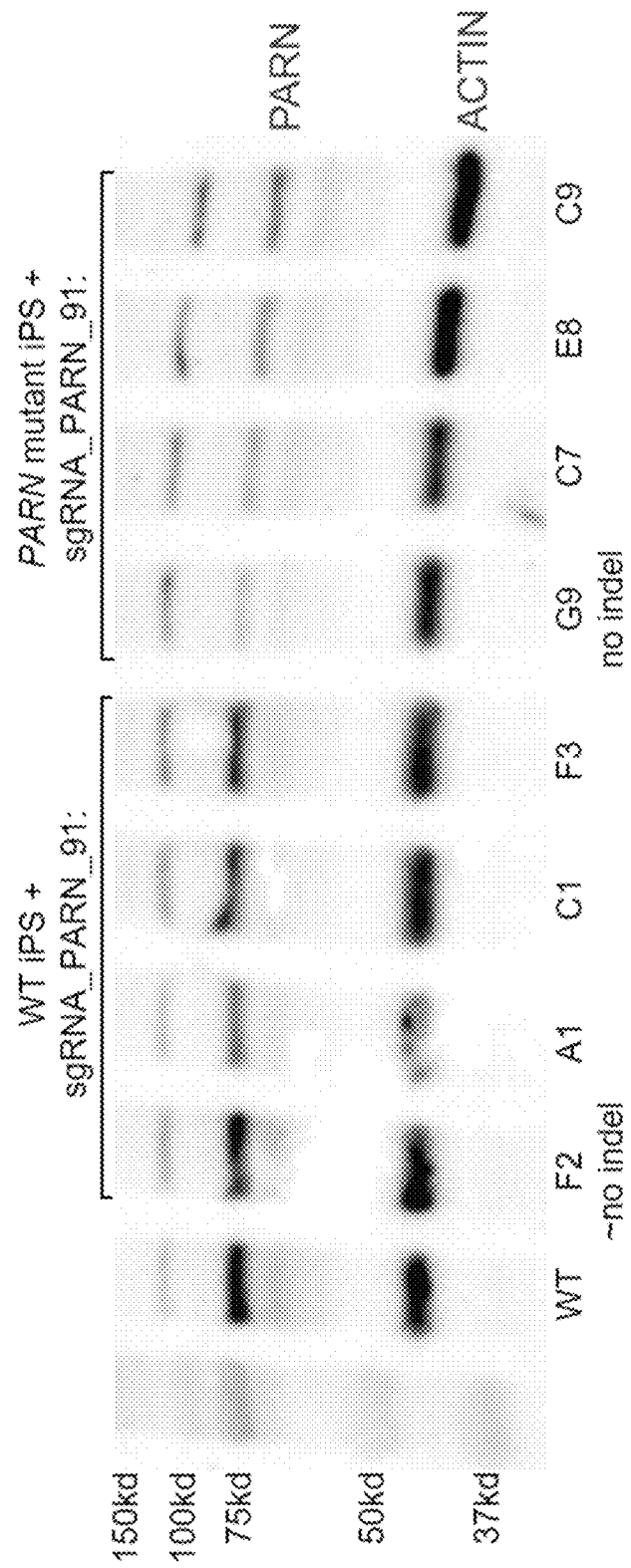
FIG. 22 is a photograph of Western blots showing PARN protein levels in PARN CRISPR iPS clones.
Figure 23:
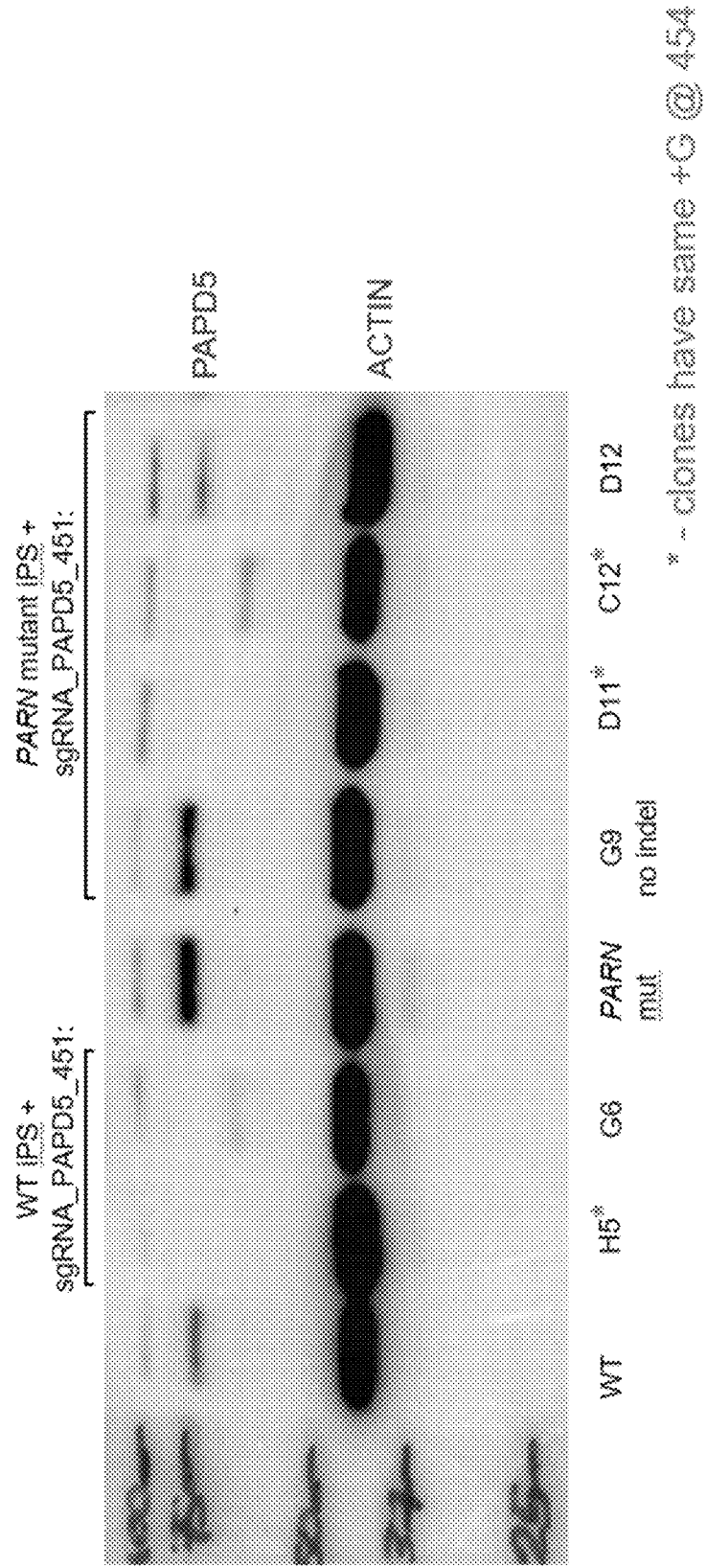
FIG. 23 is a photograph of Western blots showing PAPD5 protein levels in PAPD5 CRISPR iPS clones.
Figure 24:
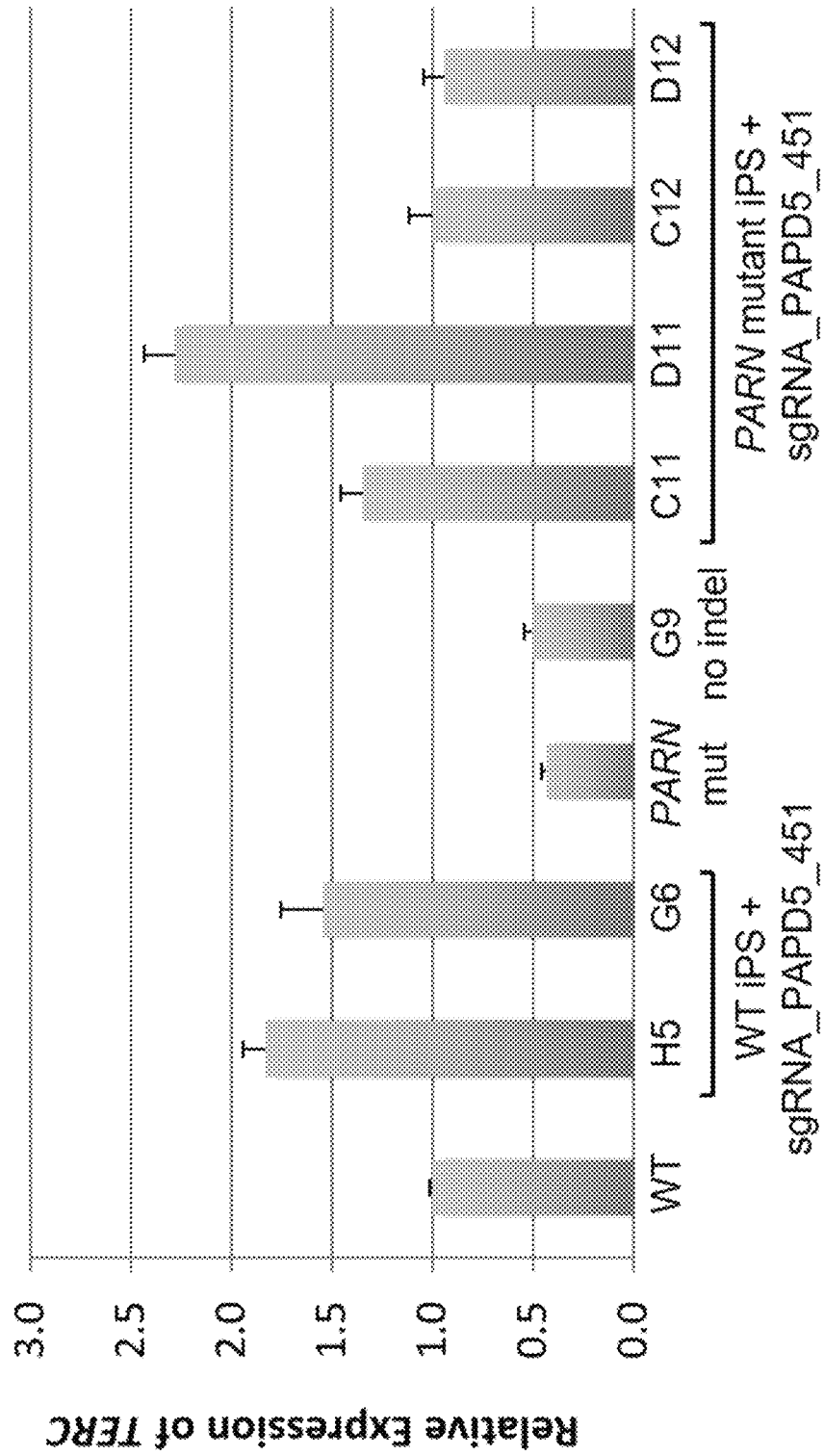
FIG. 24 is a bar graph showing TERC levels in PAPD5 CRISPR iPS Clones.
Figure 25:
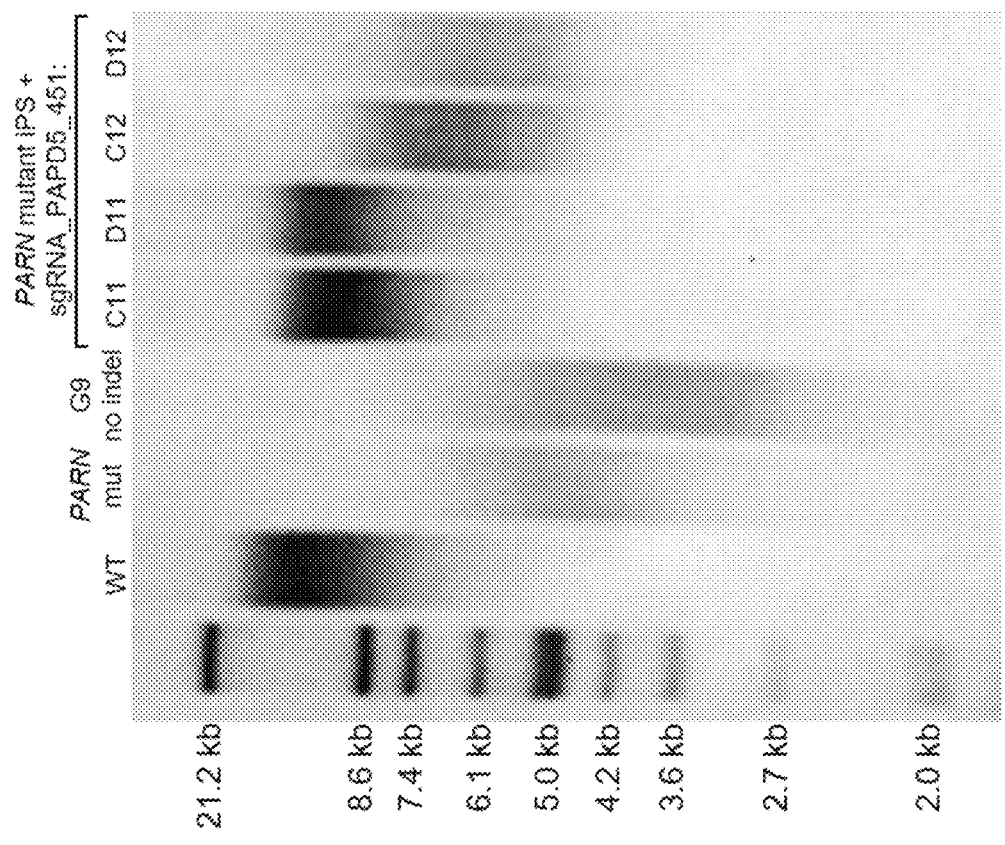
FIG. 25 is a graph showing telomere length in PAPD5 CRISPR iPS Clones.

Example 11. Post-Transcriptional Manipulation of TERC Reverses Molecular Hallmarks of Telomere Disease Experiments were performed to determine the requirement of PARN and PAPD5 for viability and function of human stem cells. CRISPR/Cas9 genome targeting was performed to create biallelic null mutations. Lentiviral vectors containing guide RNAs (gRNAs; Table 15) to PARN or PAPD5 were designed and used to transduce normal (WT) and PARN mutant induced pluripotent stems (iPSCs), and the frequency of insertion/deletions (indels) were assessed. PARN gRNA 91 created a high frequency of indels and led to reductions in PARN RNA transcript levels as well as TERC RNA levels in WT iPSCs (FIGS. 20A and 20B). For PAPD5, gRNA 451 created the highest frequency of indels and reductions in PAPD5 transcript levels and increases in TERC RNA levels in PARN mutant cells (FIGS. 21A and 21B). Populations of stable lentiviral transduced PARN or PAPD5 targeted iPSCs were subcloned to identify lines with biallelic inactivation of PARN or PAPD5. In cell transduced with PARN gRNAs, only clones with in-frame indels and retained PARN protein expression could be recovered, suggesting a requirement for PARN protein for viability of iPSCs (FIG. 22). In contrast, iPSCs with indels causing frameshifts in PAPD5 and lacking PAPD5 protein could be isolated (FIG. 23). Inactivation of PAPD5 by CRISPR/Cas9 augmented TERC levels in iPSC clones (FIG. 24). Southern blot of telomere length by terminal restriction fragment length analysis shows increase in telomere length in PARN mutant IPSCs deficient in PAPD5 (FIG. 25). These results suggest that PAPD5 inactivation is tolerated in human stem cells and augments TERC levels and telomere length, indicating a potentially broad window for therapeutic inhibition of PAPD5 in telomere diseases such as DC and IPF.

Example 12. PAPD5 Inhibitors

Figure 26:
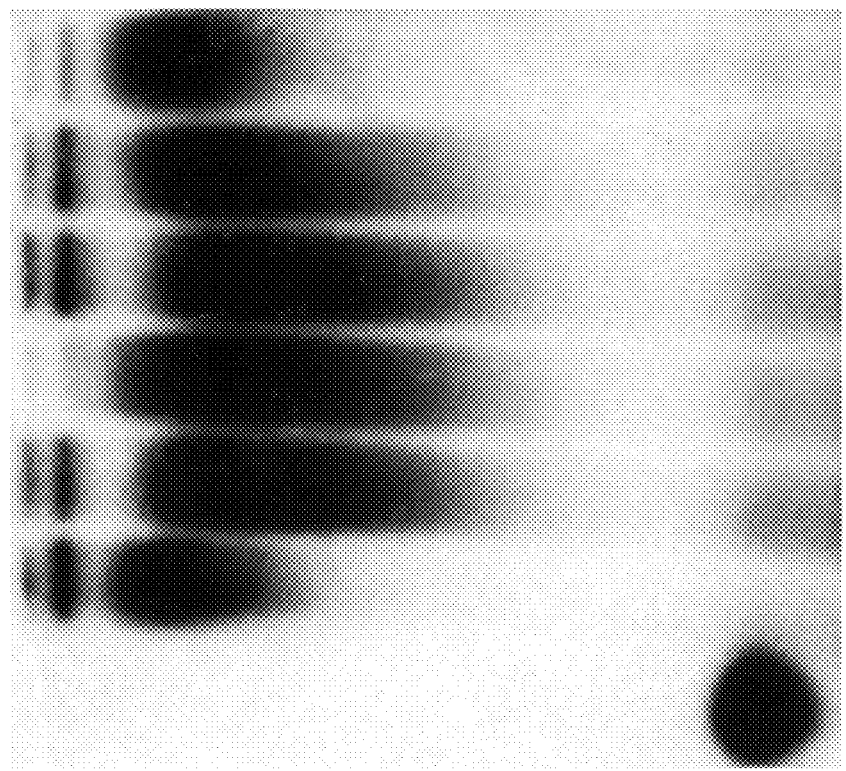
FIG. 26 is a graph showing inhibition of recombinant PAPD5 by aminoglycosides.

Experiments were performed to determine whether aminoglycosides can be used to inhibit PAPD5. 10 μM each of the following are used, (1) Kanamycin B sulfate; (2) Apramycin sulfate; (3) Spectinomycin dihydrochloride pentahydrate; and (4) Ribostamycin sulfate. These results show that each of them can inhibit PAPD5 (FIG. 26).

TABLE 1

Clinical characteristics of patients with PARM mutations

|  | Patient 1 | Patient 2 |
| --- | --- | --- |
| Sex | M | M |
| Age at first presentation | Infancy | 6 years old |
| Age at diagnosis of bone marrow failure | 14 years old | 15 years old |
| Age at diagnosis of DC | 18 years old | 20 years old |
| Current age | 24 years old | 28 years old |
| Manifestations | abnormal skin pigmentation | oral leukoplakia |
|  | nail ridging | abnormal skin pigmentation |
|  | gross motor/speech delay | nail dystrophy |
|  | cerebellar hypoplasia | recurrent urethral strictures |
|  | microcephaly |  |
|  | short stature | lacrimal duct obstruction |
|  | delayed puberty | early graying and hair loss |
|  | dental abnormalities |  |
|  | bone marrow failure | bone marrow failure |
|  | status-post bone marrow transplantation | cirrhosis |
|  |  | decreased diffusion capacity of the lung |
|  | osteopenia/pathological fracture |  |
|  | progressive hypoxia due to pulmonary arteriovenous malformations |  |
| Relevant family history | Pulmonary fibrosis (paternal grandfather) | Pulmonary fibrosis (maternal grandfather) |
| Diagnosis | DC/Hoyeraal Hreidarrson syndrome (HHS) overlap | Classic DC |

TABLE 2

In silico evaluation of PARN missense notations

|  | Patient 1 | Patient 2 |
| --- | --- | --- |
| Chromosome position | chr16: 14723964 | chr16: 14721030 |
| annotation | NM_002582: exon1: c.19A > C | NM_002562: exon1: c.260C > T |
| region | exonic; splicing | exonic |
| dbSNP139 | — | — |
| Exome variant server | — | — |
| 1000 G | — | — |
| change | nonsynonymous; p.N7H | nonsynonymous; p.S87L |
| Polyphen2 (HumDiv/HumVar) | Probably damaging/probably damaging (1.000/0.985) | Probably damaging/possibly damaging (0.983/0.799) |
| SIFT | Damaging (0.03) | Damaging (0.02) |
| PROVEAN (cutoff = −2.5) | Deleterious (−4.041) | Deleterious (−3.153) |
| Mutation Taster | Disease-causing | Disease-causing |

TABLE 3

RNA-Seq transcriptome analysis in PARN deficient cells

| | Total genes analyzed | Altered across all 7 pair-wise comparisons | | | Altered in any 6 of 7 pair-wise comparisons | | | Altered in any 5 of 7 pair-wise comparisons | | |
|---|---|---|---|---|---|---|---|---|---|---|
| | | Obs | Exp | p-value | Obs | Exp | p-value | Obs | Exp | p-value |
| Decreased | | | | | | | | | | |
| mRNA | 12937 | *0* | *0.96* | *0.02* | 1 | 3.83 | 7.0E-09 | *4* | *10.5* | *1.5E-19* |
| rRNA | 63 | 0 | 0 | 1 | 0 | 0.02 | 1 | 0 | 0.05 | 1 |
| snoRNA | 249 | 1 | 0.02 | 0.0003 | 3 | 0.07 | 1.9E-19 | 6 | 0.2 | 1.5E-32 |
| snRNA | 259 | 0 | 0.02 | 1 | 0 | 0.06 | 1 | 1 | 0.21 | 0.52 |
| Increased | | | | | | | | | | |
| mRNA | 12937 | 0 | | NA | 1 | 1.92 | 0.14 | 0 | 10.5 | 0.12 |
| rRNA | 63 | 0 | | NA | 0 | 0.01 | 1 | 0 | 0.05 | 1 |
| snoRNA | 249 | 0 | | NA | 1 | 0.04 | 0.01 | 2 | 0.2 | 0.004 |
| snRNA | 259 | 0 | | NA | 0 | 0.04 | 1 | 0 | 0.21 | 1 | mRNA: protein-coding mRNA;
rRNA: ribosomal RNA;
snoRNA: small nucleolar RNA (includes box H/ACA, C/D, soaRNA);
snRNA: small nuclear RNA
Obs: observed;
Exp: expected by chance;
NA: not analyzed.
Bold: significantly more than expected;
Italic: significantly fewer than expected

TABLE 4

Genes whose transcript levels are consistently altered
Genes whose transcript levels are consistently altered in excess of the fold-change in TERC levels, in 7 pair-wise comparisons of PARN deficient versus normal cells

| | Across all 7 comparisons | Across any 6 of 7 comparisons | Across any 5 of 7 comparisons |
|---|---|---|---|
| Decreased | SCARNA13 | SCARNA13<br>FAM24B<br>SCARNA22<br>SNORA42 | SCARNA13<br>FAM24B<br>SCARNA22<br>SNORA42<br>HIST1H2AK<br>MTRNR2L1<br>RNU6-767P<br>SNORA73<br>SNORD114-21<br>SNORD7<br>ZSWM7 |
| Increased | none | SNORA7A<br>UPK3BL | SNORA7A<br>UPK3BL<br>ANKRD1<br>CYR61<br>DACT1<br>EIF5A2<br>FLT1<br>LGMN<br>NDUFV1<br>SNORA77<br>TAS2R31 |

TABLE 5

Primers for sequencing the human PARN gene

| Name | SEQ ID NO: | Primer Sequence |
|---|---|---|
| PARN ex1,2_L | 3 | GAGGGAAAGGAGCCCAGCCTTG |
| PARN ex1,2_R | 4 | TGAAGGAGCCTTGGCTATGCACTG |
| PARN ex3_L | 5 | GGGTTTAACCTGGTGGCCACTGAA |
| PARN ex3_R | 6 | ATTGGCTGGGCACAGTGGCTTG |
| PARN ex4,5_L | 7 | AGCCCACCTGTTTGAGAATG |
| PARN ex4,5_R | 8 | CCCCAAAGCCCAAAGTTAAT |
| PARN ex6_L | 9 | TCCTGCCGCTAACATCCCCAAA |
| PARN ex6_R | 10 | GGCTGCATATGTGTACTGGCTGCAC |
| PARN ex7_L | 11 | CTAAGCGTGCATTGTGTGCT |
| PARN ex7_R | 12 | GCACTTATGCTGTGCCAAAG |
| PARN ex8,9_L | 13 | TCTTGGTTGATGACTTCATTCC |
| PARN ex8,9_R | 14 | CCGCAGAATTTCAAAAAGGA |
| PARN ex10_L | 15 | GAGCAAGGGTAAGGAAACATTTAGCA |
| PARN ex10_R | 16 | TAGCCAAGCATGGTGGCACGAG |
| PARN ex11_L | 17 | TAATCGCTTGAACCCAGGAG |
| PARN ex11_R | 18 | CCAGGTTTTTCTGCCAATTC |
| PARN ex12_L | 19 | CGCAAAGCACAGGAAACTAA |
| PARN ex12_R | 20 | CAAGGCTCCCTGAAAATTGA |
| PARN ex13_L | 21 | CCAAAATGGAGGAGGAATGA |
| PARN ex13_R | 22 | TCTGGGAACATGCTGCATAC |
| PARN ex14_L | 23 | CCCAACAGCTTGTTTGAGAAG |
| PARN ex14_R | 24 | CTCCTGGGTTCAAGCAATTC |

TABLE 5-continued

Primers for sequencing the human PARN gene

| Name | SEQ ID NO: | Primer Sequence |
|---|---|---|
| PARN ex15,16_L | 25 | TCAAAATGGCCAATGTGTTT |
| PARN ex15,16_R | 26 | CCAGAGCCATTCTGCTTTTC |
| PARN ex17_L | 27 | GATTGGTAGGGCAATGTGCT |
| PARN ex17_R | 28 | CCATCTGCAAACCAGGAAGT |
| PARN ex18_L | 29 | TGTTTTGGTCTGAACTTTCAGGCTTGG |
| PARN ex18_R | 30 | ACACCCGGCCCCTCATAGGAAA |
| PARN ex19_L | 31 | GTTGCAGTGAGCCAAGATCA |
| PARN ex19_R | 32 | CACAGCCCAATTTTGAGTGA |
| PARN ex20_L | 33 | TTCAAGTTGTTGTGGGTTCTG |
| PARN ex20_R | 34 | TCTTTTATACGCAGGCCAAAA |
| PARN ex21_L | 35 | GCCTTTGAACAGGCTAACTCTC |
| PARN ex21_R | 36 | AAAACAAACGAGGCAGCAAT |
| PARN ex22_L | 37 | TTGACCACCTTAGGCCACAT |
| PARN ex22_R | 38 | AGGCCATCTTTCCCAAAAGT |
| PARN ex23_L | 39 | TGATGGCTGGCTGAGTGTTA |
| PARN ex23_R | 40 | CACCAAGTGAAGCCTTGCTA |
| PARN ex24_L | 41 | CTCTTGTGAGGCCTTTCCTG |
| PARN ex24_R | 42 | AGCATGACATGACCAGCAGA |

TABLE 6

Oligonucleotides and primers

| Primer Name | SEQ ID NO: | Sequence |
|---|---|---|
| PARN_L | 43 | CCCTTAGCCAGCCCGAGCAAGT |
| PARN_R | 44 | ACTCCGTCCTCCAGGCCAGCTT |
| PARN_L2 | 45 | CAGGCCATAGAGGAGGCCGACTT |
| PARN_R2 | 46 | CTCCTGCACCATTCGCCTGTGA |
| PARN copy_ex1L | 47 | AAGTCGCGGCCGGCGTCACC |
| PARN copy ex1R | 48 | TGGCCTGGTACACTTTGTGAAGA |
| PARN copy ex24L | 49 | GGTACGGCAGCGTGTGTGCGTA |
| PARN copy ex24R | 50 | TCTGAAGCGGGTGGAGCAAAGC |
| PARN cDNA_ex3L | 51 | TCAGTGATGGACCTTCAGTCTCTGCAT |
| PARN cDNA_ex4L | 52 | TGCTATTTCAGTTTGGCCTTTGCAC |
| PARN cDNA ex5RWT | 53 | GGTTTCGGGAAAACATAGAAGTTAAATG |
| PARN cDNA ex6R | 54 | TCAATGCTGGAGCTCTGACAAACA |
| TERC_L1 | 55 | GGGAGGGGTGGTGGCCATTTTT |
| TERC_L2 | 56 | CACCGCGAAGAGTTGGGCTCTG |
| TERC_L3 | 57 | CTCTGTCAGCCGCGGGTCTCTC |
| TERC_L4 | 58 | GGGTTGCGGAGGGTGGGCCT |
| TERC_R1 | 59 | GAACGGGCCAGCAGCTGACATT |
| TERC_R2 | 60 | GCATGTGTGAGCCGAGTCCTGG |
| T7 TERC_L | 61 | TAATACGACTCACTATAGGGGGTTGCGGAGGGTGGGCCTGG |
| Universal RT primer | 62 | CTACGTAACGATTGATGGTGCCTACAG |
| GPR15 copy_L | 63 | TGCATTGCAAGGAAGCTGTGTGC |
| GPR15 copy_R | 64 | TTGCCGCAACOCAGAGACAATG |
| POLR2A_L | 65 | GCTTGATGCGGGTGCTGAGTGA |
| POLR2A_R | 66 | GTCCTGGCGGTTGACTCCGTGT |
| DKC1_L | 67 | ACAGGGTGAAGAGTTCTGGCACAT |
| DKC1_R | 68 | TGAAGGTGAGGCTTCCAACTCAA |
| ACTB_L | 69 | ATGATGATATCGCCGCGCTCGT |
| ACTB_R | 70 | TGCCGTGCTCGATGGGTACTT |
| U1 SnRNA_L | 71 | ATACTTACCTGGCAGGGGAGATA |
| U1 SnRNA_R | 72 | GGGAAAGCGCGAACGCAGTC |
| pLIKO_seq_L | 73 | CCCCCTTCACCGAGGGCCTA |
| PARN shRNA1 | 74 | CCGGCCGCACTGTATTTAACTTAATCTCGAGATTAAGTTAAATACAGTGCGGTTTTTG |
| PARN shRNA2 | 75 | CCGGGCCTTTGGTAACATTCAGATACTCGAGTATCCAATGTTCTATATGTGGCTTTTTG |
| luciferase shRNA | 76 | CCGGCGCTGAGTACTTCGAAATGTCCTCGAGGACATTTCGAAGTACTCAGCGTTTTTG |

TABLE 7

TERC-defined thresholds

| Group 1 | Group 2 | TERC-defined threshold fold-change in (ln(1 + TPM)) |
|---|---|---|
| WT1 FIB | Patient 1 FIB | 0.86 |
| WT2 FIB | Patient 1 FIB | 0.91 |
| WT1 iPS | Patient 1 cl2 iPS | 0.57 |
| WT1 iPS | Patient 2 cl1 iPS | 0.36 |
| WT2 iPS | Patient 1 cl2 iPS | 0.51 |
| WT2 iPS | Patient 2 cl1 iPS | 0.30 |
| 293 control KD | 293 PARN KD | 0.85 |

TABLE 8

Primers and shRNA sequences for TRF4-2

| Name | SEQ ID NO: | Sequence |
|---|---|---|
| PARN_L | 43 | CCCTTAGCCAGCCCGAGCAAGT |
| PARN_R | 44 | ACTCCGTCCTCCAGGCCAGCTT |
| TRF4-2_L | 77 | AGGGAGTCGTGGGTCTGCATGAA |
| TRF4-2_R | 78 | ATATCTGGACGTCAGCGCTGGG |
| TERC_L | 57 | CTCTGTCAGCCGCGGGTCTCTC |
| Universal RT | 62 | CTACGTAACGATTGATGGTGCCTACAG |
| POLR2A_L | 65 | GCTTGATGCGGGTGCTGAGTGA |
| POLR2A_R | 66 | GTCCTGGCGGTTGACTCCGTGT |
| PARN shRNA1 | 74 | CCGGCGCACTGTATTTAACTTAATCTCG AGATTAAGTTAAATACAGTGCGGTTTTTG |
| luciferase shRNA | 76 | CCGGCGCTGAGTACTTCGAAATGTCCTCG AGGACATTTCGAAGTACTCAGCGTTTTG |
| TRF4-2 shRNA1 | 79 | CCGGGCCACATATAGAGATTGGATACTCG AGTATCCAATCTCTATATGTGGCTTTTG |
| TRF4-2 shRNA2 | 80 | CCGGCCAACAAATCTCAGCATGGATCTCG AGATCCATGCTGAGATTTGTTGGTTTTG |
| TRF4-2 shRNA3 | 81 | CCGGCGCCTGTAATCCCAGCACTTTCTCG AGAAAGTGCTGGGATTACAGGCGTTTTG |
| TRF4-2 shRNA4 | 82 | CCGGGCCTGTAATCCCAGCACTTTACTCG AGTAAAGTGCTGGGATTACAGGCTTTTTG |
| TRF4-2 shRNA5 | 83 | CCGGCGATGTTGGAAGGAGTTCATACTCG AGTATGAACTCCTTCCAACATCGTTTTTG |

TABLE 9

Accession numbers for genes, RNA and proteins

| Gene | Ensembl Gene ID | Nucleotide sequence(s) and variants therein (RefSeq unless otherwise indicated) | Protein ID(s) and variants therein (Uniprot unless otherwise indicated) |
|---|---|---|---|
| TERC | ENSG00000270141 | NR_001566 | N/A |
| PARN | ENSG00000140694 | NM_002582 NM_001242992 NM_001134477 | O95453 |
| TRF4-2 a.k.a. PAPD5 | ENSG00000121274 | NM_001040284 NM_001040285 FR872509.1 (GenBank) | Q8NDF8 H3BQM0 CCB84642.1 (GenBank) |

TABLE 10

RNA-Seq transcriptome analysis of the effects of PAPD5 knockdown: transcripts altered in excess of the fold increase in TERC RNA

| | Total genes analyzed | Altered in any 2 of 3 pair-wise comparisons: HEK 293 and PARN-mutant Patient 1 IPSC clones 1 and 2 | | | Altered in both pair-wise PARN-mutant comparisons: Patient 1 IPSC clones 1 and 2 | | |
|---|---|---|---|---|---|---|---|
| | | Obs | Exp | P-value | Obs | Exp | P-value |
| Decreased | | | | | | | |
| mRNA | 19698 | 30 | 33.7 | 0.34 | 4 | 3.97 | 1 |
| lincRNA | 7670 | 7 | 13.1 | 0.07 | 1 | 1.55 | 0.97 |
| snoRNA | 454 | 7 | 0.78 | 5.9E−11 | 0 | 0.09 | 1 |
| snRNA | 1848 | 7 | 3.2 | 0.05 | 1 | 0.37 | 0.83 |
| Increased | | | | | | | |
| mRNA | 19698 | 47 | 53.6 | 0.15 | 3 | 3.31 | 1 |
| lincRNA | 7670 | *12* | *20.9* | *0.03* | 0 | 1.29 | 0.42 |
| snoRNA | 454 | 11 | 1.2 | 4.0E−17 | 2 | 0.08 | 2.0E-7 |
| snRNA | 1848 | 11 | 5.0 | 0.01 | 0 | 0.31 | 1 | mRNA: protein-coding mRNA;
lincRNA: long intergenic non-coding RNA;
snoRNA: small nucleolar RNA (includes box H/ACA, C/D, scaRNA);
snRNA: small nuclear RNA
Obs: observed;
Exp: expected by chance
Bold: significanty more than expected by chance
Italic: significant fewer than expected by chance

TABLE 11

Genes whose transcript levels are altered in excess of the fold-change in TERC levels, in pair-wise comparisons of PAPD5 knockdown versus control cells

| | Altered in all 3 of 3 pair-wise comparisons: HEK 293 and PARN-mutant Patient 1 iPSC clones 1 and 2 | Altered in both pair-wise PARN-mutant comparisons: Patient 1 iPSC clones 1 and 2 |
|---|---|---|
| Decreased | none | CHURC1-FNTB<br>DEC1<br>GARS<br>RNU6-39P<br>RP4-533D7.6<br>RP4-794H19.1 |
| Increased | SNORD100 | AC018867.1<br>GPAA1<br>SNORA73<br>SNORD100<br>USP7 |

TABLE 12

Genes whose transcript levels are altered in excess of the fold-change in TERC levels, in any 2 of 3 pair-wise comparisons of PAPD5 knockdown versus control: HEK 293 cells and PARN-mutant Patient 1 clones 1 and 2

| Decreased | | | Increased | | |
|---|---|---|---|---|---|
| AARSD1 | RNU6-48P | AC004076.7 | PACRG | RPAP1 | |
| AC069499.1 | RNU6-606P | AC018867.1 | PIAS3 | SCARNA12 | |
| AL592183.1 | RP11-101E3.5 | AC112719.2 | PMM2 | SIGIRR | |
| ANP32B | RP11-2B6.3 | ANKMY1 | PRKAB1 | SLC25A16 | |
| AP001628.6 | RP11-397H6.1 | AP001059.7 | PTCD3 | SLC6A6 | |
| BASP1 | RP11-686D22.5 | BPI | PVR | SLX1B | |
| CD52 | RP11-70F11.11 | BRPF3 | RFXANK | SMTNL2 | |
| CHURC1-FNTB | RP11-895M11.3 | C12orf79 | RMRP | SNORA13 | |
| CTC-273B12.7 | RP4-533D7.6 | C16orf59 | RNU4-86P | SNORA5C | |
| DDX56 | RP4-794H19.1 | C16orf93 | RNU6-1099P | SNORA73 | |
| DEC1 | SCARNA1 | C18orf8 | RNU6-1275P | SNORD100 | |
| DXO | SNORA21 | C1orf127 | RNU6-373P | SNORD116-15 | |
| FKSG63 | SNORA31 | C5orf22 | RNU6-45P | SNORD33 | |
| G0S2 | SNORA55 | CGRRF1 | RNU6-714P | SNORD38A | |
| GARS | SNORA68 | CH507-513H4.5 | RNU7-140P | SNORD46 | |
| HLA-DPA1 | SNORD11 | COMMD3-BMI1 | RNU7-154P | SNORD89 | |
| MILR1 | snoU13 | CTC-435M10.3 | RNU7-181P | SNORD92 | |
| MTRR | SPRR2G | CTD-2302E22.2 | RNU7-77P | SULT1A3 | |
| MVP | TARS | CTD-2313N18.7 | RNVU1-15 | TRMT1 | |
| NDUFS7 | TMEM141 | CYBA | RP11-160E2.6 | UBE2F | |
| NPIPA1 | U2AF1L4 | DNASE1L1 | RP11-171I2.3 | USP7 | |
| OFCC1 | | DPP7 | RP11-245A18.1 | | |
| POLR3GL | | EIF4ENIF1 | RP11-338N10.3 | | |
| PRR4 | | FXYD1 | RP11-38C17.1 | | |
| PSMC3IP | | GABARAP | RP11-430H10.1 | | |
| RNU6-24P | | GEMIN4 | RP11-577B7.1 | | |
| RNU6-307P | | GPAA1 | RP11-644F5.10 | | |
| RNU6-314P | | LINC01360 | RP3-526F5.2 | | |
| RNU6-341P | | NDUFA7 | RP4-539M6.19 | | |
| RNU6-39P | | NOMO3 | RP6-24A23.6 | | |

TABLE 13

DNA oligos and primers

| Oligo/primer name | SEQ ID NO: | DNA Sequence |
|---|---|---|
| PAPD5_L | 77 | AGGGAGTCGTGGGTCTGCATGAA |
| PAPD5_R | 78 | ATATCTGGACGTCAGCGCTGGG |
| POLR2A_L | 65 | GCTTGATGCGGGTGCTGAGTGA |
| POLR2A_R | 66 | GTCCTGGCGGTTGACTCCGTGT |
| TERC_L | 57 | CTCTGTCAGCCGCGGGTCTCTC |
| Universal RT primer | 62 | CTACGTAACGATTGATGGTGCCTACAG |
| TERC_L2 | 58 | GGGTTGCGGAGGGTGGGCCT |
| TERC_R | 60 | GCATGTGTGAGCCGAGTCCTGG |
| Luciferase shRNA | 76 | CCGGCGCTGAGTACTTCGAAATGTCCTCGAGGACATTTCGAAGTACTCAGCGTTTTTG |
| PAPD5 shRNA 1 | 83 | CCGGCGATGTTGGAAGGAGTTCATACTCGAGTATGAACTCCTTCCAACATCGTTTTTG |
| PAPD5 shRNA2 | 79 | CCGGCCACATATAGAGATTGGATACTCGAGTATCCAATCTCTATATGTGGCTTTTTG |

TABLE 14

Antibodies used for Western blot

| Antibody | Source | Catalog # | Dilution |
|---|---|---|---|
| Anti-FLAG HRP | Sigma | A8592 | 1:1000 |
| Anti-PAPD5 | Atlas antibodies | HPA042968 | 1:1000 |
| Goat anti-rabbit | Bio-rad | 170-5046 | 1:15000 |
| Anti-actin HRP | Santa Cruz Biotechnology | Sc-1615 | 1:1000 |

TABLE 15

PARN and PAPD5 targeting guide RNAs for CRISPR/Cas9 genome editing

| gRNA | SEQ ID NO: | TARGET SEQ + PAM |
|---|---|---|
| PAPD5_227 | 84 | CGGAGCGATACATGCCGGCCGGG |
|  | 85 | CGGAGCGATACATGCCGGCC |
| PAPD5_428 | 86 | CGCCGCCGATCCAGCCGATTCGG |
|  | 87 | CGCCGCCGATCCAGCCGATT |
| PAPD5_451 | 88 | CCTCTTGTTGCTGCTGCCCGAGG |
|  | 89 | CCTCTTGTTGCTGCTGCCCG |
| PARN_17 | 90 | TAATCTTCACAAAGTGTACCAGG |
|  | 91 | TAATCTTCACAAAGTGTACC |
| PARN_47 | 92 | GTATGATGAAAAACGTTCACAGG |
|  | 93 | GTATGATGAAAAACGTTCAC |
| PARN_91 | 94 | TGAAGTGTTAGGAGATACATAGG |
|  | 95 | TGAAGTGTTAGGAGATACAT |

REFERENCES

1. Stuart, B. D. et al. Exome sequencing links mutations in PARN and RTEL1 with familial pulmonary fibrosis and telomere shortening. *Nat Genet* 47, 512-7 (2015).
2. Tummala, H. et al. Poly(A)-specific ribonuclease deficiency impacts telomere biology and causes dyskeratosis congenita. *J Clin Invest* 125, 2151-60 (2015).
3. Dehlin, E., Wormington, M., Korner, C. G. & Wahle, E. Cap-dependent deadenylation of mRNA. *The EMBO journal* 19, 1079-86 (2000).
4. Korner, C. G. & Wahle, E. Poly(A) tail shortening by a mammalian poly(A)-specific 3'-exoribonuclease. *The Journal of biological chemistry* 272, 10448-56 (1997).
5. Korner, C. G. et al. The deadenylating nuclease (DAN) is involved in poly(A) tail removal during the meiotic maturation of Xenopus oocytes. *EMBO J* 17, 5427-37 (1998).
6. Virtanen, A., Henriksson, N., Nilsson, P. & Nissbeck, M. Poly(A)-specific ribonuclease (PARN): an allosterically regulated, processive and mRNA cap-interacting deadenylase. *Crit Rev Biochem Mol Biol* 48, 192-209 (2013).
7. Yoda, M. et al. Poly(A)-specific ribonuclease mediates 3'-end trimming of Argonaute2-cleaved precursor microRNAs. *Cell Rep* 5, 715-26 (2013).
8. Berndt, H. et al. Maturation of mammalian H/ACA box snoRNAs: PAPD5-dependent adenylation and PARN-dependent trimming. *RNA* 18, 958-72 (2012).
9. Mason, P. J. & Bessler, M. mRNA deadenylation and telomere disease. *J Clin Invest* 125, 1796-8 (2015).
10. Egan, E. D. & Collins, K. An enhanced H/ACA RNP assembly mechanism for human telomerase RNA. *Mol Cell Biol* 32, 2428-39 (2012).
11. Feng, J. et al. The RNA component of human telomerase. *Science* 269, 1236-41 (1995).
12. Venteicher, A. S. et al. A human telomerase holoenzyme protein required for Cajal body localization and telomere synthesis. *Science* 323, 644-8 (2009).
13. Greider, C. W. Telomerase RNA levels limit the telomere length equilibrium. *Cold Spring Harbor symposia on quantitative biology* 71, 225-9 (2006).
14. Cristofari, G. & Lingner, J. Telomere length homeostasis requires that telomerase levels are limiting. *The EMBO journal* 25, 565-74 (2006).
15. Cao, Y., Bryan, T. M. & Reddel, R. R. Increased copy number of the TERT and TERC telomerase subunit genes in cancer cells. *Cancer science* 99, 1092-9 (2008).
16. Soder, A. I. et al. Amplification, increased dosage and in situ expression of the telomerase RNA gene in human cancer. *Oncogene* 14, 1013-21 (1997).
17. Heiss, N. S. et al. X-linked dyskeratosis congenita is caused by mutations in a highly conserved gene with putative nucleolar functions. *Nat Genet* 19, 32-8 (1998).
18. Mitchell, J. R., Wood, E. & Collins, K. A telomerase component is defective in the human disease dyskeratosis congenita. *Nature* 402, 551-5 (1999).
19. Vulliamy, T. et al. Mutations in the telomerase component NHP2 cause the premature ageing syndrome dyskeratosis congenita. *Proceedings of the National Academy of Sciences of the United States of America* 105, 8073-8 (2008).
20. Vulliamy, T. et al. The RNA component of telomerase is mutated in autosomal dominant dyskeratosis congenita. *Nature* 413, 432-5 (2001).
21. Walne, A. J. et al. Genetic heterogeneity in autosomal recessive dyskeratosis congenita with one subtype due to mutations in the telomerase-associated protein NOP10. *Human molecular genetics* 16, 1619-29 (2007).
22. Mitchell, J. R., Cheng, J. & Collins, K. A box H/ACA small nucleolar RNA-like domain at the human telomerase RNA 3' end. *Molecular and cellular biology* 19, 567-76 (1999).
23. Houseley, J. & Tollervey, D. The many pathways of RNA degradation. *Cell* 136, 763-76 (2009).
24. Schmidt, K. & Butler, J. S. Nuclear RNA surveillance: role of TRAMP in controlling exosome specificity. *Wiley Interdiscip Rev RNA* 4, 217-31 (2013).
25. Kiss, T., Fayet-Lebaron, E. & Jady, B. E. Box H/ACA small ribonucleoproteins. *Molecular cell* 37, 597-606 (2010).
26. Rammelt, C., Bilen, B., Zavolan, M. & Keller, W. PAPD5, a noncanonical poly(A) polymerase with an unusual RNA-binding motif. *RNA* 17, 1737-46 (2011).
27. LaCava, J. et al. RNA degradation by the exosome is promoted by a nuclear polyadenylation complex. *Cell* 121, 713-24 (2005).
28. Fu, D. & Collins, K. Distinct biogenesis pathways for human telomerase RNA and H/ACA small nucleolar RNAs. *Molecular cell* 11, 1361-72 (2003).
29. Zaug, A. J., Linger, J. & Cech, T. R. Method for determining RNA 3' ends and application to human telomerase RNA. *Nucleic acids research* 24, 532-3 (1996).
30. Goldfarb, K. C. & Cech, T. R. 3' terminal diversity of MRP RNA and other human noncoding RNAs revealed by deep sequencing. *BMC molecular biology* 14, 23 (2013).
31. Jongmans, M. C. et al. Revertant somatic mosaicism by mitotic recombination in dyskeratosis congenita. *American journal of human genetics* 90, 426-33 (2012).

32. Kirwan, M. et al. Exogenous TERC alone can enhance proliferative potential, telomerase activity and telomere length in lymphocytes from dyskeratosis congenita patients. *British journal of haematology* 144, 771-81 (2009).
33. Westin, E. R. et al. Telomere restoration and extension of proliferative lifespan in dyskeratosis congenita fibroblasts. *Aging Cell* 6, 383-94 (2007).
34. Wong, J. M. & Collins, K. Telomerase RNA level limits telomere maintenance in X-linked dyskeratosis congenita. *Genes & development* 20, 2848-58 (2006).
35. Hao, L. Y. et al. Short telomeres, even in the presence of telomerase, limit tissue renewal capacity. *Cell* 123, 1121-31 (2005).
36. Alter, B. P., Giri, N., Savage, S. A. & Rosenberg, P. S. Cancer in dyskeratosis congenita. *Blood* 113, 6549-57 (2009).
37. Armanios, M. Y. et al. Telomerase mutations in families with idiopathic pulmonary fibrosis. *The New England journal of medicine* 356, 1317-26 (2007).
38. Calado, R. T. et al. Constitutional telomerase mutations are genetic risk factors for cirrhosis. *Hepatology* 53, 1600-7 (2011).
39. Kirwan, M. et al. Defining the pathogenic role of telomerase mutations in myelodysplastic syndrome and acute myeloid leukemia. *Human mutation* 30, 1567-73 (2009).
40. Tsakiri, K. D. et al. Adult-onset pulmonary fibrosis caused by mutations in telomerase. *Proceedings of the National Academy of Sciences of the United States of America* 104, 7552-7 (2007).
41. Yamaguchi, H. et al. Mutations of the human telomerase RNA gene (TERC) in aplastic anemia and myelodysplastic syndrome. *Blood* 102, 916-8 (2003).
42. Trapp, S. et al. A virus-encoded telomerase RNA promotes malignant T cell lymphomagenesis. *The Journal of experimental medicine* 203, 1307-17 (2006).
43. Codd, V. et al. Common variants near TERC are associated with mean telomere length. *Nature genetics* 42, 197-9 (2010).
44. Soerensen, M. et al. Genetic variation in TERT and TERC and human leukocyte telomere length and longevity: a cross-sectional and longitudinal analysis. *Aging Cell* 11, 223-7 (2012).
45. Lee, J. E. et al. The PARN deadenylase targets a discrete set of mRNAs for decay and regulates cell motility in mouse myoblasts. *PLoS Genet* 8, e1002901 (2012).
46. Aubert, G., Baerlocher, G. M., Vulto, I., Poon, S. S. & Lansdorp, P. M. Collapse of telomere homeostasis in hematopoietic cells caused by heterozygous mutations in telomerase genes. *PLoS Genet* 8, e1002696 (2012).
47. Park, I. H. et al. Reprogramming of human somatic cells to pluripotency with defined factors. *Nature* 451, 141-6 (2008).
48. Park, I. H., Lerou, P. H., Zhao, R., Huo, H. & Daley, G. Q. Generation of human-induced pluripotent stem cells. *Nat Protoc* 3, 1180-6 (2008).
49. Warlich, E. et al. Lentiviral vector design and imaging approaches to visualize the early stages of cellular reprogramming. *Mol Ther* 19, 782-9 (2011).
50. Bolger, A. M., Lohse, M. & Usadel, B. Trimmomatic: a flexible trimmer for Illumina sequence data. *Bioinformatics* 30, 2114-20 (2014).
51. Magoc, T. & Salzberg, S. L. FLASH: fast length adjustment of short reads to improve genome assemblies. *Bioinformatics* 27, 2957-63 (2011).
52. Langmead, B. & Salzberg, S. L. Fast gapped-read alignment with Bowtie 2. *Nat Methods* 9, 357-9 (2012).
53. Kim, D., Langmead, B. & Salzberg, S. L. HISAT: a fast spliced aligner with low memory requirements. *Nat Methods* 12, 357-60 (2015).
54. Patro R, Duggal G, Kingsford C. 2015. Salmon: accurate, versatile and ultrafast quantification from RNA-seq data using lightweight-alignment. bioRxiv doi: 10.1101/021592
55. Rammelt, C. et al. PAPD5, a noncanonical poly(A) polymerase with an unusual RNA-binding motif RNA 17:1737-1746 (2011).
56. Egecioglu, D. et al. Contributions of Trf4p- and Trf5p-dependent polyadenylation to the processing and degradative functions of the yeastnuclear exosome. RNA 12: 26-32 (2006)
57. Berndt H. et al. Maturation of mammalian H/ACA box sno RNAs: PAPD5-dependenet adenylation and PARN-dependent trimming. RNA 18:958-972 (2002)

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing telomerase RNA component (TERC) level or activity in a subject having dyskeratosis congenita, the method comprising:
   a) identifying the subject in need of increasing TERC level or activity; and
   b) administering to the subject an effective amount of a pharmaceutical composition comprising a PAP Associated Domain Containing 5 (PAPD5) inhibitor, wherein the inhibitor is an shRNA comprising a sequence that corresponds to the nucleic acid sequence of SEQ ID NO: 83, thereby increasing TERC level or activity in the subject, wherein the subject has a mutation at PARN, and wherein the subject has a deletion in PARN.

* * * * *

UNITED STATES PATENT AND TRADEMARK OFFICE
CERTIFICATE OF CORRECTION

| | | |
|---|---|---|
| PATENT NO. | : 11,220,689 B2 | |
| APPLICATION NO. | : 15/768424 | |
| DATED | : January 11, 2022 | |
| INVENTOR(S) | : Suneet Agarwal et al. | |

It is certified that error appears in the above-identified patent and that said Letters Patent is hereby corrected as shown below:

In the Specification

Column 1, Lines 18-19, delete "Government support under Grant No. R01 DK107716-01 and T32 HL007574" and insert -- government support under Grant Number DK107716, --.

Signed and Sealed this
Thirtieth Day of January, 2024

Katherine Kelly Vidal
Director of the United States Patent and Trademark Office

SEQUENCE LISTING

```
<160> NUMBER OF SEQ ID NOS: 103

<210> SEQ ID NO 1
<211> LENGTH: 3083
<212> TYPE: DNA
<213> ORGANISM: Homo sapiens

<400> SEQUENCE: 1
aggcgcgcgc tgtttccgga agtcgcggcc ggcgtcaccg ctgcggctgc ctcagctact      60
gccgcagtcg ccgcggaatt cggcgagtag aaccgctgag gcgggcgcgg gcccgggtgg     120
ggccaaggtt ccggccactc tgcagaatgg agataatcag gagcaatttt aagagtaatc     180
ttcacaaagt gtaccaggcc atagaggagg ccgacttctt cgccatcgat ggggagtttt     240
caggaatcag tgatggacct tcagtctctg cattaacaaa tggttttgac actccagaag     300
```

-continued

| | |
|---|---|
| agaggtatca gaagcttaaa aagcattcca tggactttt gctatttcag tttggccttt | 360 |
| gcacttttaa gtatgactac acagattcaa agtatataac gaagtcattt aacttctatg | 420 |
| ttttcccgaa acccttcaat agatcctcac cagatgtcaa atttgtttgt cagagctcca | 480 |
| gcattgactt tctagcaagc cagggatttg attttaataa agttttcga atggaattc | 540 |
| catatttaaa tcaggaagaa gaaagacagt taagagagca gtatgatgaa aaacgttcac | 600 |
| aggcgaatgg tgcaggagct ctgtcctatg tatctcctaa cacttcaaaa tgtcctgtca | 660 |
| cgattcctga ggatcaaaag aagtttattg accaagtggt agagaaaata gaggatttat | 720 |
| tacaaagtga agaaaacaag aacttggatt tagagccatg taccgggttc caagaaaaac | 780 |
| taatttatca gactttgagc tggaagtatc cgaaaggcat tcatgttgag actttagaaa | 840 |
| ctgaaaagaa ggagcgatat atagttatca gcaaagtaga tgaagaagaa cgcaaaagaa | 900 |
| gagagcagca gaaacatgcc aaagaacagg aggagctgaa tgatgctgtg ggattttcta | 960 |
| gagtcattca cgccattgct aattcgggaa aacttgttat tggacacaat atgctcttgg | 1020 |
| acgtcatgca cacagttcat cagttctact gccctctgcc tgcggactta agtgagttta | 1080 |
| aagagatgac aacatgtgtt ttccccagac tcttggatac taaattgatg gccagcacac | 1140 |
| aacctttaa ggatatcatt aacaacacat cccttgcgga attggaaaag cggttaaaag | 1200 |
| agaccctttt caaccctcct aaagttgaaa gtgccgaagg ttttccaagt tatgacacag | 1260 |
| cctctgaaca actccacgag gcaggctacg atgcctacat cacagggctg tgcttcatct | 1320 |
| ccatggccaa ttacctaggt tctttctca gccctccaaa aattcatgtg tctgccagat | 1380 |
| caaaactcat tgaaccttt tttaacaagt tatttcttat gagggtcatg gatatcccct | 1440 |
| atctaaactt ggaaggacca gacttgcagc ctaaacgtga tcatgttctc catgtgacat | 1500 |
| tccccaaaga atggaaaacc agcgaccttt accagctttt cagtgccttt ggtaacattc | 1560 |
| agatatcctg gattgatgac acatcagcat ttgtttccct tagccagccc gagcaagtaa | 1620 |
| agattgctgt caataccagc aaatatgcag aaagctatcg gatccaaacc tatgctgaat | 1680 |
| atatgggag aaaacaggaa gagaagcaga tcaaaagaaa gtggactgaa gatagctgga | 1740 |
| aggaggctga cagcaaacgg ttaaacccccc agtgcatacc ctacaccctg cagaatcact | 1800 |
| attaccgcaa caatagtttt acagctccca gcacagtagg aaagagaaat ttgagtccta | 1860 |
| gtcaagagga agctggcctg gaggacggag tgtcagggga gatttccgac actgagcttg | 1920 |
| agcagaccga ttcctgtgca gagcccctct cagagggaag gaaaaaggcc aagaaattaa | 1980 |
| aaagaatgaa gaaggagctt tctccagcag gaagcatctc gaagaacagc cctgccacac | 2040 |
| tctttgaagt tcctgacaca tggtaaccaa gacctgaggg cagcaaaccg ctggtgctgt | 2100 |
| cgctgtgagc aagagccggc tggcacattt ggaagccgca ctgtatttaa cttaatcaaa | 2160 |
| tgtggtatgg gagggttgg aaaccaagtt gtctcctggg ggagaaaa caggttttat | 2220 |
| ttttgtggct gtggttttt cccctttta atctaactgc ctgttgacat tgacactcat | 2280 |
| cacggttgta ggctgtcatg aatgtgtacg tgcttaacca gtgaattccg tgttgctctt | 2340 |
| gtgaggcctt tcctgtcatg acccagtgtg cttaagaacc tgcctgatgg ggagtgtcgg | 2400 |
| ctgtgaaatc tgcaaaaaga gctgacattc cagctgctgt gatcatgaat ttgggggtgt | 2460 |
| actgtcctgc ctgtgcatct tctcgcactg agatttgag gcagttgcag ccctcggtta | 2520 |
| gtctcccagt ggaaaaatcg gttgtgcctc cctgcttccc accatagctg cctgaaaaca | 2580 |
| tgacgctctc aagcttgtcc ttccttcagg aagatgtcca ctcatgccca cccatgagag | 2640 |

-continued

| | |
|---|---|
| ggcttgccgt atgccctggc cttTgggcat atttatgtag agttcctttc tcctaagacg | 2700 |
| tgagtttctc atgggggatg tacgagtaaa aaggttaact tctgttctta tgcgtggcgc | 2760 |
| tgtgttcact ttccagagtc tctgttcgtt tgtttggatg gcggtctcgg ggtacggcag | 2820 |
| cgtgtgtgcg tacgtgtctg tgtgtgtgtg tgtgtgtgtg tgtgtgtgtg | 2880 |
| tgtgtgaaat cgtgcaaatc tacaacatgt cccagcccat tctccgttga aacagatcac | 2940 |
| agcaacgaca aacgctcatg gcgctgcttt gctccacccg cttcagatag atcattgtta | 3000 |
| gatatttcac attttTgtat ggtggaaata aaatgaaaa atgtatttcc aaaagatgaa | 3060 |
| aattaaaaac attttcatag gac | 3083 |

<210> SEQ ID NO 2
<211> LENGTH: 8114
<212> TYPE: DNA
<213> ORGANISM: Homo sapiens

<400> SEQUENCE: 2

| | |
|---|---|
| acaacgcgct ccctgcgggg cgggcggcaa cctccatgcg gcctcgtcca cgctcagcac | 60 |
| cggggaagcc gaggcggaga agccgcgcgc gcctcagaag ctcccggacg cccagcggcg | 120 |
| gcgcgagcgg cggcggcggc agcagcagca gcagcagcac ggccaccggc gggagcggca | 180 |
| gcagcaccgg cagccccggc ggcgcggcct cggccccggc cccggccccg gccggcatgt | 240 |
| atcgctccgg ggagcgcctg ctgggcagcc acgcgctgcc cgcggagcag cgggacttcc | 300 |
| tgccccctaga gacgaccaac aacaacaaca accaccacca gcccggggcc tgggcccgcc | 360 |
| gggcgggctc ctcggcgtcc tcgcctccct cggcgtcctc gtccccgcac ccttcggccg | 420 |
| ccgtccccgc cgccgatcca gccgattcgg cctcgggcag cagcaacaag aggaagcgcg | 480 |
| acaacaaggc cagcacgtat ggactcaact acagcctgct gcagcccagc ggagggcggg | 540 |
| ccgcgggggg cggccgagca gacggcggcg gggtcgtgta cagcgggacc ccgtggaaac | 600 |
| ggaggaacta caaccaggga gtcgtgggtc tgcatgaaga aatcagtgat ttttatgaat | 660 |
| acatgtctcc aagacctgag gaggagaaga tgcggatgga ggtggtgaac aggatcgaga | 720 |
| gtgtaattaa ggagctctgg cccagcgctg acgtccagat attTggaagt tttaaaactg | 780 |
| gactttattt acctactagt gacatcgacc tagtggtgtt tgggaagtgg gagaacctac | 840 |
| ccctctggac tctggaagaa gctcttcgga acacaaagt cgcagatgag gattcggtga | 900 |
| aagttttaga caaagcaact gtacctatta ttaaattaac agattctttt actgaagtga | 960 |
| aagttgatat cagctttaat gtacagaatg gcgtgagagc agctgacctc atcaaagatt | 1020 |
| ttaccaagaa atatcctgta ttgccatact tggttttagt attgaaacaa ttcctattgc | 1080 |
| agagggacct taatgaagta tttacaggtg gaattggttc ttatagtctc tttttaatgg | 1140 |
| cagtcagttt ccttcagtta catcccaggg aagatgcttg catccccaat acaaactatg | 1200 |
| gtgttctctt aatagaattt tttgaattat atggacgaca cttcaattat ttaaagactg | 1260 |
| gcatccggat aaaggatggt ggttcatatg tggccaaaga tgaagtacag aaaaatatgc | 1320 |
| tagatggcta caggccatca atgctttata tcgaagatcc tttacaacca ggtaacgatg | 1380 |
| ttggaaggag ttcatatggg gccatgcaag tgaagcaggc ctttgattat gcctacgttg | 1440 |
| ttttgagtca tgctgtatca ccaatagcaa agtactatcc caacaatgaa acagaaagca | 1500 |
| tactaggtag aataattaga gtaacagatg aagttgccac atatagagat tggatatcaa | 1560 |
| agcagtgggg cttgaagaat agacctgagc cttcatgcaa tggaaatggt gttaccttga | 1620 |
| tagtagatac tcagcagtta gataaatgta ataataatct atctgaagaa aatgaagccc | 1680 |

```
ttggaaaatg tagaagtaaa acctcggaat ctcttagtaa acactcttca aactcttcat   1740
caggtccagt gtcgtcctct tctgccacac agtccagctc tagtgatgta gattccgatg   1800
caacaccatg caaaaccccg aaacagctgc tttgccgtcc gtccactggg aaccgagtag   1860
ggtcgcaaga tgtatccttg gagtcctctc aggcagttgg gaaaatgcaa agcacccaaa   1920
ccactaacac atccaacagc accaacaaat ctcagcatgg atcagcaagg ctctttcgtt   1980
cttccagcaa aggcttccaa ggtacaactc aaacaagcca tggttccttg atgacaaaca   2040
aacaacatca aggcaaatcc aataatcagt attaccatgg caaaagagg aaacacaaga    2100 gggacgcgcc cctctcagac ctctgtagat agtcagcgct gcgcggtgga ctgtcttctc   2160
tgtgcaatga tctcatgctc aggacagttg cgcagggact cctgggagat attcaggagc   2220
ctcacactgt tcagacgttg acttagcaac tgcgtttttt cccagctcgc cacagaatgg   2280
atcatgaaga ctgacaactg caaaaaaaac aaaacaaaac aaaaaaaaaa gcaagcaaaa   2340
aagagggaaa aaaaaggctg cttatttgat aagtcatatg ctacaacagg gtcattttaa   2400
gatttaaagc ttgaatgtaa aataaatata tttctcattg gctttatgca gagttatagg   2460
gaatagtatt cagtgttggt agggtgatag aaacaaaaaa cagtatcaga ggatgaggtg   2520
gggaaggaaa acaaaggtat ctgataggaa gtccagattc caaggggaa agtgatctgt    2580 gcatgttttt tttttaaata ttttttgcata tatttaccat tttattgtgt gtatatatag   2640
aagaccatat aggagattga tatttgtaat agtggatttg ttaataatac tttttacata   2700
acattactgt ttaaattgta aacagatttt ttctcaggat tagtttgaaa ataatctaa    2760 attgtcatct taacatccat atatagggaa gtgattagtt ctattactca atttgttttt   2820
ctcagcattg aaatgactta atagaaccct tgtgtcctgc tgcaaaaatt tttcctctct   2880
aaagaaaagg tttatggtgg caaatgatgt ttattttatt ttgtaaaaaa aaaaaaatgt   2940
actatgtact tttgtgtaaa cactgaaaaa tctctggtca tctccgagaa ttaacttgca   3000
actgttttct atagtgctgt cgtcttgggc aatgggcaat tacatgactt tgtgtttgct   3060
tcctttgcag tctttttttt ttcccccccat ttcttcctaa taggaaaaaa aaaaaaaaaa   3120
aggtcaccca tgtctggtct cattcctgtt gcagtgaaac ttcgagttcc acagactttg   3180
catgctggct tctctaaccc tgtgtgctgc gtgtgcctgt ttctcatctc ttattctttt   3240
taaaattcat gcttaactac tgtgggagaa taactgtaaa cagctttaat taaatcatac   3300
ttataaaaaa ctattttctt atattccact ctatgctttt ggtattgttg atctttacaa   3360
attaaatggt ctttgataat ggatctattt tgtattgcct tattaagacc aaatacttct   3420
tgtcatccca ttctttatcc tcttctttca tggaattgtt atcgttaatt aaaacttttt   3480
taaacattgg cttgtttcaa tcatactgta aattttggtt gtagtcagct ttgagtgcaa   3540
tgagatgtat aattctgtta tcattacctg ttgagtttga aactcagttg ggaatattta   3600
atataataga atgtaagtga catttctgaa aatgctttct ttcagggtga agctcttat    3660 gtttagcatc aatgtgtatg gctctgttaa atgcagccat ttctgagacg agattctttt   3720
atatatatat acatataaag tactattggc ttttaggagt ttctttttata tacatttatg  3780 aaatactgaa gaccaatcag accattaatg gacacttagt gtaacttttt ataagaaaa    3840 taatgctaaa gtaagaccaa aactgatgtc atcactgaaa ttaacaattt tcaatatgtt   3900
catattttaa ttcacaatgg aaaaatgtgt tccaaaactg gaaactcata gtactcgtgt   3960
aaactgtgga agatttcaaa tgtgatgtta ttttgacaat gttttaaatt ttagagtcac   4020
```

```
attttattct gatcagaatt tttattgaga tgttgagctt ttgttttga aactagtttg      4080 tcataacatt gtgcataatc acagtattta ttttctagga caattgtgaa tgtgtagact      4140
tatgtttact gctaagggaa caattattta taaaataata ttaaatccag tattagctgc      4200
ctatttcaga cacttaatac ttgcagagat ctatgttaca tttaccacac tgaagttttt      4260
tttgttgttt tttgtttgtt tttaaagaat caccctcatt gttgaaagta aatgtactct      4320
tagggtgcga atattagtgt tccaataagc atgtgattat attaaggtgg tggtagcggg      4380
aagataattc tgattccatt gggaatctta ggttttcgta aatttattgg gaaaatagtt      4440
tttcctgtac tgctgaagtt tcttttggt aaacagtatc tttctaaaag aaaaaagcat      4500
gaaggagaaa ttgaggtgtg tatacatttc ctcaaatgac cagcattgta ttcgtgaata      4560
ctgtgtatct tgcagtgaac agtgtggaag ctgttcattt ttcaatctga agtaaaatac      4620
tttcaagaac ttttagtttg cctgctcatt tgttttatac atttcatcta tttgactcct      4680
atcttatttc tttttttgagt tttaatactt cctatatttt gtgaatatat cagaaatgtg      4740
tcatttatat attagagtcc attcatatcc atgaatcata accttccttt gctaatactt      4800
gttgaatggg attttacaaa ttctccctca ctctggtgac atttctcagg cagtcatgta      4860
tgtgtacctg gccattagaa atattaatat ttaaagactg ttttttagag gagctgatgg      4920
gttggtgagg tgtcagcaca aaatcttact ggttatgttt tgatgataaa agtatatcca      4980 tttttttccct ccagctttaa ggtgactgtg aaggtgcctg gttttgaatg tctttgtttg      5040
gtttggagat gtcgcactca gttttcaaat ctagcttgga tctgtaggac ctatgttttt      5100
tacaagtaat tgccctccag tcttcaacag ttgattctgt tttattttta tcctgttttg      5160
agtgtacttt accttttactt gcattttgag cctcattaat atttaggtta tttgatttgg      5220
ctccagatat tcctagatct gcacagggca aaacatgggc tataggtga gcatttttaa      5280 ttgtcttttt ctgctggaac cttatatctc tccatgtgtt ttctgctcct tccctcccccc      5340 atgaaatggt aagtgtgact tgtgtttgcc tgaacctgtg gactagtgtt tggggtttct      5400
ggaaacacta gagggtcaga aaagagtaat gaccaccgtg acgtgcagga ttctcttgct      5460
gtgacatgtc cattgcaaag ccctctccag tgactaggag gtgtagttat taaggttgat      5520
ctgttagaaa tcaccattat taggtattag tggtagatgt tgctgatact tttattggtc      5580
atgactacat ctcagttta ctttaatatt gatctatagt ttgatcagtt ccttgaattc      5640
taatatgttg atttctcagt gtttctgtca ctaaccaaga atgtttctag gcagttggtt      5700
gcttcacagt caaaactaaa tggtaaacta tcaaaaatac attcccaatt ttgctgtgat      5760
aaatattgaa atgttaaaat taatgaacag aagaatttat tcttacccat ctattcttgt      5820
tctcctagtt cattaaactt tcagttattg gaaaggcaca ttctcaaagt attttatgag      5880
caaaatattc tataaatgcg tctaacaaac ctaattgaat ataaaagtta tatttagtag      5940
ttactgttga tagtaatttt catcagggtc atagttcatc tagtaaaata tttagagaat      6000
gatgttaaca ttccagcatt aaagtgggaa caaagattta tatatgaaat tccttaaaag      6060
agttcatctt gccttggttt ctgaccctca agactctagc tacctgccat cttgtcaaaa      6120
catttgtggg tagaataagt gttaaagatc aaatttaat atgcttctcg atatttaaca      6180
tagctaagaa gccagatttt actgtagaag ttatttacat gatttgaaaa cttgacctaa      6240
ctggaagcct ttttctcagt catcttgttc taagccatct tgacttcaca cccttagcga      6300
cttttctttt tttttggtc aaagataatg agctaaaatat atatagacgt tgaatgttga      6360
caaaattatt aaccagaaaa attgcttata aaggctgctg atctatttga tacctagaat      6420
```

-continued

```
taaatatttg aggacagttt ttagttaata aactgctaat gtttatttta ctgtctctca      6480 ggttttggt ttttttaaaa aaatgtgtt tggcctttac attttctact taagtgtgta        6540
ctttattgag tttaaccttg tctgtagcct agtagcctga agaaaagga gacagaacca       6600 gagagatgga tgtagtgcat tcccttggt tattacacat ttgtggtagc tcctggattt      6660
actgagagat attttagcta tgtcaataag aacagctaat gatgtggaaa tcaggtgttc     6720
tcttgtgtat ttcagtgaac atttttatta gtagttgcat atcatctcta gttccacatt     6780
ttaacttaac gtctttgtgg cttcaccact gagctacctt tcactacacc agcttctgtg     6840
tggcctggta acatggaagg tctctcctaa ggacagtctg gacgtatttt ggggaatgt      6900 tatttatctt aaagatgcct agaaacaaaa cgcatatagt accagtgaga aactatgaag     6960
taaacaagtt gctcaggccg ggcatggtgg ctcacgcctg taatcccagc actttgggag     7020
gccgaagcgg gaggatggct tgaggctggg agtttgagac cttcatctct taaaaaaaca    7080
aacaaaaacc tgaatggtga ggtgtggtgg aattgggtag gggagggaaa ggaggacttg    7140
gaaaagcatt ctccaaagcc agcaacttgg tgaagttcag tacttgcctc ttagaggtta    7200
ggccatgcct ttcaaagaga gtgaaatgat gggttatcag ccacattctt ggagttaata    7260 ttttcttca tctttcagtt tgggttctgt gctattcata gttcttccct aagaccattt     7320
cattattacc ttttatattt agttgcaatt tattataata tgttgttttg tccctgaact    7380
taatctccta attttaagat cctctctgat ttttgcatat tgaaacttac agaagtcact   7440 ttaaaaagt cttttgaaag tcctacaatc ctaaaataaa tcacaagctt gtttgttaga    7500
cgtgtcaaga gtctccagtc tttactacta aaaagcagca ctgccttaac acacattgtt    7560
atgggtgaaa agtgagggac gaccagtgta gtttctggat ataaagtgtg aaggactgtt    7620
gagttaaaca ttttagtgg aatatacata gataacgtgt atttagaaac tttggtgaag   7680
ccagtatttg ttttagtaa cctttttatg tatttccttc tttgattagc attgtcttca    7740
gtgttaagaa atgtggactc ctgtgaggtg ctggaggttt gaatcatctt gaaaactttc    7800
caatcttgtc tagttaccac tgcagagaca ctaaggaatt taccagaaaa agatatttga    7860
tacaagtgat ttaagaaatc tcaacatttc ctgaggccgt atcactgggc aaccagtgat    7920
gaaaactatg aatgaattgc acacctggaa gattttttaa gctaatgaca gtttcttcaa    7980
agatgtcaat tatttgcctt ggaaatttta taaattgcat ttctatgcac atcggcctct    8040
agtgcttacc actcggttta ttattcataa tctgcaattc aataaaggct tgtgttttc    8100 atttatcttc aaaa                                                       8114
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 3
gagggaaagg agcccagcct tg                                              22

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
tgaaggagcc ttggctatgc actg                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggtttaacc tggtggccac tgaa                                          24

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
attggctggg cacagtggct tg                                            22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agcccacctg tttgagaatg                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ccccaaagcc caaagttaat                                               20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcctgccgct aacatcccca aa                                            22

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 10
ggctgcatat gtgtactggc tgcac                                          25

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctaagcgtgc attgtgtgct                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcacttatgc tgtgccaaag                                                20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tcttggttga tgacttcatt cc                                             22

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccgcagaatt tcaaaaagga                                                20

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gagcaagggt aaggaaacat ttagca                                         26

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 16
tagccaagca tggtggcacg ag                                          22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
taatcgcttg aacccaggag                                             20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccaggttttt ctgccaattc                                             20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cgcaaagcac aggaaactaa                                             20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caaggctccc tgaaaattga                                             20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccaaaatgga ggaggaatga                                             20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
```
tctgggaaca tgctgcatac                                        20

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cccaacagct tgtttgagaa g                                      21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctcctgggtt caagcaattc                                        20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tcaaaatggc caatgtgttt                                        20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccagagccat tctgcttttc                                        20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gattggtagg gcaatgtgct                                        20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccatctgcaa accaggaagt                                           20

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgttttggtc tgaactttca ggcttgg                                   27

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
acacccggcc cctcatagga aa                                        22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gttgcagtga gccaagatca                                           20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cacagcccaa ttttgagtga                                           20

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ttcaagttgt tgtgggttct g                                         21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcttttatac gcaggccaaa a                                         21

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcctttgaac aggctaactc tc                                          22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aaaacaaacg aggcagcaat                                             20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ttgaccacct taggccacat                                             20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aggccatctt tcccaaaagt                                             20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgatggctgg ctgagtgtta                                             20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caccaagtga agccttgcta                                             20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctcttgtgag gcctttcctg                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
agcatgacat gaccagcaga                                              20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cccttagcca gcccgagcaa gt                                           22

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
actccgtcct ccaggccagc tt                                           22

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caggccatag aggaggccga ctt                                          23

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctcctgcacc attcgcctgt ga                                           22

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
aagtcgcggc cggcgtcacc                                                   20

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tggcctggta cactttgtga aga                                               23

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ggtacggcag cgtgtgtgcg ta                                                22

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tctgaagcgg gtggagcaaa gc                                                22

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
tcagtgatgg accttcagtc tctgcat                                           27

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
tgctatttca gtttggcctt tgcac                                             25

<210> SEQ ID NO 53

```
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggtttcggga aaacatagaa gttaaatg                                              28

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcaatgctgg agctctgaca aaca                                                  24

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gggaggggtg gtggccattt tt                                                    22

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
caccgcgaag agttgggctc tg                                                    22

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ctctgtcagc cgcgggtctc tc                                                    22

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gggttgcgga gggtgggcct                                                       20

<210> SEQ ID NO 59
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gaacgggcca gcagctgaca tt                                              22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcatgtgtga gccgagtcct gg                                              22

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
taatacgact cactataggg gggttgcgga gggtgggcct gg                        42

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ctacgtaacg attgatggtg cctacag                                         27

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
tgcattgcaa ggaagctgtg tgc                                             23

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ttgccgcaac ccagagacaa tg                                              22

<210> SEQ ID NO 65
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 65
gcttgatgcg ggtgctgagt ga                                              22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtcctggcgg ttgactccgt gt                                              22

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acagggtgaa gagttctggc acat                                            24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
tgaaggtgag gcttcccaac tcaa                                            24

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atgatgatat cgccgcgctc gt                                              22

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tgccgtgctc gatggggtac tt                                              22

<210> SEQ ID NO 71
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 71
atacttacct ggcaggggag ata                                              23

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gggaaagcgc gaacgcagtc                                                  20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cccccttcac cgagggccta                                                  20

<210> SEQ ID NO 74
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccggccgcac tgtatttaac ttaatctcga gattaagtta aatacagtgc ggttttg        58

<210> SEQ ID NO 75
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ccgggccttt ggtaacattc agatactcga gtatccaatc tctatatgtg gcttttg        58

<210> SEQ ID NO 76
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccggcgctga gtacttcgaa atgtcctcga ggacatttcg aagtactcag cgttttg        58

<210> SEQ ID NO 77
<211> LENGTH: 23
<212> TYPE: DNA
<213> ORGANISM: Artificial Sequence
<220> FEATURE:
```

<223> OTHER INFORMATION: Description of Artificial Sequence: Synthetic
oligonucleotide

<400> SEQUENCE: 77
agggagtcgt gggtctgcat gaa                                          23

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
atatctggac gtcagcgctg gg                                           22

<210> SEQ ID NO 79
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
ccgggccaca tatagagatt ggatactcga gtatccaatc tctatatgtg gcttttg     58

<210> SEQ ID NO 80
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
ccggccaaca aatctcagca tggatctcga gatccatgct gagatttgtt ggttttg     58

<210> SEQ ID NO 81
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
ccggcgcctg taatcccagc actttctcga gaaagtgctg ggattacagg cgttttg     58

<210> SEQ ID NO 82
<211> LENGTH: 58
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
ccgggcctgt aatcccagca ctttactcga gtaaagtgct gggattacag gcttttg     58

<210> SEQ ID NO 83
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 83
ccggcgatgt tggaaggagt tcatactcga gtatgaactc cttccaacat cgttttg          58

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
cggagcgata catgccggcc ggg                                               23

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
cggagcgata catgccggcc                                                   20

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
cgccgccgat ccagccgatt cgg                                               23

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
cgccgccgat ccagccgatt                                                   20

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cctcttgttg ctgctgcccg agg                                               23

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
cctcttgttg ctgctgcccg                                                                20

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
taatcttcac aaagtgtacc agg                                                            23

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
taatcttcac aaagtgtacc                                                                20

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gtatgatgaa aaacgttcac agg                                                            23

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gtatgatgaa aaacgttcac                                                                20

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tgaagtgtta ggagatacat agg                                                            23

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tgaagtgtta ggagatacat                                           20

<210> SEQ ID NO 96
<211> LENGTH: 639
<212> TYPE: PRT
<213> ORGANISM: Homo sapiens

<400> SEQUENCE: 96

Met Glu Ile Ile Arg Ser Asn Phe Lys Ser Asn Leu His Lys Val Tyr
1               5                   10                  15

Gln Ala Ile Glu Glu Ala Asp Phe Phe Ala Ile Asp Gly Glu Phe Ser
            20                  25                  30

Gly Ile Ser Asp Gly Pro Ser Val Ser Ala Leu Thr Asn Gly Phe Asp
        35                  40                  45

Thr Pro Glu Glu Arg Tyr Gln Lys Leu Lys Lys His Ser Met Asp Phe
    50                  55                  60

Leu Leu Phe Gln Phe Gly Leu Cys Thr Phe Lys Tyr Asp Tyr Thr Asp
65                  70                  75                  80

Ser Lys Tyr Ile Thr Lys Ser Phe Asn Phe Tyr Val Phe Pro Lys Pro
                85                  90                  95

Phe Asn Arg Ser Ser Pro Asp Val Lys Phe Val Cys Gln Ser Ser Ser
            100                 105                 110

Ile Asp Phe Leu Ala Ser Gln Gly Phe Asp Phe Asn Lys Val Phe Arg
        115                 120                 125

Asn Gly Ile Pro Tyr Leu Asn Gln Glu Glu Arg Gln Leu Arg Glu
    130                 135                 140

Gln Tyr Asp Glu Lys Arg Ser Gln Ala Asn Gly Ala Gly Ala Leu Ser
145                 150                 155                 160

Tyr Val Ser Pro Asn Thr Ser Lys Cys Pro Val Thr Ile Pro Glu Asp
                165                 170                 175

Gln Lys Lys Phe Ile Asp Gln Val Val Glu Lys Ile Glu Asp Leu Leu
            180                 185                 190

Gln Ser Glu Glu Asn Lys Asn Leu Asp Leu Glu Pro Cys Thr Gly Phe
        195                 200                 205

Gln Arg Lys Leu Ile Tyr Gln Thr Leu Ser Trp Lys Tyr Pro Lys Gly
    210                 215                 220

Ile His Val Glu Thr Leu Glu Thr Glu Lys Lys Glu Arg Tyr Ile Val
225                 230                 235                 240

Ile Ser Lys Val Asp Glu Glu Arg Lys Arg Arg Glu Gln Gln Lys
                245                 250                 255

His Ala Lys Glu Gln Glu Glu Leu Asn Asp Ala Val Gly Phe Ser Arg
            260                 265                 270

Val Ile His Ala Ile Ala Asn Ser Gly Lys Leu Val Ile Gly His Asn
        275                 280                 285

Met Leu Leu Asp Val Met His Thr Val His Gln Phe Tyr Cys Pro Leu
    290                 295                 300

Pro Ala Asp Leu Ser Glu Phe Lys Glu Met Thr Thr Cys Val Phe Pro
305                 310                 315                 320

Arg Leu Leu Asp Thr Lys Leu Met Ala Ser Thr Gln Pro Phe Lys Asp
                325                 330                 335

Ile Ile Asn Asn Thr Ser Leu Ala Glu Leu Glu Lys Arg Leu Lys Glu
            340                 345                 350

Thr Pro Phe Asn Pro Pro Lys Val Glu Ser Ala Glu Gly Phe Pro Ser 355                 360                 365
Tyr Asp Thr Ala Ser Glu Gln Leu His Glu Ala Gly Tyr Asp Ala Tyr
    370                 375                 380
Ile Thr Gly Leu Cys Phe Ile Ser Met Ala Asn Tyr Leu Gly Ser Phe
385                 390                 395                 400
Leu Ser Pro Pro Lys Ile His Val Ser Ala Arg Ser Lys Leu Ile Glu
                    405                 410                 415
Pro Phe Phe Asn Lys Leu Phe Leu Met Arg Val Met Asp Ile Pro Tyr
                420                 425                 430
Leu Asn Leu Glu Gly Pro Asp Leu Gln Pro Lys Arg Asp His Val Leu
            435                 440                 445
His Val Thr Phe Pro Lys Glu Trp Lys Thr Ser Asp Leu Tyr Gln Leu
        450                 455                 460
Phe Ser Ala Phe Gly Asn Ile Gln Ile Ser Trp Ile Asp Asp Thr Ser
465                 470                 475                 480
Ala Phe Val Ser Leu Ser Gln Pro Glu Gln Val Lys Ile Ala Val Asn
                    485                 490                 495
Thr Ser Lys Tyr Ala Glu Ser Tyr Arg Ile Gln Thr Tyr Ala Glu Tyr
                500                 505                 510
Met Gly Arg Lys Gln Glu Glu Lys Gln Ile Lys Arg Lys Trp Thr Glu
            515                 520                 525
Asp Ser Trp Lys Glu Ala Asp Ser Lys Arg Leu Asn Pro Gln Cys Ile
        530                 535                 540
Pro Tyr Thr Leu Gln Asn His Tyr Tyr Arg Asn Asn Ser Phe Thr Ala
545                 550                 555                 560
Pro Ser Thr Val Gly Lys Arg Asn Leu Ser Pro Ser Gln Glu Glu Ala
                    565                 570                 575
Gly Leu Glu Asp Gly Val Ser Gly Glu Ile Ser Asp Thr Glu Leu Glu
                580                 585                 590
Gln Thr Asp Ser Cys Ala Glu Pro Leu Ser Glu Gly Arg Lys Lys Ala
            595                 600                 605
Lys Lys Leu Lys Arg Met Lys Lys Glu Leu Ser Pro Ala Gly Ser Ile
        610                 615                 620
Ser Lys Asn Ser Pro Ala Thr Leu Phe Glu Val Pro Asp Thr Trp
625                 630                 635

<210> SEQ ID NO 97
<211> LENGTH: 572
<212> TYPE: PRT
<213> ORGANISM: Homo sapiens

<400> SEQUENCE: 97

Met Tyr Arg Ser Gly Glu Arg Leu Leu Gly Ser His Ala Leu Pro Ala
1               5                   10                  15
Glu Gln Arg Asp Phe Leu Pro Leu Glu Thr Thr Asn Asn Asn Asn Asn
                20                  25                  30
His His Gln Pro Gly Ala Trp Ala Arg Arg Ala Gly Ser Ser Ala Ser
            35                  40                  45
Ser Pro Pro Ser Ala Ser Ser Pro His Pro Ser Ala Ala Val Pro
        50                  55                  60
Ala Ala Asp Pro Ala Asp Ser Ala Ser Gly Ser Ser Asn Lys Arg Lys
65                  70                  75                  80
Arg Asp Asn Lys Ala Ser Gly Gly Arg Ala Ala Gly Gly Arg Ala
                85                  90                  95

```
Asp Gly Gly Gly Val Val Tyr Ser Gly Thr Pro Trp Lys Arg Arg Asn
            100                 105                 110

Tyr Asn Gln Gly Val Val Gly Leu His Glu Glu Ile Ser Asp Phe Tyr
        115                 120                 125

Glu Tyr Met Ser Pro Arg Pro Glu Glu Lys Met Arg Met Glu Val
    130                 135                 140

Val Asn Arg Ile Glu Ser Val Ile Lys Glu Leu Trp Pro Ser Ala Asp
145                 150                 155                 160

Val Gln Ile Phe Gly Ser Phe Lys Thr Gly Leu Tyr Leu Pro Thr Ser
                165                 170                 175

Asp Ile Asp Leu Val Val Phe Gly Lys Trp Glu Asn Leu Pro Leu Trp
            180                 185                 190

Thr Leu Glu Glu Ala Leu Arg Lys His Lys Val Ala Asp Glu Asp Ser
        195                 200                 205

Val Lys Val Leu Asp Lys Ala Thr Val Pro Ile Ile Lys Leu Thr Asp
    210                 215                 220

Ser Phe Thr Glu Val Lys Val Asp Ile Ser Phe Asn Val Gln Asn Gly
225                 230                 235                 240

Val Arg Ala Ala Asp Leu Ile Lys Asp Phe Thr Lys Lys Tyr Pro Val
                245                 250                 255

Leu Pro Tyr Leu Val Leu Val Leu Lys Gln Phe Leu Leu Gln Arg Asp
            260                 265                 270

Leu Asn Glu Val Phe Thr Gly Gly Ile Gly Ser Tyr Ser Leu Phe Leu
        275                 280                 285

Met Ala Val Ser Phe Leu Gln Leu His Pro Arg Glu Asp Ala Cys Ile
290                 295                 300

Pro Asn Thr Asn Tyr Gly Val Leu Leu Ile Glu Phe Phe Glu Leu Tyr
305                 310                 315                 320

Gly Arg His Phe Asn Tyr Leu Lys Thr Gly Ile Arg Ile Lys Asp Gly
                325                 330                 335

Gly Ser Tyr Val Ala Lys Asp Glu Val Gln Lys Asn Met Leu Asp Gly
            340                 345                 350

Tyr Arg Pro Ser Met Leu Tyr Ile Glu Asp Pro Leu Gln Pro Gly Asn
        355                 360                 365

Asp Val Gly Arg Ser Ser Tyr Gly Ala Met Gln Val Lys Gln Ala Phe
370                 375                 380

Asp Tyr Ala Tyr Val Val Leu Ser His Ala Val Ser Pro Ile Ala Lys
385                 390                 395                 400

Tyr Tyr Pro Asn Asn Glu Thr Glu Ser Ile Leu Gly Arg Ile Ile Arg
                405                 410                 415

Val Thr Asp Glu Val Ala Thr Tyr Arg Asp Trp Ile Ser Lys Gln Trp
            420                 425                 430

Gly Leu Lys Asn Arg Pro Glu Pro Ser Cys Asn Gly Pro Val Ser Ser
        435                 440                 445

Ser Ser Ala Thr Gln Ser Ser Ser Asp Val Asp Ser Asp Ala Thr
450                 455                 460

Pro Cys Lys Thr Pro Lys Gln Leu Leu Cys Arg Pro Ser Thr Gly Asn
465                 470                 475                 480

Arg Val Gly Ser Gln Asp Val Ser Leu Glu Ser Ser Gln Ala Val Gly
                485                 490                 495

Lys Met Gln Ser Thr Gln Thr Thr Asn Thr Ser Asn Ser Thr Asn Lys
            500                 505                 510

Ser Gln His Gly Ser Ala Arg Leu Phe Arg Ser Ser Ser Lys Gly Phe
```

```
            515                 520                 525
Gln Gly Thr Thr Gln Thr Ser His Gly Ser Leu Met Thr Asn Lys Gln
    530                 535                 540

His Gln Gly Lys Ser Asn Asn Gln Tyr Tyr His Gly Lys Lys Arg Lys
545                 550                 555                 560

His Lys Arg Asp Ala Pro Leu Ser Asp Leu Cys Arg
                565                 570
```

<210> SEQ ID NO 98
<211> LENGTH: 12
<212> TYPE: DNA
<213> ORGANISM: Homo sapiens

<400> SEQUENCE: 98
atgcagttcg ct                                                          12

<210> SEQ ID NO 99
<211> LENGTH: 451
<212> TYPE: DNA
<213> ORGANISM: Homo sapiens

<400> SEQUENCE: 99
gggttgcgga gggtgggcct gggaggggtg gtggccattt tttgtctaac cctaactgag      60
aagggcgtag gcgccgtgct tttgctcccc gcgcgctgtt tttctcgctg actttcagcg     120
ggcggaaaag cctcggcctg ccgccttcca ccgttcattc tagagcaaac aaaaaatgtc     180
agctgctggc ccgttcgccc ctcccgggga cctgcggcgg gtcgcctgcc agcccccga     240 accccgcctg gaggccgcgg tcggcccggg gcttctccgg aggcacccac tgccaccgcg     300
aagagttggg ctctgtcagc cgcgggtctc tcggggcga gggcgaggtt caggcctttc      360
aggccgcagg aagaggaacg gagcgagtcc ccgcgcgcgg cgcgattccc tgagctgtgg     420
gacgtgcacc caggactcgg ctcacacatg c                                     451

<210> SEQ ID NO 100
<211> LENGTH: 13
<212> TYPE: RNA
<213> ORGANISM: Homo sapiens

<400> SEQUENCE: 100
augcaguucg cua                                                         13

<210> SEQ ID NO 101
<211> LENGTH: 12
<212> TYPE: RNA
<213> ORGANISM: Homo sapiens

<400> SEQUENCE: 101
augcaguucg ca                                                          12

<210> SEQ ID NO 102
<211> LENGTH: 11
<212> TYPE: RNA
<213> ORGANISM: Homo sapiens

<400> SEQUENCE: 102
augcaguucg a                                                           11

<210> SEQ ID NO 103
<211> LENGTH: 10
<212> TYPE: RNA

```
<213> ORGANISM: Homo sapiens

<400> SEQUENCE: 103
augcaguuca                                                        10
```